US006891005B2

(12) United States Patent
Devore et al.

(10) Patent No.: US 6,891,005 B2
(45) Date of Patent: May 10, 2005

(54) BRIDGED METAL COMPLEXES FOR GAS PHASE POLYMERIZATIONS

(75) Inventors: David D. Devore, Midland, MI (US); David R. Neithamer, Midland, MI (US)

(73) Assignee: BP Chemicals Limited, London (GB)

( * ) Notice: Subject to any disclaimer, the term of this patent is extended or adjusted under 35 U.S.C. 154(b) by 234 days.

(21) Appl. No.: 10/323,975

(22) Filed: Dec. 20, 2002

(65) Prior Publication Data

US 2003/0199650 A1 Oct. 23, 2003

Related U.S. Application Data

(63) Continuation of application No. 09/383,995, filed on Aug. 26, 1999, now abandoned.
(60) Provisional application No. 60/103,511, filed on Oct. 8, 1998.

(51) Int. Cl.[7] .................................................. C08F 4/52
(52) U.S. Cl. ........................ 526/134; 526/172; 526/161; 526/943; 526/348
(58) Field of Search ................................. 526/134, 161, 526/172

(56) References Cited

U.S. PATENT DOCUMENTS 5,399,636 A * 3/1995 Alt et al. ..................... 526/129

FOREIGN PATENT DOCUMENTS

| EP | 514 828 A1 * | 5/1992 | ............. C07F/7/28 |
| WO | WO 98/39369 A1 * | 9/1998 | ........... C08F/10/00 |

OTHER PUBLICATIONS

Stelck et al. Organometallics 1997, 16,4546–4550.*
Herberhold, M. J. Organomet. Chem. 1997, 530, 117–120.*

* cited by examiner

*Primary Examiner*—David W. Wu
*Assistant Examiner*—Rip A Lee
(74) *Attorney, Agent, or Firm*—Finnegan, Henderson, Farabow, Garrett and Dunner, L.L.P.

(57) ABSTRACT

A gas phase olefin polymerization wherein the catalyst comprises a novel Group 4 transition metal complex containing a boron or aluminum bridging group containing a nitrogen containing group, especially an amido group.

15 Claims, No Drawings

BRIDGED METAL COMPLEXES FOR GAS PHASE POLYMERIZATIONS

CROSS-REFERENCE TO RELATED APPLICATION

This application is a continuation of U.S. application Ser. No. 09/383,995 filed Aug. 26, 1999, now abandoned, which claims benefit of priority from provisional application 60/103,511, filed Oct. 8, 1998.

BACKGROUND OF THE INVENTION

This invention relates to the use of certain bridged Group 4 transition metal complexes possessing a unique bridge structure in a gas-phase olefin polymerization catalyst. The unique bridge consists of either boron or aluminum atoms which are further ligated with nitrogen containing groups. The unique bridging structures in the complexes provides for gas-phase olefin polymerization catalysts with exceptionally high catalytic efficiency, and processes giving unique polymer properties.

In *Angew. Chem. Int. Ed. Engl.*, 36, 21, p2338–2340 (1997) and in *Phosphorus, Sulfur, and Silicon*, 124 & 125, p561–565 (1997) amido substituted boron bridged ferrocenophanes useful for forming poly(ferrocenes) by a ring opening polymerization were disclosed. The synthesis and characterization of Group 1 and 2 metal and tin complexes of 1,2-bis(dimethylamino)-1,2-di-9-fluorenyldiboranes were disclosed in *Chem. Ber.*, 127, p1901–1908, (1994). Diboranes having structure similar to those employed in the foregoing study were disclosed by the same researchers in *Eur. J. Inorg. Chem.*, p505–509 (1998). Ferrocenophane derivatives of similar bisboranes for further molecular property studies were disclosed by *J. Organomet. Chem.*, 530 p117–120 (1997). In *Organometallics*, 16, p4546–4550 (1997) boron bridged ansa metallocene complexes including dimethylsulifide and phosphine adducts thereof of possible use in Ziegler-Natta-type olefin polymerizations were disclosed.

In the patent literature, bridged metal complexes for use as olefin polymerization catalyst components, including such complexes containing one or more boron atoms in the bridge are generically disclosed by EP-A-416,815 and WO 98/39369.

SUMMARY OF THE INVENTION

The present invention relates to the use of certain bridged Group 4 transition metal comprises as olefin polymerization catalysts in a gas-phase olefin polymerization, wherein said complexes correspond to the following formulas:

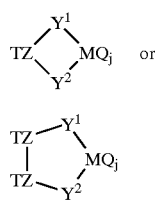

wherein:

M is titanium, zirconium, or hafnium in the +4, +3, or +2 oxidation state;

$Y^1$ and $Y^2$ are independently an anionic, cyclic or non-cyclic, π-bonded group, $NR^1$, $PR^1$; $NR^1_2$ or $PR^1_2$;

Z is boron or aluminum;

Q is a neutral, anionic or dianionic ligand group depending on the oxidation state of M;

j is 1, 2 or 3 depending on the oxidation state of M and the electronic nature of Q;

T independently each occurrence is:

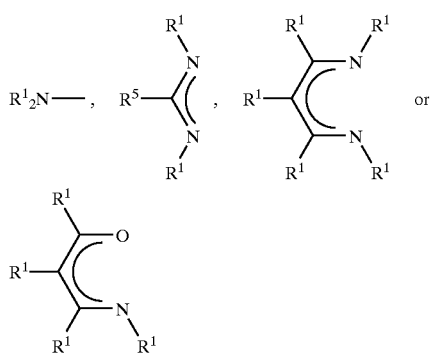

$R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;

$R^5$ is $R^1$ or $N(R^1)_2$; and two $R^1$ groups together or one or more $R^1$ groups together with $R^5$ may optionally be joined to form a ring structure.

It is understood that the foregoing metal complexes may exist as dimers and that one or more Lewis bases may optionally be coordinated with the complex or the dimer thereof and that when $Y^1$ or $Y^2$ are the neutral ligands, $NR^1_2$ or $PR^1_2$, the bond to M is a coordinate-covalent bond rather than a covalent bond. In addition, when T is $R^1_2N$ and Z is boron, the bond between T and Z, particularly in the compounds of formula 1, may possess double bonds characteristics, that is, the resulting group is more accurately depicted by the formula $R^1_2N=B$. In addition, suitable catalyst compositions desirably additionally comprise an activating cocatalyst and a support.

DETAILED DESCRIPTION

The foregoing metal complexes are produced by reaction of a metallated derivative of a compound of one of the formulas:

wherein Z, T, $R^1$ and $R^5$ are as defined above;

$Y^{1'}$ and $Y^{2'}$ are an anionic, cyclic or non-cyclic, π-bonded group, $NR^1$, or $PR^1$; and $R^4$ is hydrogen or a timethylsilyl group, with a metal salt of the formula $MY^3_4$, where M is a Group 4 metal, and Y3 is a leaving group, especially halide. The reactants may be combined either as neat reagents or in an inert solvent. Temperatures from −100° C. to 150° C. are preferred.

In a particularly preferred embodiment, the complexes of formula 1 and formula 2 are prepared in high racemic purity in the +2 formal oxidation state by contacting the metallated derivatives of compounds of formula 1A or formula 2A, with a Group 4 precursor of the formula 3:

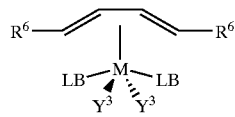

Formula 3 wherein M and $Y^3$ are defined as above, $R^6$ independently each occurrence is hydrogen, a hydrocarbyl group, a tri(hydrocarbyl)silyl group, or a tri(hydrocarbyl)silylhydrocarbyl group, said $R^6$ groups containing up to 20 atoms not counting hydrogen; and LB is a Lewis base, especially an ether, amine, or phosphine of up to 20 carbons.

The complexes are desirably prepared in an inert solvent, especially an aliphatic or aromatic hydrocarbon or ether, employing temperatures from −100° C. to 150° C. This technique is similar to that disclosed in United States patent application 265,641, filed Mar. 10, 1999, differing in that different starting reagents are employed.

The process of the present invention can be used in combination with one or more additional polymerization processes either in parallel or series, using the same or different reactors.

Because the catalyst compositions possess improved catalytic efficiencies and improved thermal stability, they are particularly adapted for use under higher operating temperatures and poor thermal transport conditions, such as are commonly encountered under gas phase polymerization conditions.

All references to the Periodic Table of the Elements herein shall refer to the Periodic Table of the Elements, published and copyrighted by CRC Press, Inc. 1997. Also, any references to a Group or Groups shall be to the Groups or Groups reflected in this Periodic Table of the Elements using the IUPAC system for numbering groups. Where any reference is made herein to any publication, patent application or provisional patent application, the contents thereof are incorporated herein in its entirety by reference. By the term "π-bonded" as used herein is meant that bonding occurs through an interaction involving delocalized electrons. Finally, by the term, "leaving group" is meant a ligand that is readily displaced by another ligand under ligand exchange conditions.

The present Group 4 transition metal complexes contain a unique bridging group: (T-Z) or (T-Z)$_2$, which imparts improved catalytic properties when used in combination with one or more activating cocatalysts or activating techniques in the presence of addition polymerizable monomers. While not desiring to be bound by theory, it is believed that the improvement in catalytic properties for such complexes may be due to electron donating or electron withdrawing properties of the $Y^1$ and $Y_2$ moieties.

Preferred Group 4 transition metal complexes are those that correspond to formula 1 or 2 are represented in formulas 4, 5, 6, 7, 8 and 9:

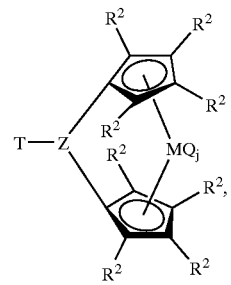

Formula 4

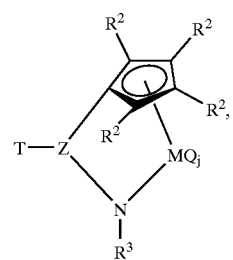

Formula 5

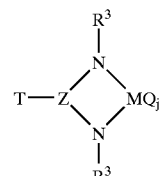

Formula 6

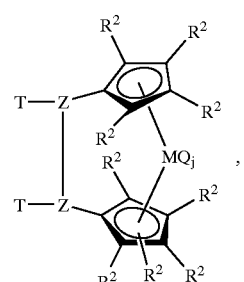

Formula 7

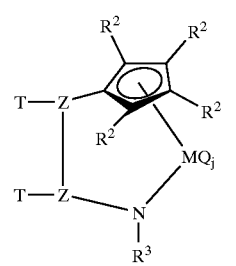

Formula 8 or

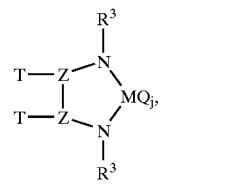

Formula 9 wherein M, Z, T, Q and j are as defined above;

$R^2$ is hydrogen, or a hydrocarbyl, halohydrocarbyl, dihydrocarbylaminohydrocarbal, tri(hydrocarbylsilyl) hydrocarbyl, Si(R$^3$)$_3$, N(R$^3$)$_2$, or OR$^3$ group of up to 20 carbon or silicon atoms, and optionally two adjacent R2 groups can be joined together, thereby forming a fused ring structure, especially an indenyl ligand or a substituted indenyl ligand; and $R^3$ is independently hydrogen, a hydrocarbyl group, a trihydrocarbylsilyl group or a trihydrocarbylsilylhydrocarbyl group, said $R^3$ having up to 20 atoms not counting hydrogen.

When M is in the +4° oxidation state, j=2 and Q independently each occurrence is halide, hydride, hydrocarbyl, silylhydrocarbyl, hydrocarbyloxide, dihydrocarbylamide, said Q having up to 20 atoms not counting hydrogen. Alternatively, two Q groups may be joined together to form an alkanediyl group or a conjugated $C_{4-40}$ diene ligand which is coordinated to M in a metallocyclopentene fashion.

When M is in the +3 oxidation state, j=1 and Q is either 1) a monovalent anionic stabilizing ligand selected from the group consisting of alkyl, cycloalkyl, aryl, silyl, amido, phosphido, alkoxy, aryloxy, sulfido groups, and mixtures thereof, and being further substituted with an amine, phosphine, ether, or thioether containing substituent able to form a coordinate-covalent bond or chelating bond with M said ligand having up to 50 atoms not counting hydrogen; or 2) a $C_{3-10}$ hydrocarbyl group comprising an ethylenic unsaturation able to form an $\eta^3$ bond with M.

When M is in the +2 oxidation state, j=1 and Q is a neutral conjugated diene, optionally substituted with one or more tri(hydrocarbyl)silyl or tri(hydrocarbylsilyl)hydrocarbyl groups, said Q having up to 40 carbon atoms and forming a π-complex with M.

Specific examples of the above metal complexes wherein M is in the +4 oxidation state are shown below in formulas 4a–9a, wherein the definitions of M, Z, $R^1$, $R^2$, and $R^3$ are as defined above.

Specific examples of the above metal complexes wherein M is in the +4 oxidation state are shown below in formulas 4a–9a, wherein the definitions of M, Z, $R^1$, $R^2$, and $R^3$ are as defined above.

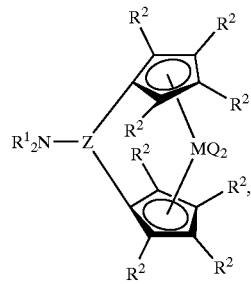

Formula 4a

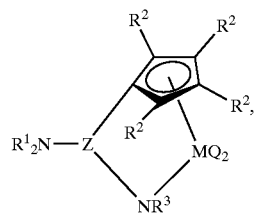

Formula 5a

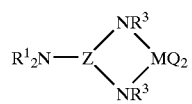

Formula 6a

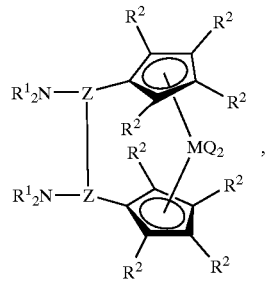

Formula 7a

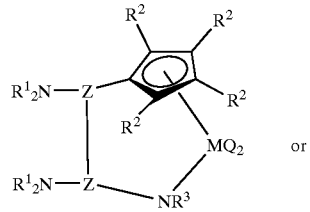

Formula 8a

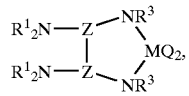

Formula 9a wherein Q, independently each occurrence is a halide, hydrocarbyl, hydrocarbyloxy, or dihydrocarbylamide group of up to 10 atoms not counting hydrogen, or two Q groups together form a $C_{4-20}$ diene ligand coordinated to M in a metallocyclopentene fashion. Most highly preferably Q independently each occurrence is chloride or $C_{1-6}$ hydrocarbyl groups, or two Q groups together form a 2-methyl-1,3-butadienyl or 2,3-dimethyl-1,3-butadienyl group.

Specific examples of the above metal complexes wherein M is in the +3 oxidation state are shown below in formulas 4b–9b, wherein the definitions of M, Z, $R^1$, $R^2$, and $R^3$ are as defined above.

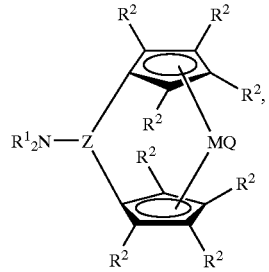

Formula 4b

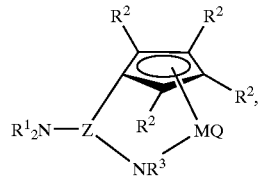

Formula 5b

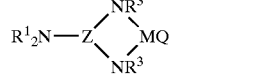

Formula 6b

Formula 7b

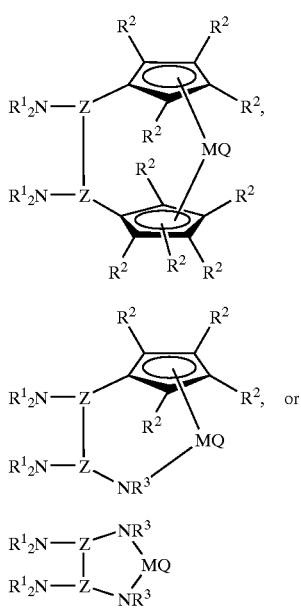

Formula 8b

Formula 9b

Formula 7c

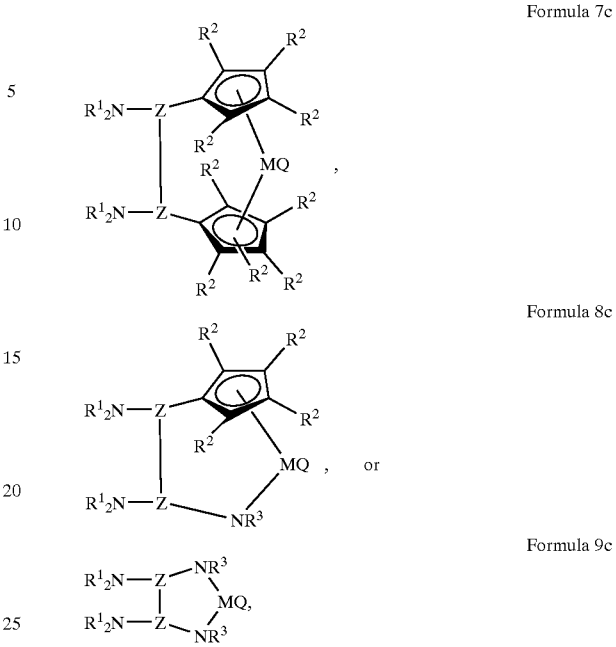

Formula 8c

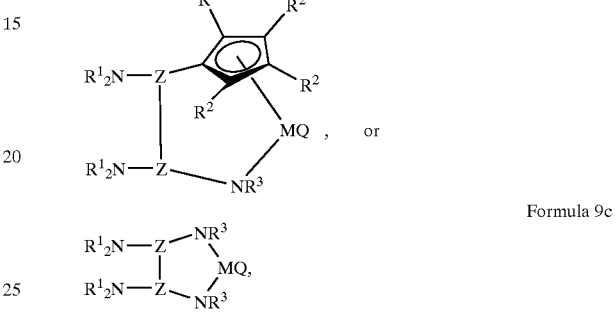

Formula 9c

wherein Q, each occurrence is a monovalent anionic stabilizing ligand selected from the group consisting of alkyl, cycloalkyl, aryl, and silyl groups which are further substituted with one or more amine, phosphine, or ether substituents able to form a coordinate-covalent bond or chelating bond with M, and Q having up to 30 nonhydrogen atoms; or Q is a $C_{3-10}$ hydrocarbyl group consisting an ethylenic unsaturation able to form an η3 bond with M. Most highly preferred examples of such Q ligands are 2-N-N-dimethylaminobenzyl, allyl, and 1-methyl-allyl.

Specific examples of the above metal complexes wherein M is in the +2 oxidation state are shown below in formulas 4c–9c, wherein the definitions of M, Z, $R^1$, $R^2$, and $R^3$ are as defined above.

Formula 4c

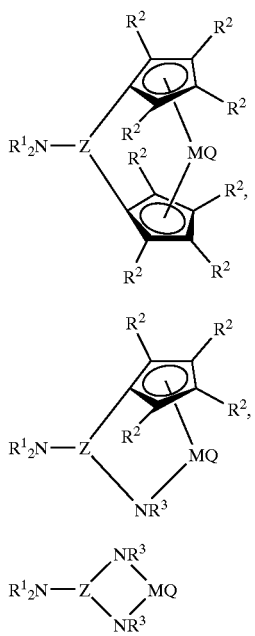

Formula 5c

Formula 6c wherein Q, each occurrence is a neutral conjugated diene, optionally substituted with one or more tri(hydrocarbyl)silyl groups or tri(hydrocarbyl)silylhydrocarbyl groups, said Q having up to 30 atoms not counting hydrogen and forming a π-complex with M. Most highly preferred Q groups are 1,4-diphenyl-1,3-butadiene, 1,3-pentadiene, 3-methyl-1,3 pentadiene, 2,4-hexadiene, 1-phenyl-1,3-pentadiene, 1,4-dibenzyl-1,3 butadiene, 1,4-ditolyl-1,3-butadiene, 1,4-bis (trimethylsilyl)-1,3-butadiene, and 1,4-dinaphthyl-1,3-butadiene.

Preferably in the foregoing formulas, $R^1$ independently each occurrence is $C_{1-4}$ alkyl or phenyl, more preferably methyl or isopropyl, most preferably methyl, $Y^1$ and $Y^2$ are both inden-1-yl, 2-alkyl-4-arylinden-1-yl, or 3-alkylinden-1-yl, or $Y^1$ is cyclopentadienyl or alkyl-substituted cyclopentadienyl and $Y^2$ is fluorenyl; Z is boron and Q is halide, alkyl, N,N-dialkylamido, or 1,4-diphenyl-1,3-butadiene (said alkyl or aryl groups having up to 10 carbons). Even more preferably in formulas 4a–c and 8a–c, M is zirconium or hafnium and $R^1$ is methyl or isopropyl, most preferably methyl. During synthesis of these complexes, the use of methyl $R^1$ groups gives elevated, often quantitative, yields of the rac isomer.

In formulas 5a–c, 6a–c, 8a–c and 9a–c, M is even more preferably titanium, Z is boron and $R^1$ is $C_{1-4}$ alkyl or phenyl, most preferably methyl or isopropyl.

Most highly preferred metal complexes are those of formulas 4a–c and 8a–c wherein $Y^1$ and $Y^2$ are both inden-1-yl, 2-methyl-4-phenylinden-1-yl, 3-isopropylinden-1-yl, or 3-t-butylinden-1-yl groups, especially compositions comprising greater than 90 percent rac isomer.

Specific, but not limiting, metal complexes included with the invention described in the foregoing formulas are:

dimethylamidoborane-bis-$\eta^5$-cyclopentadienyl zirconium dichloride;
dimethylamidoborane-bis-$\eta^5$-cyclopentadienyl zirconium dimethyl;
dimethylamidoborane-bis-$\eta^5$-cyclopentadienyl zirconium bis-dimethylamide;
dimethylamidoborane-bis-$\eta^5$-cyclopentadienyl zirconium 2-methyl-1,3-butadiene;

dimethylamidoborane-bis-η⁵-cyclopentadienyl zirconium 2,3-dimethyl-1,3-butadiene;
dimethylamidoborane-bis-η⁵-cyclopentadienyl zirconium 2-N,N-dimethylaminobenzyl;
dimethylamidoborane-bis-η⁵-cyclopentadienyl zirconium allyl;
dimethylamidoborane-bis-η⁵-cyclopentadienyl zirconium η⁴-1,4-diphenyl-1,3-butadiene;
dimethylamidoborane-bis-η⁵-cyclopentadienyl zirconium η⁴-2,4-hexadiene;
dimethylamidoborane-bis-η⁵-cyclopentadienyl zirconium η⁴-1,4-dinaphthyl-1,3-butadiene;
dimethylamidoborane-bis-η⁵-cyclopentadienyl zirconium η⁴-1-phenyl-1,3-pentadiene;
dimethylamidoborane-bis-η⁵-cyclopentadienyl zirconium η⁵-1,3-pentadiene;
dimethylamidoborane-bis-η⁵-n-butylcyclopentadienyl zirconium dichloride;
dimethylamidoborane-bis-η⁵-n-butylcyclopentadienyl zirconium dimethyl;
dimethylamidoborane-bis-η⁵-n-butylcyclopentadienyl bis-dimethylamide;
dimethylamidoborane-bis-η⁵-n-butylcyclopentadienyl zirconium 2-methyl-1,3-butadiene;
dimethylamidoborane-bis-η⁵-n-butylcyclopentadienyl zirconium 2,3-dimethyl-1,3-butadiene;
dimethylamidoborane-bis-η⁵-n-butylcyclopentadienyl zirconium 2-N,N-dimethylaminobenzyl;
dimethylamidoborane-bis-η⁵-n-butylcyclopentadienyl zirconium allyl;
dimethylamidoborane-bis-η⁵-n-butylcyclopentadienyl zirconium η⁴-1,4-diphenyl-1,3-butadiene;
dimethylamidoborane-bis-η⁵-n-butylcyclopentadienyl zirconium η⁴-2,4-hexadiene;
dimethylamidoborane-bis-η⁵-n-butylcyclopentadienyl zirconium η⁴-1,4-dinaphthyl-1,3-butadiene;
dimethylamidoborane-bis-η⁵-n-butylcyclopentadienyl zirconium η⁴-1-phenyl-1,3-pentadiene;
dimethylamidoborane-bis-η⁵-n-butylcyclopentadienyl zirconium η⁵-1,3-pentadiene;
dimethylamidoborane-bis-η⁵-inden-1-ylzirconium dichloride;
dimethylamidoborane-bis-η⁵-inden-1-ylzirconium dimethyl;
dimethylamidoborane-bis-η⁵-inden-1-ylzirconium bis-dimethylamide;
dimethylamidoborane-bis-η⁵-inden-1-ylzirconium 2-methyl-1,3-butadiene;
dimethylamidoborane-bis-η⁵-inden-1-ylzirconium 2,3-dimethyl-1,3-butadiene;
dimethylamidoborane-bis-η⁵-inden-1-ylzirconium 2-N,N-dimethylaminobenzyl;
dimethylamidoborane-bis-η⁵-inden-1-ylzirconium allyl;
dimethylamidoborane-bis-η⁵-inden-1-ylzirconium η⁴-1,4-diphenyl-1,3-butadiene;
dimethylamidoborane-bis-η⁵-inden-1-ylzirconium η⁴-2,4-hexadiene;
dimethylamidoborane-bis-η⁵-inden-1-ylzirconium η⁴-1,4-dinaphthyl-1,3-butadiene;
dimethylamidoborane-bis-η⁵-inden-1-ylzirconium η⁴-1-phenyl-1,3-pentadiene;
dimethylamidoborane-bis-η⁵-inden-1-ylzirconium η⁴-1,3-pentadiene;
dimethylamidoborane-bis-η⁵-(2-methylinden-1-yl)zirconium dichloride;
dimethylamidoborane-bis-η⁵-(2-methylinden-1-yl)zirconium dimethyl;
dimethylamidoborane-bis-η⁵-(2-methylinden-1-yl)zirconium bis-dimethylamide;
dimethylamidoborane-bis-η⁵-(2-methylinden-1-yl)zirconium 2-methyl-1,3-butadiene;
dimethylamidoborane-bis-η⁵-(2-methylinden-1-yl)zirconium 2,3-dimethyl-1,3-butadiene;
dimethylamidoborane-bis-η⁵-(2-methylinden-1-yl)zirconium 2-N,N-dimethylaminobenzyl;
dimethylamidoborane-bis-η⁵-(2-methylinden-1-yl)zirconium allyl;
dimethylamidoborane-bis-η⁵-(2-methylinden-1-yl)zirconium η⁴-1,4-diphenyl-1,3-butadiene;
dimethylamidoborane-bis-η⁵-(2-methylinden-1-yl)zirconium η⁴-2,4-hexadiene;
dimethylamidoborane-bis-η⁵-(2-methylinden-1-yl)zirconium η⁴-1,4-dinaphythyl-1,3-butadiene;
dimelhylamidoborane-bis-η⁵-(2-methylinden-1-yl)zirconium η⁴-1-phenyl-1,3-pentadiene;
dimethylamidoborane-bis-η⁵-(2-methylinden-1-yl)zirconium η⁴-1,3-pentadiene;
dimethylamidoborane-bis-η⁵-(2-methyl-4-phenylinden-1-yl)zirconium dichloride;
dimethylamidoborane-bis-η⁵-(2-methyl-4-phenylinden-1-yl)zirconium dimethyl;
dimethylamidoborane-bis-η⁵-(2-methyl-4-phenylinden-1-yl)zirconium bis-dimethylamide;
dimethylamidoborane-bis-η⁵-(2-methyl-4-phenylinden-1-yl)zirconium 2-methyl-1,3-butadiene;
dimethylamidoborane-bis-η⁵-(2-methyl-4-phenylinden-1-yl)zirconium 2,3-dimethyl-1,3-butadiene;
dimethylamidoborane-bis-η⁵-(2-methyl-4-phenylinden-1-yl)zirconium 2-N,N-dimethylaminobenzyl;
dimethylamidoborane-bis-η⁵-(2-methyl-4-phenylinden-1-yl)zirconium allyl;
dimethylamidoborane-bis-η⁵-(2-methyl-4-phenylinden-1-yl)zirconium η⁴-1,4-diphenyl-1,3-butadiene;
dimethylamidoborane-bis-η⁵-(2-methyl-4-phenylinden-1-yl)zirconium η⁴-2,4-hexadiene;
dimethylamidoborane-bis-η⁵-(2-methyl-4-phenylinden-1-yl)zirconium η⁴-dinaphthyl-1,3-butadiene;
dimethylamidoborane-bis-η⁵-(2-methyl-4-phenylinden-1-yl)zirconium η⁴-1-phenyl-1,3-pentadiene;
dimethylamidoborane-bis-η⁵-(2-methyl-4-phenylinden-1-yl)zirconium η⁴-1,3-pentadiene;
dimethylamidoborane-bis-η⁵-(2-ethyl-4-phenylinden-1-yl)zirconium dichloride;
dimethylamidoborane-bis-η⁵-(2-ethyl-4-phenylinden-1-yl)zirconium dimethyl;
dimethylamidoborane-bis-η⁵-(2-ethyl-4-phenylinden-1-yl)zirconium bis-dimethylamine;
dimethylamidoborane-bis-η⁵-(2-ethyl-4-phenylinden-1-yl)zirconium 2-methyl-1,3-butadiene;
dimethylamidoborane-bis-η⁵-(2-ethyl-4-phenylinden-1-yl)zirconium 2,3-dimethyl-1,3-butadiene;
dimethylamidoborane-bis-η⁵-(2-ethyl-4-phenylinden-1-yl)zirconium 2-N,N-dimethylaminobenzyl;
dimethylamidoborane-bis-η⁵-(2-ethyl-4-phenylinden-1-yl)zirconium allyl;
dimethylamidoborane-bis-η⁵-(2-ethyl-4-phenylinden-1-yl)zirconium η⁴-1,4-diphenyl-1,3-butadiene;
dimethylamidoborane-bis-η⁵-(2-ethyl-4-phenylinden-1-yl)zirconium η⁴-2,4-hexadiene;
dimethylamidoborane-bis-η⁵-(2-ethyl-4-phenylinden-1-yl)zirconium η⁴-1,4-dinaphthyl-1,3-butadiene;
dimethylamidoborane-bis-η⁵-(2-ethyl-4-phenylinden-1-yl)zirconium η⁴-1-phenyl-1,3-pentadiene;
dimethylamidoborane-bis-η⁵-(2-ethyl-4-phenylinden-1-yl)zirconium η⁴-1,3-pentadiene dimethylamidoborane-bis-η⁵-(2-isopropyl-4-phenylinden-1-yl)zirconium dichloride;
dimethylamidoborane-bis-η⁵-(2-isopropyl-4-phenylinden-1-yl)zirconium dimethyl;
dimethylamidoborane-bis-η⁵-(2-isopropyl-4-phenylinden-1-yl)zirconium bis-dimethylamide;
dimethylamidoborane-bis-η⁵-(2-isopropyl-4-phenylinden-1-yl)zirconium 2-methyl-1,3-butadiene;
dimethylamidoborane-bis-η⁵-(2-isopropyl-4-phenylinden-1-yl)zirconium 2,3-dimethyl-1,3-butadiene;
dimethylamidoborane-bis-η⁵-(2-isopropyl-4-phenylinden-1-yl)zirconium 2-N,N-dimethylaminobenzyl;
dimethylamidoborane-bis-η⁵-(2-isopropyl-4-phenylinden-1-yl)zirconium allyl;
dimethylamidoborane-bis-η⁵-(2-isopropyl-4-phenylinden-1-yl)zirconium η⁴-diphenyl-1,3-butadiene;
dimethylamidoborane-bis-η⁵-(2-isopropyl-4-phenylinden-1-yl)zirconium η⁴-hexadiene;
dimethylamidoborane-bis-η⁵-(2-isopropyl-4-phenylinden-1-yl)zirconium η⁴-dinaphthyl-1,3-butadiene;
dimethylamidoborane-bis-η⁵-(2-isopropyl-4-phenylinden-1-yl)zirconium η⁴-phenyl-1,3-pentadiene;
dimethylamidoborane-bis-η⁵-(2-isopropyl-4-phenylinden-1-yl)zirconium η⁴-1,3-pentadiene;
dimethylamidoborane-bis-η⁵-(2-methyl-4-naphthylinden-1-yl)zirconium dichloride;
dimethylamidoborane-bis-η⁵-(2-methyl-4-naphthylinden-1-yl)zirconium dimethyl;
dimethylamidoborane-bis-η⁵-(2-methyl-4-naphthylinden-1-yl)zirconium bis-dimethylamide;
dimethylamidoborane-bis-η⁵-(2-methyl-4-naphthylinden-1-yl)zirconium 2-methyl-1,3-butadiene;
dimethylamidoborane-bis-η⁵-(2-methyl-4-naphthylinden-1-yl)zirconium 2,3-dimethyl-1,3-butadiene;
dimethylamidoborane-bis-η⁵-(2-methyl-4-naphthylinden-1-yl)zirconium 2-N,N-dimethylaminobenzyl;
dimethylamidoborane-bis-η⁵-(2-methyl-4-naphthylinden-1-yl)zirconium allyl;
dimethylamidoborane-bis-η⁵-(2-methyl-4-naphthylinden-1-yl)zirconium η⁴-1,4-diphenyl-1,3-butadiene;
dimethylamidoborane-bis-η⁵-(2-methyl-4-naphthylinden-1-yl)zirconium η⁴-2,4-hexadiene;
dimethylamidoborane-bis-η⁵-(2-methyl-4-naphthylinden-1-yl)zirconium η⁴-1,4-dinaphthyl-1,3-butadiene;
dimethylamidoborane-bis-η⁵-(2-methyl-4-naphthylinden-1-yl)zirconium η⁴-1-phenyl-1,3-pentadiene;
dimethylamidoborane-bis-η⁵-(2-methyl-4-naphthylinden-1-yl)zirconium η⁴-1,3-pentadiene;
dimethylamidoborane-bis-η⁵-(2-methyl-4-bis(3,5-trifluoromethyl)phenylinden-1-yl)zirconium dichloride;
dimethylamidoborane-bis-η⁵-(2-methyl-4-bis(3,5-trifluoromethyl)phenylinden-1-yl)zirconium dimethyl;
dimethylamidoborane-bis-η⁵-(2-methyl-4-bis(3,5-trifluoromethyl)phenylinden-1-yl)zirconium bis-dimethylamide;
dimethylamidoborane-bis-η⁵-(2-methyl-4-bis(3,5-trifluoromethyl)phenylinden-1-yl)zirconium 2-methyl-1,3-butadiene;
dimethylamidoborane-bis-η⁵-(2-methyl-4-bis(3,5-trifluoromethyl)phenylinden-1-yl)zirconium 2,3-dimethyl-1,3-butadiene;
dimethylamidoborane-bis-η⁵-(2-methyl-4-bis(3,5-trifluoromethyl)phenylinden-1-yl)zirconium 2-N,N-dimethylaminobenzyl;
dimethylamidoborane-bis-η⁵-(2-methyl-4-bis(3,5-trifluoromethyl)phenylinden-1-yl)zirconium allyl;
dimethylamidoborane-bis-η⁵-(2-methyl-4-bis(3,5-trifluoromethyl)phenylinden-1-yl)zirconium η⁴-1,4-diphenyl-1,3-butadiene;
dimethylamidoborane-bis-η⁵-(2-methyl-4-bis(3,5-trifluoromethyl)phenylinden-1-yl)zirconium η⁴-2,4-hexadiene;
dimethylamidoborane-bis-η⁵-(2-methyl-4-bis(3,5-trifluoromethyl)phenylinden-1-yl)zirconium η⁴-1,4-dinaphthyl-1,3-butadiene;
dimethylamidoborane-bis-η⁵-(2-methyl-4-bis(3,5-trifluoromethyl)phenylinden-1-yl)zirconium η⁴-1-phenyl-1,3-pentadiene;
dimethylamidoborane-bis-η⁵-(2-methyl-4-bis(3,5-trifluoromethyl)phenylinden-1-yl)zirconium η⁴-1,3-pentadiene;
dimethylamidoborane-bis-η⁵-(2-ethyl-4-bis(3,5-trifluoromethyl)phenylinden-1-yl)zirconium dichloride;
dimethylamidoborane-bis-η⁵-(2-ethyl-4-bis(3,5-trifluoromethyl)phenylinden-1-yl)zirconium dimethyl;
dimethylamidoborane-bis-η⁵-(2-ethyl-4-bis(3,5-trifluoromethyl)phenylinden-1-yl)zirconium bis-dimethylamide;
dimethylamidoborane-bis-η⁵-(2-ethyl-4-bis(3,5-trifluoromethyl)phenylinden-1-yl)zirconium 2-methyl-1,3-butadiene;
dimethylamidoborane-bis-η⁵-(2-ethyl-4-bis(3,5-trifluoromethyl)phenylinden-1-yl)zirconium 2,3-dimethyl-1,3-butadiene;
dimethylamidoborane-bis-η⁵-(2-ethyl-4-bis(3,5-trifluoromethyl)phenylinden-1-yl)zirconium 2-N,N-dimethylaminobenzyl;
dimethylamidoborane-bis-η⁵-(2-ethyl-4-bis(3,5-trifluoromethyl)phenylinden-1-yl)zirconium allyl;
dimethylamidoborane-bis-η⁵-(2-ethyl-4-bis(3,5-trifluoromethyl)phenylinden-1-yl)zirconium η⁴-1,4-diphenyl-1,3-butadiene;
dimethylamidoborane-bis-η⁵-(2-ethyl-4-bis(3,5-trifluoromethyl)phenylinden-1-yl)zirconium η⁴-2,4-hexadiene;
dimethylamidoborane-bis-η⁵-(2-ethyl-4-bis(3,5-trifluoromethyl)phenylinden-1-yl)zirconium η⁴-1,4-dinaphthyl-1,3-butadiene;
dimethylamidoborane-bis-η⁵-(2-ethyl-4-bis(3,5-trifluoromethyl)phenylinden-1-yl)zirconium η⁴-1-phenyl-1,3-pentadiene;
dimethylamidoborane-bis-η⁵-(2-ethyl-4-bis(3,5-trifluoromethyl)phenylinden-1-yl)zirconium η⁴-1,3-pentadiene;
dimethylamidoborane-bis-η⁵-(2-isopropyl-4-bis(3,5-trifluoromethyl)phenylinden-1-yl)zirconium dichloride;
dimethylamidoborane-bis-η⁵-(2-isopropyl-4-bis(3,5-trifluoromethyl)phenylinden-1-yl)zirconium dimethyl;
dimethylamidoborane-bis-η⁵-(2-isopropyl-4-bis(3,5-trifluoromethyl)phenylinden-1-yl)zirconium bis-dimethylamide;
dimethylamidoborane-bis-η⁵-(2-isopropyl-4-bis(3,5-trifluoromethyl)phenylinden-1-yl)zirconium 2-methyl-1,3-butadiene;
dimethylamidoborane-bis-η⁵-(2-isopropyl-4-bis(3,5-trifluoromethyl)phenylinden-1-yl)zirconium 2,3-dimethyl-1,3-butadiene;
dimethylamidoborane-bis-η⁵-(2-isopropyl-4-bis(3,5-trifluoromethyl)phenylinden-1-yl)zirconium 2-N,N-dimethylaminobenzyl;
dimethylamidoborane-bis-η⁵-(2-isopropyl-4-bis(3,5-trifluoromethyl)phenylinden-1-yl)zirconium allyl;
dimethylamidoborane-bis-η⁵-(2-isopropyl-4-bis(3,5-trifluoromethyl)phenylinden-1-yl)zirconium η⁴-1,4-diphenyl-1,3-butadiene;
dimethylamidoborane-bis-η⁵-(2-isopropyl-4-bis(3,5-trifluoromethyl)phenylinden-1-yl)zirconium η⁴-2,4-hexadiene;

dimethylamidoborane-bis-η⁵-(2-isopropyl-4-bis(3,5-trifluoromethyl)phenylinden-1-yl)zirconium η⁴-1,4-dinaphthyl-1,3-butadiene;
dimethylamidoborane-bis-η⁵-(2-isopropyl-4-bis(3,5-trifluoromethyl)phenylinden-1-yl)zirconium η⁴-1,3-pentadiene;
dimethylamidoborane-bis-η⁵-(2-isopropyl-4-bis(3,5-trifluoromethyl)phenylinden-1-yl)zirconium η⁴-1,3-pentadiene;
dimethylamidoborane-bis-η⁵-(3-isopropylinden-1-yl) zirconium dichloride;
dimethylamidoborane-bis-η⁵-(3-isopropylinden-1-yl) zirconium dimethyl;
dimethylamidoborane-bis-η⁵-(3-isopropylinden-1-yl) zirconium bis-dimethylamide;
dimethylamidoborane-bis-η⁵-(3-isopropylinden-1-yl) zirconium 2-methyl-1,3-butadiene;
dimethylamidoborane-bis-η⁵-(3-isopropylinden-1-yl) zirconium 2,3-dimethyl-1,3-butadiene;
dimethylamidoborane-bis-η⁵-(3-isopropylinden-1-yl) zirconium 2-N,N-dimethylaminobenzyl;
dimethylamidoborane-bis-η⁵-(3-isopropylinden-1-yl) zirconium allyl;
dimethylaminoborane-bis-η⁵-(3-isopropylinden-1-yl) zirconium η⁴-1,4-diphenyl-1,3-butadiene;
dimethylaminoborane-bis-η⁵-(3-isopropylinden-1-yl) zirconium η⁴-2,4-hexadiene;
dimethylaminoborane-bis-η⁵-(3-isopropylinden-1-yl) zirconium η⁴-1,4-dinaphthyl-1,3-butadiene;
dimethylaminoborane-bis-η⁵-(3-isopropylinden-1-yl) zirconium η⁴-1-phenyl-1,3-pentadiene;
dimethylaminoborane-bis-η⁵-(3-isopropylinden-1-yl) zirconium η⁴-1,3-pentadiene;
dimethylamidoborane-bis-η⁵-(3-t-butylinden-1-yl) zirconium dichloride;
dimethylamidoborane-bis-η⁵-(3-t-butylinden-1-yl) zirconium dimethyl;
dimethylamidoborane-bis-η⁵-(3-t-butylinden-1-yl) zirconium bis-dimethylamine;
dimethylamidoborane-bis-η⁵-(3-t-butylinden-1-yl) zirconium 2-methyl-1,3-butadiene;
dimethylamidoborane-bis-η⁵-(3-t-butylinden-1-yl) zirconium 2,3-dimethyl-1,3-butadiene;
dimethylamidoborane-bis-η⁵-(3-t-butylinden-1-yl) zirconium 2-N,N-dimethylaminobenzyl;
dimethylamidoborane-bis-η⁵-(3-t-butylinden-1-yl) zirconium allyl;
dimethylamidoborane-bis-η⁵-(3-t-butylinden-1-yl) zirconium η⁴-1,4-diphenyl-1,3-butadiene;
dimethylamidoborane-bis-η⁵-(3-t-butylinden-1-yl) zirconium η⁴-2,4-hexadiene;
dimethylamidoborane-bis-η⁵-(3-t-butylinden-1-yl) zirconium η⁴-1,4-dinaphthyl-1,3-butadiene;
dimethylamidoborane-bis-η⁵-(3-t-butylinden-1-yl) zirconium η⁴-1-phenyl-1,3-pentadiene;
dimethylamidoborane-bis-η⁵-(3-t-butylinden-1-yl) zirconium η⁴-1,3-pentadiene;
diisopropylamidoborane-bis-η⁵-cyclopentadienylzirconium dichloride;
diisopropylamidoborane-bis-η⁵-cyclopentadienylzirconium dimethyl;
diisopropylamidoborane-bis-η⁵-cyclopentadienylzirconium bis-dimethylamide;
diisopropylamidoborane-bis-η⁵-cyclopentadienylzirconium 2-methyl-1,3-butadiene;
diisopropylamidoborane-bis-η⁵-cyclopentadienylzirconium 2,3-dimethyl-1,3-butadiene;
diisopropylamidoborane-bis-η⁵-cyclopentadienylzirconium 2-N,N-dimethylaminobenzyl;
diisopropylamidoborane-bis-η⁵-cyclopentadienylzirconium allyl;
diisopropylamidoborane-bis-η⁵-cyclopentadienylzirconium η⁴-1,4-diphenyl-1,3-butadiene;
diisopropylamidoborane-bis-η⁵-cyclopentadienylzirconium η⁴-2,4-hexadiene;
diisopropylamidoborane-bis-η⁵-cyclopentadienylzirconium η⁴-1,4-dinaphthyl-1,3-butadiene;
diisopropylamidoborane-bis-η⁵-cyclopentadienylzirconium η⁴-1-phenyl-1,3-pentadiene;
diisopropylamidoborane-bis-η⁵-cyclopentadienylzirconium η⁵-1,3-pentadiene;
diisopropylamidoborane-bis-η⁵-inden-1-ylzirconium dichloride;
diisopropylamidoborane-bis-η⁵-inden-1-ylzirconium dimethyl;
diisopropylamidoborane-bis-η⁵-inden-1-ylzirconium bis-dimethylamide;
diisopropylamidoborane-bis-η⁵-inden-1-ylzirconium 2-methyl-1,3-butadiene;
diisopropylamidoborane-bis-η⁵-inden-1-ylzirconium 2,3-dimethyl-1,3-butadiene;
diisopropylamidoborane-bis-η⁵-inden-1-ylzirconium 2-N,N-dimethylaminobenzyl;
diisopropylamidoborane-bis-η⁵-inden-1-ylzirconium allyl;
diisopropylamidoborane-bis-η⁵-inden-1-ylzirconium η⁴-1,4-diphenyl-1,3-butadiene;
diisopropylamidoborane-bis-η⁵-inden-1-ylzirconium η⁴-2,4-hexadiene;
diisopropylamidoborane-bis-η⁵-inden-1-ylzirconium η⁴-1,4-dinaphthyl-1,3-butadiene;
diisopropylamidoborane-bis-η⁵-inden-1-ylzirconium η⁴-1-phenyl-1,3-pentadiene;
diisopropylamidoborane-bis-η⁵-inden-1-ylzirconium η⁴-1,3-pentadiene;
diisopropylamidoborane-bis-η⁵-(2-methylinden-1yl) zirconium dichloride;
diisopropylamidoborane-bis-η⁵-(2-methylinden-1-yl) zirconium dimethyl;
diisopropylamidoborane-bis-η⁵-(2-methylinden-1-yl) zirconium bis-dimethylamide;
diisopropylamidoborane-bis-η⁵-(2-methylinden-1-yl) zirconium 2-methyl-1,3-butadiene;
diisopropylamidoborane-bis-η⁵-(2-methylinden-1-yl) zirconium 2,3-dimethyl-1,3-butadiene;
diisopropylamidoborane-bis-η⁵-(2-methylinden-1-yl) zirconium 2-N,N-dimethylaminobenzyl;
diisopropylamidoborane-bis-η⁵-(2-methylinden-1-yl) zirconium allyl;
diisopropylamidoborane-bis-η⁵-(2-methylinden-1-yl) zirconium η⁴-1,4-diphenyl-1,3-butadiene;
diisopropylamidoborane-bis-η⁵-(2-methylinden-1-yl) zirconium η⁴-2,4-hexadiene;
diisopropylamidoborane-bis-η⁵-(2-methylinden-1-yl) zirconium η⁴-1,4-dinaphthyl-1,3-butadiene;
diisopropylamidoborane-bis-η⁵-(2-methylinden-1-yl) zirconium η⁴-1-phenyl-1,3-pentadiene;
diisopropylamidoborane-bis-η⁵-(2-methylinden-1-yl) zirconium η⁴-1,3-pentadiene;
diisopropylamidoborane-bis-η⁵-(2-methyl-4-phenylinden-1-yl)zirconium dichloride;
diisopropylamidoborane-bis-η⁵-(2-methyl-4-phenylinden-1-yl)zirconium dimethyl;
diisopropylamidoborane-bis-η⁵-(2-methyl-4-phenylinden-1-yl)zirconium bis-dimethylamide;

diisopropylamidoborane-bis-$\eta^5$-(2-methyl-4-phenylinden-1-yl)zirconium 2-methyl-1,3-butadiene;
diisopropylamidoborane-bis-$\eta^5$-(2-methyl-4-phenylinden-1-yl)zirconium 2,3-dimethyl-1,3-butadiene;
diisopropylamidoborane-bis-$\eta^5$-(2-methyl-4-phenylinden-1-yl)zirconium 2-N,N-dimethylaminobenzyl;
diisopropylamidoborane-bis-$\eta^5$-(2-methyl-4-phenylinden-1-yl)zirconium allyl;
diisopropylamidoborane-bis-$\eta^5$-(2-methyl-4-phenylinden-1-yl)zirconium $\eta^4$-1,4-diphenyl-1,3-butadiene;
diisopropylamidoborane-bis-$\eta^5$-(2-methyl-4-phenylinden-1-yl)zirconium $\eta^4$-2,4-hexadiene;
diisopropylamidoborane-bis-$\eta^5$-(2-methyl-4-phenylinden-1-yl)zirconium $\eta^4$-1,4-dinaphthyl-1,3-butadiene;
diisopropylamidoborane-bis-$\eta^5$-(2-methyl-4-phenylinden-1-yl)zirconium $\eta^4$-1-phenyl-1,3-pentadiene;
diisopropylamidoborane-bis-$\eta^5$-(2-methyl-4-phenylinden-1-yl)zirconium $\eta^4$-1,3-pentadiene;
diisopropylamidoborane-bis-$\eta^5$-(2-methyl-4-naphthylinden-1-yl)zirconium dichloride;
diisopropylamidoborane-bis-$\eta^5$-(2-methyl-4-naphthylinden-1-yl)zirconium dimethyl;
diisopropylamidoborane-bis-$\eta^5$-(2-methyl-4-naphthylinden-1-yl)zirconium bis-dimethylamide;
diisopropylamidoborane-bis-$\eta^5$-(2-methyl-4-naphthylinden-1-yl)zirconium 2-methyl-1,3-butadiene;
diisopropylamidoborane-bis-$\eta^5$-(2-methyl-4-naphthylinden-1-yl)zirconium 2,3-dimethyl-1,3-butadiene;
diisopropylamidoborane-bis-$\eta^5$-(2-methyl-4-naphthylinden-1-yl)zirconium 2-N,N-dimethylaminobenzyl;
diisopropylamidoborane-bis-$\eta^5$-(2-methyl-4-naphthylinden-1-yl)zirconium allyl;
diisopropylamidoborane-bis-$\eta^5$-(2-methyl-4-naphthylinden-1-yl)zirconium $\eta^4$-1,4-diphenyl-1,3-butadiene;
diisopropylamidoborane-bis-$\eta^5$-(2-methyl-4-naphthylinden-1-yl)zirconium $\eta^4$-2,4-hexadiene;
diisopropylamidoborane-bis-$\eta^5$-(2-methyl-4-naphthylinden-1-yl)zirconium $\eta^4$-1,4-dinaphthyl-1,3-butadiene;
diisopropylamidoborane-bis-$\eta^5$-(2-methyl-4-naphthylinden-1-yl)zirconium $\eta^4$-1-phenyl-1,3-pentadiene;
diisopropylamidoborane-bis-$\eta^5$-(2-methyl-4-naphthylinden-1-yl)zirconium $\eta^4$-1,3-pentadiene;
diisopropylamidoborane-bis-$\eta^5$-(2-methyl-4-(3,5-dimethylphenyl)inden-1-yl)zirconium dichloride;
diisopropylamidoborane-bis-$\eta^5$-(2-methyl-(3,5-dimethylphenyl)inden-1-yl)zirconium dimethyl;
diisopropylamidoborane-bis-$\eta^5$-(2-methyl-(3,5-dimethylphenyl)inden-1-yl)zirconium bis-dimethylamide;
diisopropylamidoborane-bis-$\eta^5$-(2-methyl-(3,5-dimethylphenyl)inden-1-yl)zirconium 2-methyl-1,3-butadiene;
diisopropylamidoborane-bis-$\eta^5$-(2-methyl-4-(3,5-dimethylphenyl)inden-1-yl)zirconium 2,3-dimethyl-1,3-butadiene;
diisopropylamidoborane-bis-$\eta^5$-(2-methyl-4-(3,5-dimethylphenyl)inden-1-yl)zirconium 2-N,N-dimethylaminobenzyl;
diisopropylamidoborane-bis-$\eta^5$-(2-methyl-4-(3,5-dimethylphenyl)inden-1-yl)zirconium allyl;
diisopropylamidoborane-bis-$\eta^5$-(2-methyl-4-(3,5-dimethylphenyl)inden-1-yl)zirconium $\eta^4$-1,4-diphenyl-1,3-butadiene;
diisopropylamidoborane-bis-$\eta^5$-(2-methyl-4-(3,5-dimethylphenyl)inden-1-yl)zirconium $\eta^4$-2,4-hexadiene;
diisopropylamidoborane-bis-$\eta^5$-(2-methyl-4-(3,5-dimethylphenyl)inden-1-yl)zirconium $\eta^4$-1,4-dinaphthyl-1,3-butadiene;
diisopropylamidoborane-bis-$\eta^5$-(2-methyl-4-(3,5-dimethylphenyl)inden-1-yl)zirconium $\eta^4$-1-phenyl-1,3-pentadiene;
diisopropylamidoborane-bis-$\eta^5$-(2-methyl-4-(3,5-dimethylphenyl)inden-1-yl)zirconium $\eta^4$-1,3-pentadiene;
diisopropylamidoborane-bis-$\eta^5$-(2-methyl-4-(3,5-difluoromethylphenyl)inden-1-yl)zirconium dichloride;
diisopropylamidoborane-bis-$\eta^5$-(2-methyl-4-(3,5-difluoromethylphenyl)inden-1-yl)zirconium dimethyl;
diisopropylamidoborane-bis-$\eta^5$-(2-methyl-4-(3,5-difluoromethylphenyl)inden-1-yl)zirconium bis-dimethylamide;
diisopropylamidoborane-bis-$\eta^5$-(2-methyl-4-(3,5-difluoromethylphenyl)inden-1-yl)zirconium 2-methyl-1,3-butadiene;
diisopropylamidoborane-bis-$\eta^5$-(2-methyl-4-(3,5-difluoromethylphenyl)inden-1-yl)zirconium 2,3-dimethyl-1,3-butadiene;
diisopropylamidoborane-bis-$\eta^5$-(2-methyl-4-(3,5-difluoromethylphenyl)inden-1-yl)zirconium 2-N,N-dimethylaminobenzyl;
diisopropylamidoborane-bis-$\eta^5$-(2-methyl-4-(3,5-difluoromethylphenyl)inden-1-yl)zirconium allyl;
diisopropylamidoborane-bis-$\eta^5$-(2-methyl-4-(3,5-difluoromethylphenyl)inden-1-yl)zirconium $\eta^4$-1,4-diphenyl-1,3-butadiene;
diisopropylamidoborane-bis-$\eta^5$-(2-methyl-4-(3,5-difluoromethylphenyl)inden-1-yl)zirconium $\eta^4$-2,4-hexadiene;
diisopropylamidoborane-bis-$\eta^5$-(2-methyl-4-(3,5-difluoromethylphenyl)inden-1-yl)zirconium $\eta^4$-1,4-dinaphthyl-1,3-butadiene;
diisopropylamidoborane-bis-$\eta^5$-(2-methyl-4-(3,5-difluoromethylphenyl)inden-1-yl)zirconium $\eta^4$-1-phenyl-1,3-pentadiene;
diisopropylamidoborane-bis-$\eta^5$-(2-methyl-4-(3,5-difluoromethylphenyl)inden-1-yl)zirconium $\eta^4$-1,3-pentadiene;
diisopropylamidoborane-bis-$\eta^5$-(2-ethyl-4-phenylinden-1-yl)zirconium dichloride;
diisopropylamidoborane-bis-$\eta^5$-(2-ethyl-4-phenylinden-1-yl)zirconium dimethyl;
diisopropylamidoborane-bis-$\eta^5$-(2-ethyl-4-phenylinden-1-yl)zirconium bis-dimethylamide;
diisopropylamidoborane-bis-$\eta^5$-(2-ethyl-4-phenylinden-1-yl)zirconium 2-methyl-1,3-butadiene;
diisopropylamidoborane-bis-$\eta^5$-(2-ethyl-4-phenylinden-1-yl)zirconium 2,3-dimethyl-1,3-butadiene;
diisopropylamidoborane-bis-$\eta^5$-(2-ethyl-4-phenylinden-1-yl)zirconium 2-N,N-dimethylaminobenzyl;
diisopropylamidoborane-bis-$\eta^5$-(2-ethyl-4-phenylinden-1-yl)zirconium allyl;
diisopropylamidoborane-bis-$\eta^5$-(2-ethyl-4-phenylinden-1-yl)zirconium $\eta^4$-1,4-diphenyl-1,3-butadiene;
diisopropylamidoborane-bis-$\eta^5$-(2-ethyl-4-phenylinden-1-yl)zirconium $\eta^4$-2,4-hexadiene;
diisopropylamidoborane-bis-$\eta^5$-(2-ethyl-4-phenylinden-1-yl)zirconium $\eta^4$-1,4-dinaphthyl-1,3-butadiene;
diisopropylamidoborane-bis-$\eta^5$-(2-ethyl-4-phenylinden-1-yl)zirconium $\eta^4$-1-phenyl-1,3-pentadiene;
diisopropylamidoborane-bis-$\eta^5$-(2-ethyl-4-phenylinden-1-yl)zirconium $\eta^4$-1,3-pentadiene;

diisopropylamidoborane-bis-$\eta^5$-(2-isopropyl-4-phenylinden-1-yl)zirconium dichloride;
diisopropylamidoborane-bis-$\eta^5$-(2-isopropyl-4-phenylinden-1-yl)zirconium dimethyl;
diisopropylamidoborane-bis-$\eta^5$-(2-isopropyl-4-phenylinden-1-yl)zirconium bis-dimethylamide;
diisopropylamidoborane-bis-$\eta^5$-(2-isopropyl-4-phenylinden-1-yl)zirconium 2-methyl-1,3-butadiene;
diisopropylamidoborane-bis-$\eta^5$-(2-isopropyl-4-phenylinden-1-yl)zirconium 2,3-dimethyl-1,3-butadiene;
diisopropylamidoborane-bis-$\eta^5$-(2-isopropyl-4-phenylinden-1-yl)zirconium 2-N,N-dimethylaminobenzyl;
diisopropylamidoborane-bis-$\eta^5$-(2-isopropyl-4-phenylinden-1-yl)zirconium allyl;
diisopropylamidoborane-bis-$\eta^5$-(2-isopropyl-4-phenylinden-1-yl)zirconium $\eta^4$-1,4-diphenyl-1,3-butadiene;
diisopropylamidoborane-bis-$\eta^5$-(2-isopropyl-4-phenylinden-1-yl)zirconium $\eta^4$-2,4-hexadiene;
diisopropylamidoborane-bis-$\eta^5$-(2-isopropyl-4-phenylinden-1-yl)zirconium $\eta^4$-1,4-dinaphthyl-1,3-butadiene;
diisopropylamidoborane-bis-$\eta^5$-(2-isopropyl-4-phenylinden-1-yl)zirconium $\eta^4$-1-phenyl-1,3-pentadiene;
diisopropylamidoborane-bis-$\eta^5$-(2-isopropyl-4-phenylinden-1-yl)zirconium $\eta^4$-1,3-pentadiene;
diisopropylamidoborane-bis-$\eta^5$-(3-isopropylinden-1-yl)zirconium dichloride;
diisopropylamidoborane-bis-$\eta^5$-(3-isopropylinden-1-yl)zirconium dimethyl;
diisopropylamidoborane-bis-$\eta^5$-(3-isopropylinden-1-yl)zirconium bis-dimethylamide;
diisopropylamidoborane-bis-$\eta^5$-(3-isopropylinden-1-yl)zirconium 2-methyl-1,3-butadiene;
diisopropylamidoborane-bis-$\eta^5$-(3-isopropylinden-1-yl)zirconium 2,3-dimethyl-1,3-butadiene;
diisopropylamidoborane-bis-$\eta^5$-(3-isopropylinden-1-yl)zirconium 2-N,N-dimethylaminobenzyl;
diisopropylamidoborane-bis-$\eta^5$-(3-isopropylinden-1-yl)zirconium allyl;
diisopropylamidoborane-bis-$\eta^5$-(3-isopropylinden-1-yl)zirconium $\eta^4$-1,4-diphenyl-1,3-butadiene;
diisopropylamidoborane-bis-$\eta^5$-(3-isopropylinden-1-yl)zirconium $\eta^4$-2,4-hexadiene;
diisopropylamidoborane-bis-$\eta^5$-(3-isopropylinden-1-yl)zirconium $\eta^4$-1,4-dinaphthyl-1,3-butadiene;
diisopropylamidoborane-bis-$\eta^5$-(3-isopropylinden-1-yl)zirconium $\eta^4$-1-phenyl-1,3-pentadiene;
diisopropylamidoborane-bis-$\eta^5$-(3-isopropylinden-1-yl)zirconium $\eta^4$-1,3-pentadiene;
diisopropylamidoborane-bis-$\eta^5$-(3-t-butylinden-1-yl)zirconium dichloride;
diisopropylamidoborane-bis-$\eta^5$-(3-t-butylinden-1-yl)zirconium dimethyl;
diisopropylamidoborane-bis-$\eta^5$-(3-t-butylinden-1-yl)zirconium bis-dimethylamide;
diisopropylamidoborane-bis-$\eta^5$-(3-t-butylinden-1-yl)zirconium 2-methyl-1,3-butadiene;
diisopropylamidoborane-bis-$\eta^5$-(3-t-butylinden-1-yl)zirconium 2,3-dimethyl-1,3-butadiene;
diisopropylamidoborane-bis-$\eta^5$-(3-t-butylinden-1-yl)zirconium 2-N,N-dimethylaminobenzyl;
diisopropylamidoborane-bis-$\eta^5$-(3-t-butylinden-1-yl)zirconium allyl;
diisopropylamidoborane-bis-$\eta^5$-(3-t-butylinden-1-yl)zirconium $\eta^4$-1,4-diphenyl-1,3-butandiene;
diisopropylamidoborane-bis-$\eta^5$-(3-t-butylinden-1-yl)zirconium $\eta^4$-2,4-hexadiene;
diisopropylamidoborane-bis-$\eta^5$-(3-t-butylinden-1-yl)zirconium $\eta^4$-1,4-dinaphthyl-1,3-butandiene;
diisopropylamidoborane-bis-$\eta^5$-(3-t-butylinden-1-yl)zirconium $\eta^4$-1-phenyl-1,3-pentadiene;
diisopropylamidoborane-bis-$\eta^5$-(3-t-butylinden-1-yl)zirconium $\eta^4$-1,3-pentadiene;
diphenylamidoborane-bis-$\eta^5$-cyclopentadienyl zirconium dichloride;
diphenylamidoborane-bis-$\eta^5$-cyclopentadienyl zirconium dimethyl;
diphenylamidoborane-bis-$\eta^5$-cyclopentadienyl zirconium bis-dimethylamide;
diphenylamidoborane-bis-$\eta^5$-cyclopentadienyl zirconium 2-methyl-1,3-butadiene;
diphenylamidoborane-bis-$\eta^5$-cyclopentadienyl zirconium 2,3-dimethyl-1,3-butadiene;
diphenylamidoborane-bis-$\eta^5$-cyclopentadienyl zirconium 2-N,N-dimethylaminobenzyl;
diphenylamidoborane-bis-$\eta^5$-cyclopentadienyl zirconium allyl;
diphenylamidoborane-bis-$\eta^5$-cyclopentadienyl zirconium $\eta^4$-1,4-diphenyl-1,3-butadiene;
diphenylamidoborane-bis-$\eta^5$-cyclopentadienyl zirconium $\eta^4$-2,4-hexadiene;
diphenylamidoborane-bis-$\eta^5$-cyclopentadienyl zirconium $\eta^4$-1,4-dinaphthyl-1,3-butadiene;
diphenylamidoborane-bis-$\eta^5$-cyclopentadienyl zirconium $\eta^4$-1-phenyl-1,3-pentadiene;
diphenylamidoborane-bis-$\eta^5$-cyclopentadienyl zirconium $\eta^5$-1,3-pentadiene;
diphenylamidoborane-bis-$\eta^5$-n-butylcyclopentadienyl zirconium dichloride;
diphenylamidoborane-bis-$\eta^5$-n-butylcyclopentadienyl zirconium dimethyl;
diphenylamidoborane-bis-$\eta^5$-n-butylcyclopentadienyl zirconium bis-dimethylamide;
diphenylamidoborane-bis-$\eta^5$-n-butylcyclopentadienyl zirconium 2-methyl-1,3-butadiene;
diphenylamidoborane-bis-$\eta^5$-n-butylcyclopentadienyl zirconium 2,3-dimethyl-1,3-butadiene;
diphenylamidoborane-bis-$\eta^5$-n-butylcyclopentadienyl zirconium 2-N,N-dimethylaminobenzyl;
diphenylamidoborane-bis-$\eta^5$-n-butylcyclopentadienyl zirconium allyl;
diphenylamidoborane-bis-$\eta^5$-n-butylcyclopentadienyl zirconium $\eta^4$-1,4-diphenyl-1,3-butadiene;
diphenylamidoborane-bis-$\eta^5$-n-butylcyclopentadienyl zirconium $\eta^4$-2,4-hexadiene;
diphenylamidoborane-bis-$\eta^5$-n-butylcyclopentadienyl zirconium $\eta^4$-1,4-dinaphthyl-1,3-butadiene;
diphenylamidoborane-bis-$\eta^5$-n-butylcyclopentadienyl zirconium $\eta^4$-1-phenyl-1,3-pentadiene;
diphenylamidoborane-bis-$\eta^5$-n-butylcyclopentadienyl zirconium $\eta^5$-1,3-pentadiene;
diphenylamidoborane-bis-$\eta^5$-inden-1-ylzirconium dichloride;
diphenylamidoborane-bis-$\eta^5$-inden-1-ylzirconium dimethyl;
diphenylamidoborane-bis-$\eta^5$-inden-1-ylzirconium bis-dimethylamide;
diphenylamidoborane-bis-$\eta^5$-inden-1-ylzirconium 2-methyl-1,3-butadiene;
diphenylamidoborane-bis-$\eta^5$-inden-1-ylzirconium 2,3-dimethyl-1,3-butadiene;
diphenylamidoborane-bis-$\eta^5$-inden-1-ylzirconium 2-N,N-dimethylaminobenzyl;

diphenylamidoborane-bis-η⁵-inden-1-ylzirconium allyl;
diphenylamidoborane-bis-η⁵-inden-1-ylzirconium η⁴-1,4-diphenyl-1,3-butadiene;
diphenylamidoborane-bis-η⁵-inden-1-ylzirconium η⁴-2,4-hexadiene;
diphenylamidoborane-bis-η⁵-inden-1-ylzirconium η⁴-1,4-dinaphthyl-1,3-butadiene;
diphenylamidoborane-bis-η⁵-inden-1-ylzirconium η⁴-1-phenyl-1,3-pentadiene;
diphenylamidoborane-bis-η⁵-inden-1-ylzirconium η⁴-1,3-pentadiene;
diphenylamidoborane-bis-η⁵-(2-methylinden-1-yl)zirconium dichloride;
diphenylamidoborane-bis-η⁵-(2-methylinden-1-yl)zirconium dimethyl;
diphenylamidoborane-bis-η⁵-(2-methylinden-1-yl)zirconium bis-dimethylamide;
diphenylamidoborane-bis-η⁵-(2-methylinden-1-yl)zirconium 2-methyl-1,3-butadiene;
diphenylamidoborane-bis-η⁵-(2-methylinden-1-yl)zirconium 2,3-dimethyl-1,3-butadiene;
diphenylamidoborane-bis-η⁵-(2-methylinden-1-yl)zirconium 2-N,N-dimethylaminobenzyl;
diphenylamidoborane-bis-η⁵-(2-methylinden-1-yl)zirconium allyl;
diphenylamidoborane-bis-η⁵-(2-methylinden-1-yl)zirconium η⁴-1,4-diphenyl-1,3-butadiene;
diphenylamidoborane-bis-η⁵-(2-methylinden-1-yl)zirconium η⁴-2,4-hexadiene;
diphenylamidoborane-bis-η⁵-(2-methylinden-1-yl)zirconium η⁴-1,4-dinaphthyl-1,3-butadiene;
diphenylamidoborane-bis-η⁵-(2-methylinden-1-yl)zirconium η⁴-1-phenyl-1,3-pentadiene;
diphenylamidoborane-bis-η⁵-(2-methylinden-1-yl)zirconium η⁴-1,3-pentadiene;
diphenylamidoborane-bis-η⁵-(2-methyl-4-phenylinden-1-yl)zirconium dichloride;
diphenylamidoborane-bis-η⁵-(2-methyl-4-phenylinden-1-yl)zirconium dimethyl;
diphenylamidoborane-bis-η⁵-(2-methyl-4-phenylinden-1-yl)zirconium bis-dimethylamide;
diphenylamidoborane-bis-η⁵-(2-methyl-4-phenylinden-1-yl)zirconium 2-methyl-1,3-butadiene;
diphenylamidoborane-bis-η⁵-(2-methyl-4-phenylinden-1-yl)zirconium 2,3-dimethyl-1,3-butadiene;
diphenylamidoborane-bis-η⁵-(2-methyl-4-phenylinden-1-yl)zirconium 2-N,N-dimethylaminobenzyl;
diphenylamidoborane-bis-η⁵-(2-methyl-4-phenylinden-1-yl)zirconium allyl;
diphenylamidoborane-bis-η⁵-(2-methyl-4-phenylinden-1-yl)zirconium η⁴-1,3-diphenyl-1,3-butadiene;
diphenylamidoborane-bis-η⁵-(2-methyl-4-phenylinden-1-yl)zirconium η⁴-2,4-hexadiene;
diphenylamidoborane-bis-η⁵-(2-methyl-4-phenylinden-1-yl)zirconium η⁴-1,4-dinaphhthyl-1,3-butadiene;
diphenylamidoborane-bis-η⁵-(2-methyl-4-phenylinden-1-yl)zirconium η⁴-1-phenyl-1,3-pentadiene;
diphenylamidoborane-bis-η⁵-(2-methyl-4-phenylinden-1-yl)zirconium η⁴-1,3-pentadiene;
diphenylamidoborane-bis-η⁵-(2-ethyl-4-phenylinden-1-yl)zirconium dichloride;
diphenylamidoborane-bis-η⁵-(2-ethyl-4-phenylinden-1-yl)zirconium dimethyl;
diphenylamidoborane-bis-η⁵-(2-ethyl-4-phenylinden-1-yl)zirconium bis-dimethylamide;
diphenylamidoborane-bis-η⁵-(2-ethyl-4-phenylinden-1-yl)zirconium 2-methyl-1,3-butadiene;
diphenylamidoborane-bis-η⁵-(2-ethyl-4-phenylinden-1-yl)zirconium 2,3-dimethyl-1,3-butadiene;
diphenylamidoborane-bis-η⁵-(2-ethyl-4-phenylinden-1-yl)zirconium 2-N,N-dimethylaminobenzyl;
diphenylamidoborane-bis-η⁵-(2-ethyl-4-phenylinden-1-yl)zirconium allyl;
diphenylamidoborane-bis-η⁵-(2-ethyl-4-phenylinden-1-yl)zirconium η⁴-1,4-diphenyl-1,3-butadiene;
diphenylamidoborane-bis-η⁵-(2-ethyl-4-phenylinden-1-yl)zirconium η⁴-2,4-hexadiene;
diphenylamidoborane-bis-η⁵-(2-ethyl-4-phenylinden-1-yl)zirconium η⁴-1,4-dinaphthyl-1,3-butadiene;
diphenylamidoborane-bis-η⁵-(2-ethyl-4-phenylinden-1-yl)zirconium η⁴-1-phenyl-1,3-pentadiene;
diphenylamidoborane-bis-η⁵-(2-ethyl-4-phenylinden-1-yl)zirconium η⁴-1,3-pentadiene;
diphenylamidoborane-bis-η⁵-(2-isopropyl-4-phenylinden-1-yl)zirconium dichloride;
diphenylamidoborane-bis-η⁵-(2-isopropyl-4-phenylinden-1-yl)zirconium dimethyl;
diphenylamidoborane-bis-η⁵-(2-isopropyl-4-phenylinden-1-yl)zirconium bis-dimethylamide;
diphenylamidoborane-bis-η⁵-(2-isopropyl-4-phenylinden-1-yl)zirconium 2-methyl-1,3-butadiene;
diphenylamidoborane-bis-η⁵-(2-isopropyl-4-phenylinden-1-yl)zirconium 2,3-dimethyl-1,3-butadiene;
diphenylamidoborane-bis-η⁵-(2-isopropyl-4-phenylinden-1-yl)zirconium 2-N,N-dimethylaminobenzyl;
diphenylamidoborane-bis-η⁵-(2-isopropyl-4-phenylinden-1-yl)zirconium allyl;
diphenylamidoborane-bis-η⁵-(2-isopropyl-4-phenylinden-1-yl)zirconium η⁴-1,4-diphenyl-1,3-butadiene;
diphenylamidoborane-bis-η⁵-(2-isopropyl-4-phenylinden-1-yl)zirconium η⁴-2,4-hexadiene;
diphenylamidoborane-bis-η⁵-(2-isopropyl-4-phenylinden-1-yl)zirconium η⁴-1,4-dinaphthyl-1,3-butadiene;
diphenylamidoborane-bis-η⁵-(2-isopropyl-4-phenylinden-1-yl)zirconium η⁴-1-phenyl-1,3-pentadiene;
diphenylamidoborane-bis-η⁵-(2-isopropyl-4-phenylinden-1-yl)zirconium η⁴-1,3-pentadiene;
diphenylamidoborane-bis-η⁵-(2-methyl-4-naphthylinden-1-yl)zirconium dichloride;
diphenylamidoborane-bis-η⁵-(2-methyl-4-naphthylinden-1-yl)zirconium dimethyl;
diphenylamidoborane-bis-η⁵-(2-methyl-4-naphthylinden-1-yl)zirconium bis-dimethylamide;
diphenylamidoborane-bis-η⁵-(2-methyl-4-naphthylinden-1-yl)zirconium 2-methyl-1,3-butadiene;
diphenylamidoborane-bis-η⁵-(2-methyl-4-naphthylinden-1-yl)zirconium 2,3-dimethyl-1,3-butadiene;
diphenylamidoborane-bis-η⁵-(2-methyl-4-naphthylinden-1-yl)zirconium 2-N,N-dimethylaminobenzyl;
diphenylamidoborane-bis-η⁵-(2-methyl-4-naphthylinden-1-yl)zirconium allyl;
diphenylamidoborane-bis-η⁵-(2-methyl-4-naphthylinden-1-yl)zirconium η⁴-1,4-diphenyl-1,3-butadiene;
diphenylamidoborane-bis-η⁵-(2-methyl-4-naphthylinden-1-yl)zirconium η⁴-2,4-hexadiene;
diphenylamidoborane-bis-η⁵-(2-methyl-4-naphthylinden-1-yl)zirconium η⁴-1,4-dinaphthyl-1,3-butadiene;
diphenylamidoborane-bis-η⁵-(2-methyl-4-naphthylinden-1-yl)zirconium η⁴-1-phenyl-1,3-pentadiene;
diphenylamidoborane-bis-η⁵-(2-methyl-4-naphthylinden-1-yl)zirconium η⁴-1,3-pentadiene;
diphenylamidoborane-bis-η⁵-(2-methyl-4-bis(3,5-trifluoromethyl)phenylinden-1-yl)zirconium dichlroide;
diphenylamidoborane-bis-η⁵-(2-methyl-4-bis(3,5-trifluoromethyl)phenylinden-1-yl)zirconium dimethyl;

diphenylamidoborane-bis-η⁵-(2-methyl-4-bis(3,5-trifluoromethyl)phenylinden-1-yl)zirconium bis-dimethylamide;
diphenylamidoborane-bis-η⁵-(2-methyl-4-bis(3,5-trifluoromethyl)phenylinden-1-yl)zirconium 2-methyl-1,3-butadiene;
diphenylamidoborane-bis-η⁵-(2-methyl-4-bis(3,5-trifluoromethyl)phenylinden-1-yl)zirconium 2,3-dimethyl-1,3-butadiene;
diphenylamidoborane-bis-η⁵-(2-methyl-4-bis(3,5-trifluoromethyl)phenylinden-1-yl)zirconium 2-N,N-dimethylaminobenzyl;
diphenylamidoborane-bis-η⁵-(2-methyl-4-bis(3,5-trifluoromethyl)phenylinden-1-yl)zirconium allyl;
diphenylamidoborane-bis-η⁵-(2-methyl-4-bis(3,5-trifluoromethyl)phenylinden-1-yl)zirconium η⁴-1,4-diphenyl-1,3-butadiene;
diphenylamidoborane-bis-η⁵-(2-methyl-4-bis(3,5-trifluoromethyl)phenylinden-1-yl)zirconium η⁴-2,4-hexadiene;
diphenylamidoborane-bis-η⁵-(2-methyl-4-bis(3,5-trifluoromethyl)phenylinden-1-yl)zirconium η⁴-1,4-dinaphthyl-1,3-butadiene;
diphenylamidoborane-bis-η⁵-(2-methyl-4-bis(3,5-trifluoromethyl)phenylinden-1-yl)zirconium η⁴-1-phenyl-1,3-pentadiene;
diphenylamidoborane-bis-η⁵-(2-methyl-4-bis(3,5-trifluoromethyl)phenylinden-1-yl)zirconium η⁴-1,3-pentadiene;
diphenylamidoborane-bis-η⁵-(2-ethyl-4-bis(3,5-trifluoromethyl)phenylinden-1-yl)zirconium dichloride;
diphenylamidoborane-bis-η⁵-(2-ethyl-4-bis(3,5-trifluoromethyl)phenylinden-1-yl)zirconium dimethyl;
diphenylamidoborane-bis-η⁵-(2-ethyl-4-bis(3,5-trifluoromethyl)phenylinden-1-yl)zirconium bis-dimethylamide;
diphenylamidoborane-bis-η⁵-(2-ethyl-4-bis(3,5-trifluoromethyl)phenylinden-1-yl)zirconium 2-methyl-1,3-butadiene;
diphenylamidoborane-bis-η⁵-(2-ethyl-4-bis(3,5-trifluoromethyl)phenylinden-1-yl)zirconium 2,3-dimethyl-1,3-butadiene;
diphenylamidoborane-bis-η⁵-(2-ethyl-4-bis(3,5-trifluoromethyl)phenylinden-1-yl)zirconium 2-N,N-dimethylaminobenzyl;
diphenylamidoborane-bis-η⁵-(2-ethyl-4-bis(3,5-trifluoromethyl)phenylinden-1-yl)zirconium allyl;
diphenylamidoborane-bis-η⁵-(2-ethyl-4-bis(3,5-trifluoromethyl)phenylinden-1-yl)zirconium η⁴-1,4-diphenyl-1,3-butadiene;
diphenylamidoborane-bis-η⁵-(2-ethyl-4-bis(3,5-trifluoromethyl)phenylinden-1-yl)zirconium η⁴-2,4-hexadiene;
diphenylamidoborane-bis-η⁵-(2-ethyl-4-bis(3,5-trifluoromethyl)phenylinden-1-yl)zirconium η⁴-1,4-dinaphthyl-1,3-butadiene;
diphenylamidoborane-bis-η⁵-(2-ethyl-4-bis(3,5-trifluoromethyl)phenylinden-1-yl)zirconium η⁴-1-phenyl-1,3-pentadiene;
diphenylamidoborane-bis-η⁵-(2-ethyl-4-bis(3,5-trifluoromethyl)phenylinden-1-yl)zirconium η⁴-1,3-pentadiene;
diphenylamidoborane-bis-η⁵-(2-isopropyl-4-bis(3,5-trifluoromethyl)phenylinden-1-yl)zirconium dichloride;
diphenylamidoborane-bis-η⁵-(2-isopropyl-4-bis(3,5-trifluoromethyl)phenylinden-1-yl)zirconium dimethyl;
diphenylamidoborane-bis-η⁵-(2-isopropyl-4-bis(3,5-trifluoromethyl)phenylinden-1-yl)zirconium bis-dimethylamide;
diphenylamidoborane-bis-η⁵-(2-isopropyl-4-bis(3,5-trifluoromethyl)phenylinden-1-yl)zirconium 2-methyl-1,3-butadiene;
diphenylamidoborane-bis-η⁵-(2-isopropyl-4-bis(3,5-trifluoromethyl)phenylinden-1-yl)zirconium 2,3-dimethyl-1,3-butadiene;
diphenylamidoborane-bis-η⁵-(2-isopropyl-4-bis(3,5-trifluoromethyl)phenylinden-1-yl)zirconium 2-N,N-dimethylaminobenzyl;
diphenylamidoborane-bis-η⁵-(2-isopropyl-4-bis(3,5-trifluoromethyl)phenylinden-1-yl)zirconium allyl;
diphenylamidoborane-bis-η⁵-(2-isopropyl-4-bis(3,5-trifluoromethyl)phenylinden-1-yl)zirconium η⁴-1,4-diphenyl-1,3-butadiene;
diphenylamidoborane-bis-η⁵-(2-isopropyl-4-bis(3,5-trifluoromethyl)phenylinden-1-yl)zirconium η⁴-2,4-hexadiene;
diphenylamidoborane-bis-η⁵-(2-isopropyl-4-bis(3,5-trifluoromethyl)phenylinden-1-yl)zirconium η⁴-1,4-dinaphthyl-1,3-butadiene;
diphenylamidoborane-bis-η⁵-(2-isopropyl-4-bis(3,5-trifluoromethyl)phenylinden-1-yl)zirconium η⁴-1-phenyl-1,3-pentadiene;
diphenylamidoborane-bis-η⁵-(2-isopropyl-4-bis(3,5-trifluoromethyl)phenylinden-1-yl)zirconium η⁴-1,3-pentadiene;
diphenylamidoborane-bis-η⁵-(3-isopropylinden-1-yl)zirconium dichloride;
diphenylamidoborane-bis-η⁵-(3-isopropylinden-1-yl)zirconium dimethyl;
diphenylamidoborane-bis-η⁵-(3-isopropylinden-1-yl)zirconium bis-dimethylamide;
diphenylamidoborane-bis-η⁵-(3-isopropylinden-1-yl)zirconium 2-methyl-1,3-butadiene;
diphenylamidoborane-bis-η⁵-(3-isopropylinden-1-yl)zirconium 2,3-dimethyl-1,3-butadiene;
diphenylamidoborane-bis-η⁵-(3-isopropylinden-1-yl)zirconium 2-N,N-dimethylaminobenzyl;
diphenylamidoborane-bis-η⁵-(3-isopropylinden-1-yl)zirconium allyl;
diphenylamidoborane-bis-η⁵-(3-isopropylinden-1-yl)zirconium η⁴-1,4-diphenyl-1,3-butadiene;
diphenylamidoborane-bis-η⁵-(3-isopropylinden-1-yl)zirconium η⁴-2,4-hexadiene;
diphenylamidoborane-bis-η⁵-(3-isopropylinden-1-yl)zirconium η⁴-1,4-dinaphthyl-1,3-butadiene;
diphenylamidoborane-bis-η⁵-(3-isopropylinden-1-yl)zirconium η⁴-1-phenyl-1,3-pentadiene;
diphenylamidoborane-bis-η⁵-(3-isopropylinden-1-yl)zirconium η⁴-1,3-pentadiene;
diphenylamidoborane-bis-η⁵-(3-t-butylinden-1-yl)zirconium dichloride
diphenylamidoborane-bis-η⁵-(3-t-butylinden-1-yl)zirconium dimethyl;
diphenylamidoborane-bis-η⁵-(3-t-butylinden-1-yl)zirconium bis-dimethylamide;
diphenylamidoborane-bis-η⁵-(3-t-butylinden-1-yl)zirconium 2-methyl-1,3-butadiene;
diphenylamidoborane-bis-η⁵-(3-t-butylinden-1-yl)zirconium 2,3-dimethyl-1,3-butadiene;
diphenylamidoborane-bis-η⁵-(3-t-butylinden-1-yl)zirconium 2-N,N-dimethylaminobenzyl;
diphenylamidoborane-bis-η⁵-(3-t-butylinden-1-yl)zirconium allyl;
diphenylamidoborane-bis-η⁵-(3-t-butylinden-1-yl)zirconium η⁴-1,4-diphenyl-1,3-butadiene;
diphenylamidoborane-bis-η⁵-(3-t-butylinden-1-yl)zirconium η⁴-2,4-hexadiene;

diphenylamidoborane-bis-η⁵-(3-t-butylinden-1-yl)zirconium η⁴-1,4-dinaphthyl-1,3-butadiene;
diphenylamidoborane-bis-η⁵-(3-t-butylinden-1-yl)zirconium η⁴-1-phenyl-1,3-pentadiene;
diphenylamidoborane-bis-η⁵-(3-t-butylinden-1-yl)zirconium η⁴-1,3-pentadiene;
bis(trimethylsilyl)amidoborane-bis-η⁵-cyclopentadienylzirconium dichloride;
bis(trimethylsilyl)amidoborane-bis-η⁵-cyclopentadienylzirconium dimethyl;
bis(trimethylsilyl)amidoborane-bis-η⁵-cyclopentadienylzirconium bis-dimethylamide;
bis(trimethylsilyl)amidoborane-bis-η⁵-cyclopentadienylzirconium 2-methyl-1,3-butadiene;
bis(trimethylsilyl)amidoborane-bis-η⁵-cyclopentadienylzirconium 2,3-dimethyl-1,3-butadiene;
bis(trimethylsilyl)amidoborane-bis-η⁵-cyclopentadienylzirconium 2-N,N-dimethylaminobenzyl;
bis(trimethylsilyl)amidoborane-bis-η⁵-cyclopentadienylzirconium allyl;
bis(trimethylsilyl)amidoborane-bis-η⁵-cyclopentadienylzirconium η⁴-1,4-diphenyl-1,3-butadiene;
bis(trimethylsilyl)amidoborane-bis-η⁵-cyclopentadienylzirconium η⁴-2,4-hexadiene;
bis(trimethylsilyl)amidoborane-bis-η⁵-cyclopentadienylzirconium η⁴-1,4-dinaphthyl-1,3-butadiene;
bis(trimethylsilyl)amidoborane-bis-η⁵-cyclopentadienylzirconium η⁴-1-phenyl-1,3-pentadiene;
bis(trimethylsilyl)amidoborane-bis-η⁵-cyclopentadienylzirconium η⁵-1,3-pentadiene;
bis(trimethylsilyl)amidoborane-bis-η⁵-inden-1-ylzirconium dichloride;
bis(trimethylsilyl)amidoborane-bis-η⁵-inden-1-ylzirconium dimethyl;
bis(trimethylsilyl)amidoborane-bis-η⁵-inden-1-ylzirconium bis-dimethylamide;
bis(trimethylsilyl)amidoborane-bis-η⁵-inden-1-ylzirconium 2-methyl-1,3-butadiene;
bis(trimethylsilyl)amidoborane-bis-η⁵-inden-1-ylzirconium 2,3-dimethyl-1,3-butadiene;
bis(trimethylsilyl)amidoborane-bis-η⁵-inden-1-ylzirconium 2-N,N-dimethylaminobenzyl;
bis(trimethylsilyl)amidoborane-bis-η⁵-inden-1-ylzirconium allyl;
bis(trimethylsilyl)amidoborane-bis-η⁵-inden-1-ylzirconium η⁴-1,4-diphenyl-1,3-butadiene;
bis(trimethylsilyl)amidoborane-bis-η⁵-inden-1-ylzirconium η⁴-2,4-hexadiene;
bis(trimethylsilyl)amidoborane-bis-η⁵-inden-1-ylzirconium η⁴-1,4-dinaphthyl-1,3-butadiene;
bis(trimethylsilyl)amidoborane-bis-η⁵-inden-1-ylzirconium η⁴-1-phenyl-1,3-pentadiene;
bis(trimethylsilyl)amidoborane-bis-η⁵-inden-1-ylzirconium η⁴-1,3-pentadiene;
bis(trimethylsilyl)amidoborane-bis-η⁵-(2-methylinden-1-yl)zirconium dichloride;
bis(trimethylsilyl)amidoborane-bis-η⁵-(2-methylinden-1-yl)zirconium dimethyl
bis(trimethylsilyl)amidoborane-bis-η⁵-(2-methylinden-1-yl)zirconium bis-dimethylamide;
bis(trimethylsilyl)amidoborane-bis-η⁵-(2-methylinden-1-yl)zirconium 2-methyl-1,3-butadiene;
bis(trimethylsilyl)amidoborane-bis-η⁵-(2-methylinden-1-yl)zirconium 2,3-dimethyl-1,3-butadiene;
bis(trimethylsilyl)amidoborane-bis-η⁵-(2-methylinden-1-yl)zirconium 2-N,N-dimethylaminobenzyl;
bis(trimethylsilyl)amidoborane-bis-η⁵-(2-methylinden-1-yl)zirconium allyl;
bis(trimethylsilyl)amidoborane-bis-η⁵-(2-methylinden-1-yl)zirconium η⁴-1,4-diphenyl-1,3-butadiene;
bis(trimethylsilyl)amidoborane-bis-η⁵-(2-methylinden-1-yl)zirconium η⁴-2,4-hexadiene;
bis(trimethylsilyl)amidoborane-bis-η⁵-(2-methylinden-1-yl)zirconium η⁴-1,4-dinaphthyl-1,3-butadiene;
bis(trimethylsilyl)amidoborane-bis-η⁵-(2-methylinden-1-yl)zirconium η⁴-1-phenyl-1,3-pentadiene;
bis(trimethylsilyl)amidoborane-bis-η⁵-(2-methylinden-1-yl)zirconium η⁴-1,3-pentadiene;
bis(trimethylsilyl)amidoborane-bis-η⁵-(2-methyl-4-phenylinden-1-yl)zirconium dichloride;
bis(trimethylsilyl)amidoborane-bis-η⁵-(2-methyl-4-phenylinden-1-yl)zirconium dimethyl;
bis(trimethylsilyl)amidoborane-bis-η⁵-(2-methyl-4-phenylinden-1-yl)zirconium bis-dimethylamide;
bis(trimethylsilyl)amidoborane-bis-η⁵-(2-methyl-4-phenylinden-1-yl)zirconium 2-methyl-1,3-butadiene;
bis(trimethylsilyl)amidoborane-bis-η⁵-(2-methyl-4-phenylinden-1-yl)zirconium 2,3-dimethyl-1,3-butadiene;
bis(trimethylsilyl)amidoborane-bis-η⁵-(2-methyl-4-phenylinden-1-yl)zirconium 2-N,N-dimethylaminobenzyl;
bis(trimethylsilyl)amidoborane-bis-η⁵-(2-methyl-4-phenylinden-1-yl)zirconium allyl;
bis(trimethylsilyl)amidoborane-bis-η⁵-(2-methyl-4-phenylinden-1-yl)zirconium η⁴-1,4-diphenyl-1,3-butadiene;
bis(trimethylsilyl)amidoborane-bis-η⁵-(2-methyl-4-phenylinden-1-yl)zirconium η⁴-2,4-hexadiene;
bis(trimethylsilyl)amidoborane-bis-η⁵-(2-methyl-4-phenylinden-1-yl)zirconium η⁴-1,4-dinaphthyl-1,3-butadiene;
bis(trimethylsilyl)amidoborane-bis-η⁵-(2-methyl-4-phenylinden-1-yl)zirconium η⁴-1-phenyl-1,3-pentadiene;
bis(trimethylsilyl)amidoborane-bis-η⁵-(2-methyl-4-phenylinden-1-yl)zirconium η⁴-1,3-pentadiene;
bis(trimethylsilyl)amidoborane-bis-η⁵-(2-methyl-4-naphthylinden-1-yl)zirconium dichloride;
bis(trimethylsilyl)amidoborane-bis-η⁵-(2-methyl-4-naphthylinden-1-yl)zirconium dimethyl;
bis(trimethylsilyl)amidoborane-bis-η⁵-(2-methyl-4-naphthylinden-1-yl)zirconium bis-dimethylamide;
bis(trimethylsilyl)amidoborane-bis-η⁵-(2-methyl-4-naphthylinden-1-yl)zirconium 2-methyl-1,3-butadiene;
bis(trimethylsilyl)amidoborane-bis-η⁵-(2-methyl-4-naphthylinden-1-yl)zirconium 2,3-dimethyl-1,3-butadiene;
bis(trimethylsilyl)amidoborane-bis-η⁵-(2-methyl-4-naphthylinden-1-yl)zirconium 2-N,N-dimethylaminobenzyl;
bis(trimethylsilyl)amidoborane-bis-η⁵-(2-methyl-4-naphthylinden-1-yl)zirconium allyl;
bis(trimethylsilyl)amidoborane-bis-η⁵-(2-methyl-4-naphthylinden-1-yl)zirconium η⁴-1,4-diphenyl-1,3-butadiene;
bis(trimethylsilyl)amidoborane-bis-η⁵-(2-methyl-4-naphthylinden-1-yl)zirconium η⁴-2,4-hexadiene;
bis(trimethylsilyl)amidoborane-bis-η⁵-(2-methyl-4-naphthylinden-1-yl)zirconium η⁴-1,4-dinapthyl-1,3-batadiene;
bis(trimethylsilyl)amidoborane-bis-η⁵-(2-methyl-4-naphthylinden-1-yl)zirconium η⁴-1-phenyl-1,3-pentadiene;
bis(trimethylsilyl)amidoborane-bis-η⁵-(2-methyl-4-naphthylinden-1-yl)zirconium η⁴-12,3-pentadiene;

bis(trimethylsilyl)amidoborane-bis-η⁵-(3-isopropylinden-1-yl)zirconium dichloride;
bis(trimethylsilyl)amidoborane-bis-η⁵-(3-isopropylinden-1-yl)zirconium dimethyl;
bis(trimethylsilyl)amidoborane-bis-η⁵-(3-isopropylinden-1-yl)zirconium bis-dimethylamide;
bis(trimethylsilyl)amidoborane-bis-η⁵-(3-isopropylinden-1-yl)zirconium 2-methyl-1,3-butadiene;
bis(trimethylsilyl)amidoborane-bis-η⁵-(3-isopropylinden-1-yl)zirconium 2,3-dimethyl-1,3-butadiene;
bis(trimethylsilyl)amidoborane-bis-η⁵-(3-isopropylinden-1-yl)zirconium 2-N,N-dimethylaminobenzyl;
bis(trimethylsilyl)amidoborane-bis-η⁵-(3-isopropylinden-1-yl)zirconium allyl;
bis(trimethylsilyl)amidoborane-bis-η⁵-(3-isopropylinden-1-yl)zirconium η⁴-1,4-diphenyl-1,3-butadiene;
bis(trimethylsilyl)amidoborane-bis-η⁵-(3-isopropylinden-1-yl)zirconium η⁴-2,4-hexadiene;
bis(trimethylsilyl)amidoborane-bis-η⁵-(3-isopropylinden-1-yl)zirconium η⁴-1,4-dinaphthyl-1,3-butadiene;
bis(trimethylsilyl)amidoborane-bis-η⁵-(3-isopropylinden-1-yl)zirconium η⁴-1-phenyl-1,3-pentadiene;
bis(trimethylsilyl)amidoborane-bis-η⁵-(3-isopropylinden-1-yl)zirconium η⁴-1,3-pentadiene;
bis(trimethylsilyl)amidoborane-bis-η⁵-(3-t-butylinden-1-yl)zirconium dichloride;
bis(trimethylsilyl)amidoborane-bis-η⁵-(3-t-butylinden-1-yl)zirconium dimethyl;
bis(trimethylsilyl)amidoborane-bis-η⁵-(3-t-butylinden-1-yl)zirconium bis-dimethylamide;
bis(trimethylsilyl)amidoborane-bis-η⁵-(3-t-butylinden-1-yl)zirconium 2-methyl-1,3-butadiene;
bis(trimethylsilyl)amidoborane-bis-η⁵-(3-t-butylinden-1-yl)zirconium 2,3-dimethyl-1,3-butadiene;
bis(trimethylsilyl)amidoborane-bis-η⁵-(3-t-butylinden-1-yl)zirconium 2-N,N-dimethylaminobenzyl;
bis(trimethylsilyl)amidoborane-bis-η⁵-(3-t-butylinden-1-yl)zirconium allyl;
bis(trimethylsilyl)amidoborane-bis-η⁵-(3-t-butylinden-1-yl)zirconium η⁴-1,4-diphenyl-1,3-butadiene;
bis(trimethylsilyl)amidoborane-bis-η⁵-(3-t-butylinden-1-yl)zirconium η⁴-2,4-hexadiene;
bis(trimethylsilyl)amidoborane-bis-η⁵-(3-t-butylinden-1-yl)zirconium η⁴-1,4-dinaphthyl-1,3-butadiene;
bis(trimethylsilyl)amidoborane-bis-η⁵-(3-t-butylinden-1-yl)zirconium η⁴-1-phenyl-1,3-pentadiene;
bis(trimethylsilyl)amidoborane-bis-η⁵-(3-t-butylinden-1-yl)zirconium η⁴-1,3-pentadiene;
bis(diisopropylamido)diborane-1,2-bis-η⁵-(2-methyl-4-phenylinden-1-yl)zirconium dichloride;
bis(diisopropylamido)diborane-1,2-bis-η⁵-(2-methyl-4-phenylinden-1-yl)zirconium dimethyl;
bis(diisopropylamido)diborane-1,2-bis-η⁵-(2-methyl-4-phenylinden-1-yl)zirconium bis-dimethylamide;
bis(diisopropylamido)diborane-1,2-bis-η⁵-(2-methyl-4-phenylinden-1-yl)zirconium 2-methyl-1,3-butadiene;
bis(diisopropylamido)diborane-1,2-bis-η⁵-(2-methyl-4-phenylinden-1-yl)zirconium 2,3-dimethyl-1,3-butadiene;
bis(diisopropylamido)diborane-1,2-bis-η⁵-(2-methyl-4-phenylinden-1-yl)zirconium 2-N,N-dimethylaminobenzyl;
bis(diisopropylamido)diborane-1,2-bis-η⁵-(2-methyl-4-phenylinden-1-yl)zirconium allyl;
bis(diisopropylamido)diborane-1,2-bis-η⁵-(2-methyl-4-phenylinden-1-yl)zirconium η⁴-1,4-diphenyl-1,3-butadiene;
bis(diisopropylamido)diborane-1,2-bis-η⁵-(2-methyl-4-phenylinden-1-yl)zirconium η⁴-2,4-hexadiene;
bis(diisopropylamido)diborane-1,2-bis-η⁵-(2-methyl-4-phenylinden-1-yl)zirconium η⁴-1,3-butadiene;
bis(diisopropylamido)diborane-1,2-bis-η⁵-(2-methyl-4-phenylinden-1-yl)zirconium η⁴-1-phenyl-1,3-pentadiene;
bis(diisopropylamido)diborane-1,2-bis-η⁵-(2-methyl-4-phenylinden-1-yl)zirconium η⁴-1,3-pentadiene;
dimethylamidoborane-bis-η⁵-cyclopentadienyl hafnium dichloride;
dimethylamidoborane-bis-η⁵-cyclopentadienyl hafnium dimethyl;
dimethylamidoborane-bis-η⁵-cyclopentadienyl hafnium bis-dimethylamide;
dimethylamidoborane-bis-η⁵-cyclopentadienyl hafnium 2-methyl-1,3-butadiene;
dimethylamidoborane-bis-η⁵-cyclopentadienyl hafnium 2,3-dimethyl-1,3-butadiene;
dimethylamidoborane-bis-η⁵-cyclopentadienyl hafnium 2-N,N-dimethylaminobenzyl;
dimethylamidoborane-bis-η⁵-cyclopentadienyl hafnium allyl;
dimethylamidoborane-bis-η⁵-cyclopentadienyl hafnium η⁴-1,4-diphenyl-1,3-butadiene;
dimethylamidoborane-bis-η⁵-cyclopentadienyl hafnium η⁴-2,4-hexadiene;
dimethylamidoborane-bis-η⁵-cyclopentadienyl hafnium η⁴-1,4-dinaphthyl-1,3-butadiene;
dimethylamidoborane-bis-η⁵-cyclopentadienyl hafnium η⁴-1,3-pentadiene;
dimethylamidoborane-bis-η⁵-cyclopentadienyl hafnium η⁵-1,3-pentadiene;
dimethylamidoborane-bis-η⁵-butylcyclopentadienyl hafnium dichloride;
dimethylamidoborane-bis-η⁵-butylcyclopentadienyl hafnium dimethyl;
dimethylamidoborane-bis-η⁵-butylcyclopentadienyl hafnium bis-dimethylamide;
dimethylamidoborane-bis-η⁵-butylcyclopentadienyl hafnium 2-methyl-1,3-butadiene;
dimethylamidoborane-bis-η⁵-butylcyclopentadienyl hafnium 2,3-dimethyl-1,3-butadiene;
dimethylamidoborane-bis-η⁵-butylcyclopentadienyl hafnium 2-N,N-dimethylaminobenzyl;
dimethylamidoborane-bis-η⁵-butylcyclopentadienyl hafnium allyl;
dimethylamidoborane-bis-η⁵-butylcyclopentadienyl hafnium η⁴-1,4-diphenyl-1,3-butadiene;
dimethylamidoborane-bis-η⁵-butylcyclopentadienyl hafnium η⁴-2,4-hexadiene;
dimethylamidoborane-bis-η⁵-butylcyclopentadienyl hafnium η⁴-1,4-dinaphthyl-1,3-butadiene;
dimethylamidoborane-bis-η⁵-butylcyclopentadienyl hafnium η⁴-1-phenyl-1,3-pentadiene;
dimethylamidoborane-bis-η⁵-butylcyclopentadienyl hafnium η⁵-1,3-pentadiene;
dimethylamidoborane-bis-η⁵-inden-1-ylhafnium dichloride;
dimethylamidoborane-bis-η⁵-inden-1-ylhafnium bis-dimethylamide;
dimethylamidoborane-bis-η⁵-inden-1-ylhafnium 2-methyl-1,3-butadiene;
dimethylamidoborane-bis-η⁵-inden-1-ylhafnium 2,3-dimethyl-1,3-butadiene;
dimethylamidoborane-bis-η⁵-inden-1-ylhafnium 2-N,N-dimethylaminobenzyl;
dimethylamidoborane-bis-η⁵-inden-1-ylhafnium allyl;
dimethylamidoborane-bis-η⁵-inden-1-ylhafnium η⁴-1,4-diphenyl-1,3-butadiene;
dimethylamidoborane-bis-η⁵-inden-1-ylhafnium η⁴-2,4-hexadiene;

dimethylamidoborane-bis-$\eta^5$-inden-1-ylhafnium $\eta^4$-1,4-dinaphthyl-1,3-butadiene;
dimethylamidoborane-bis-$\eta^5$-inden-1-ylhafnium $\eta^4$-1-phenyl-1,3-pentadiene;
dimethylamidoborane-bis-$\eta^5$-inden-1-ylhafnium $\eta^4$-1,3-pentadiene;
dimethylamidoborane-bis-$\eta^5$-(2-methylinden-1-yl)hafnium dichloride;
dimethylamidoborane-bis-$\eta^5$-(2-methylinden-1-yl)hafnium dimethyl;
dimethylamidoborane-bis-$\eta^5$-(2-methylinden-1-yl)hafnium bis-dimethylamide;
dimethylamidoborane-bis-$\eta^5$-(2-methylinden-1-yl)hafnium 2-methyl-1,3-butadiene;
dimethylamidoborane-bis-$\eta^5$-(2-methylinden-1-yl)hafnium 2,3-dimethyl-1,3-butadiene;
dimethylamidoborane-bis-$\eta^5$-(2-methylinden-1-yl)hafnium 2-N,N-dimethylaminobenzyl;
dimethylamidoborane-bis-$\eta^5$-(2-methylinden-1-yl)hafnium allyl;
dimethylamidoborane-bis-$\eta^5$-(2-methylinden-1-yl)hafnium $\eta^4$-1,4-diphenyl-1,3-butadiene;
dimethylamidoborane-bis-$\eta^5$-(2-methylinden-1-yl)hafnium $\eta^4$-2,4-hexadiene;
dimethylamidoborane-bis-$\eta^5$-(2-methylinden-1-yl)hafnium $\eta^4$-1,4-dinaphthyl-1,3-butadiene;
dimethylamidoborane-bis-$\eta^5$-(2-methylinden-1-yl)hafnium $\eta^4$-1-phenyl-1,3-pentadiene;
dimethylamidoborane-bis-$\eta^5$-(2-methylinden-1-yl)hafnium $\eta^4$-1,3-pentadiene;
dimethylamidoborane-bis-$\eta^5$-(2-methyl-4-phenylinden-1-yl)hafnium dichloride;
dimethylamidoborane-bis-$\eta^5$-(2-methyl-4-phenylinden-1-yl)hafnium dimethyl;
dimethylamidoborane-bis-$\eta^5$-(2-methyl-4-phenylinden-1-yl)hafnium bis-dimethylamide;
dimethylamidoborane-bis-$\eta^5$-(2-methyl-4-phenylinden-1-yl)hafnium 2-methyl-1,3-butadiene;
dimethylamidoborane-bis-$\eta^5$-(2-methyl-4-phenylinden-1-yl)hafnium 2,3-dimethyl-1,3-butadiene;
dimethylamidoborane-bis-$\eta^5$-(2-methyl-4-phenylinden-1-yl)hafnium 2-N,N-dimethylaminobenzyl;
dimethylamidoborane-bis-$\eta^5$-(2-methyl-4-phenylinden-1-yl)hafnium allyl;
dimethylamidoborane-bis-$\eta^5$-(2-methyl-4-phenylinden-1-yl)hafnium $\eta^4$-1,4-diphenyl-1,3-butadiene;
dimethylamidoborane-bis-$\eta^5$-(2-methyl-4-phenylinden-1-yl)hafnium $\eta^4$-2,4-hexadiene;
dimethylamidoborane-bis-$\eta^5$-(2-methyl-4-phenylinden-1-yl)hafnium $\eta^4$-1,4-dinaphthyl-1,3-butadiene;
dimethylamidoborane-bis-$\eta^5$-(2-methyl-4-phenylinden-1-yl)hafnium $\eta^4$-1-phenyl-1,3-pentadiene;
dimethylamidoborane-bis-$\eta^5$-(2-methyl-4-phenylinden-1-yl)hafnium $\eta^4$-1,3-pentadiene;
dimethylamidoborane-bis-$\eta^5$-(2-methyl-4-naphthylinden-1-yl)hafnium dichloride;
dimethylamidoborane-bis-$\eta^5$-(2-methyl-4-naphthylinden-1-yl)hafnium dimethyl;
dimethylamidoborane-bis-$\eta^5$-(2-methyl-4-naphthylinden-1-yl)hafnium bis-dimethylamide;
dimethylamidoborane-bis-$\eta^5$-(2-methyl-4-naphthylinden-1-yl)hafnium 2-methyl-1,3-butadiene;
dimethylamidoborane-bis-$\eta^5$-(2-methyl-4-naphthylinden-1-yl)hafnium 2,3-dimethyl-1,3-butadiene;
dimethylamidoborane-bis-$\eta^5$-(2-methyl-4-naphthylinden-1-yl)hafnium 2-N,N-dimethylaminobenzyl;
dimethylamidoborane-bis-$\eta^5$-(2-methyl-4-naphthylinden-1-yl)hafnium allyl;
dimethylamidoborane-bis-$\eta^5$-(2-methyl-4-naphthylinden-1-yl)hafnium $\eta^4$-1,4-diphenyl-1,3-butadiene;
dimethylamidoborane-bis-$\eta^5$-(2-methyl-4-naphthylinden-1-yl)hafnium $\eta^4$-2,4-hexadiene;
dimethylamidoborane-bis-$\eta^5$-(2-methyl-4-naphthylinden-1-yl)hafnium $\eta^4$-1,4-dinaphthyl-1,3-butadiene;
dimethylamidoborane-bis-$\eta^5$-(2-methyl-4-naphthylinden-1-yl)hafnium $\eta^4$-1,3-pentadiene;
dimethylamidoborane-bis-$\eta^5$-(2-methyl-4-naphthylinden-1-yl)hafnium $\eta^4$-1,3-pentadiene;
dimethylamidoborane-bis-$\eta^5$-(3-isopropylinden-1-yl)hafnium dichloride;
dimethylamidoborane-bis-$\eta^5$-(3-isopropylinden-1-yl)hafnium dimethyl;
dimethylamidoborane-bis-$\eta^5$-(3-isopropylinden-1-yl)hafnium bis-dimethylamide;
dimethylamidoborane-bis-$\eta^5$-(3-isopropylinden-1-yl)hafnium 2-methyl-1,3-butadiene;
dimethylamidoborane-bis-$\eta^5$-(3-isopropylinden-1-yl)hafnium 2,3-dimethyl-1,3-butadiene;
dimethylamidoborane-bis-$\eta^5$-(3-isopropylinden-1-yl)hafnium 2-N,N-dimethylaminobenzyl;
dimethylamidoborane-bis-$\eta^5$-(3-isopropylinden-1-yl)hafnium allyl;
dimethylamidoborane-bis-$\eta^5$-(3-isopropylinden-1-yl)hafnium $\eta^4$-1,4-diphenyl-1,3-butadiene;
dimethylamidoborane-bis-$\eta^5$-(3-isopropylinden-1-yl)hafnium $\eta^4$-2,4-hexadiene;
dimethylamidoborane-bis-$\eta^5$-(3-isopropylinden-1-yl)hafnium $\eta^4$-1,4-dinaphthyl-1,3-butadiene;
dimethylamidoborane-bis-$\eta^5$-(3-isopropylinden-1-yl)hafnium $\eta^4$-1-phenyl-1,3-pentadiene;
dimethylamidoborane-bis-$\eta^5$-(3-isopropylinden-1-yl)hafnium $\eta^4$-1,3-pentadiene;
dimethylamidoborane-bis-$\eta^5$-(3-t-butylinden-1-yl)hafnium dichloride;
dimethylamidoborane-bis-$\eta^5$-(3-t-butylinden-1-yl)hafnium dimethyl;
dimethylamidoborane-bis-$\eta^5$-(3-t-butylinden-1-yl)hafnium bis-dimethylamide;
dimethylamidoborane-bis-$\eta^5$-(3-t-butylinden-1-yl)hafnium 2-methyl-1,3-butadiene;
dimethylamidoborane-bis-$\eta^5$-(3-t-butylinden-1-yl)hafnium 2,3-dimethyl-1,3-butadiene;
dimethylamidoborane-bis-$\eta^5$-(3-t-butylinden-1-yl)hafnium 2-N,N-dimethylaminobenzyl;
dimethylamidoborane-bis-$\eta^5$-(3-t-butylinden-1-yl)hafnium allyl;
dimethylamidoborane-bis-$\eta^5$-(3-t-butylinden-1-yl)hafnium $\eta^4$-1,4-diphenyl-1,3-butadiene;
dimethylamidoborane-bis-$\eta^5$-(3-t-butylinden-1-yl)hafnium $\eta^4$-2,4-hexadiene;
dimethylamidoborane-bis-$\eta^5$-(3-t-butylinden-1-yl)hafnium $\eta^4$-1,4-dinaphthyl-1,3-butadiene;
dimethylamidoborane-bis-$\eta^5$-(3-t-butylinden-1-yl)hafnium $\eta^4$-1-phenyl-1,3-pentadiene;
dimethylamidoborane-bis-$\eta^5$-(3-t-butylinden-1-yl)hafnium $\eta^4$-1,3-pentadiene;
diisopropylamidoborane-bis-$\eta^5$-cyclopentadienylhafnium dichloride;
diisopropylamidoborane-bis-$\eta^5$-cyclopentadienylhafnium dimethyl;
diisopropylamidoborane-bis-$\eta^5$-cyclopentadienylhafnium bis-dimethylamide;
diisopropylamidoborane-bis-$\eta^5$-cyclopentadienylhafnium 2-methyl-1,3-butadiene;
diisopropylamidoborane-bis-$\eta^5$-cyclopentadienylhafnium 2,3-dimethyl-1,3-butadiene;

diisopropylamidoborane-bis-η⁵-cyclopentadienylhafnium 2-N,N-dimethylaminobenzyl;
diisopropylamidoborane-bis-η⁵-cyclopentadienylhafnium allyl;
diisopropylamidoborane-bis-η⁵-cyclopentadienylhafnium η⁴-1,4-diphenyl-1,3-butadiene;
diisopropylamidoborane-bis-η⁵-cyclopentadienylhafnium η⁴-2,4-hexadiene;
diisopropylamidoborane-bis-η⁵-cyclopentadienylhafnium η⁴-1,4-dinaphthyl-1,3-butadiene;
diisopropylamidoborane-bis-η⁵-cyclopentadienylhafnium η⁴-1-phenyl-1,3-pentadiene;
diisopropylamidoborane-bis-η⁵-cyclopentadienylhafnium η⁵-1,3-pentadiene;
diisopropylamidoborane-bis-η⁵-inden-1-ylhafnium dichloride;
diisopropylamidoborane-bis-η⁵-inden-1-ylhafnium dimethyl;
diisopropylamidoborane-bis-η⁵-inden-1-ylhafnium bis-dimethylamide;
diisopropylamidoborane-bis-η⁵-inden-1-ylhafnium 2-methyl-1,3-butadiene;
diisopropylamidoborane-bis-η⁵-inden-1-ylhafnium 2,3-dimethyl-1,3-butadiene;
diisopropylamidoborane-bis-η⁵-inden-1-ylhafnium 2-N,N-dimethylaminobenzyl;
diisopropylamidoborane-bis-η⁵-inden-1-ylhafnium allyl;
diisopropylamidoborane-bis-η⁵-inden-1-ylhafnium η⁴-1,4-diphenyl-1,3-butadiene;
diisopropylamidoborane-bis-η⁵-inden-1-ylhafnium η⁴-2,4-hexadiene;
diisopropylamidoborane-bis-η⁵-inden-1-ylhafnium η⁴-1,4-dinaphthyl-1,3-butadiene;
diisopropylamidoborane-bis-η⁵-inden-1-ylhafnium η⁴-1-phenyl-1,3-pentadiene;
diisopropylamidoborane-bis-η⁵-inden-1-ylhafnium η⁴-1,3-pentadiene;
diisopropylamidoborane-bis-η⁵-(2-methylinden-1-yl)hafnium dichloride;
diisopropylamidoborane-bis-η⁵-(2-methylinden-1-yl)hafnium dimethyl;
diisopropylamidoborane-bis-η⁵-(2-methylinden-1-yl)hafnium bis-dimethylamide;
diisopropylamidoborane-bis-η⁵-(2-methylinden-1-yl)hafnium 2-methyl-1,3-butadiene;
diisopropylamidoborane-bis-η⁵-(2-methylinden-1-yl)hafnium 2,3-dimethyl-1,3-butadiene;
diisopropylamidoborane-bis-η⁵-(2-methylinden-1-yl)hafnium 2-N,N-dimethylaminobenzyl;
diisopropylamidoborane-bis-η⁵-(2-methylinden-1-yl)hafnium allyl;
diisopropylamidoborane-bis-η⁵-(2-methylinden-1-yl)hafnium η⁴-1,4-diphenyl-1,3-butadiene;
diisopropylamidoborane-bis-η⁵-(2-methylinden-1-yl)hafnium η⁴-2,4-hexadiene;
diisopropylamidoborane-bis-η⁵-(2-methylinden-1-yl)hafnium η⁴-1,4-dinaphthyl-1,3-butadiene;
diisopropylamidoborane-bis-η⁵-(2-methylinden-1-yl)hafnium η⁴-1-phenyl-1,3-pentadiene;
diisopropylamidoborane-bis-η⁵-(2-methylinden-1-yl)hafnium η⁴-1,3-pentadiene;
diisopropylamidoborane-bis-η⁵-(2-methyl-4-phenylinden-1-yl)hafnium dichloride;
diisopropylamidoborane-bis-η⁵-(2-methyl-4-phenylinden-1-yl)hafnium dimethyl;
diisopropylamidoborane-bis-η⁵-(2-methyl-4-phenylinden-1-yl)hafnium bis-dimethylamide;
diisopropylamidoborane-bis-η⁵-(2-methyl-4-phenylinden-1-yl)hafnium 2-methyl-1,3-butadiene;
diisopropylamidoborane-bis-η⁵-(2-methyl-4-phenylinden-1-yl)hafnium 2,3-dimethyl-1,3-butadiene;
diisopropylamidoborane-bis-η⁵-(2-methyl-4-phenylinden-1-yl)hafnium 2-N,N-dimethylaminobenzyl;
diisopropylamidoborane-bis-η⁵-(2-methyl-4-phenylinden-1-yl)hafnium allyl;
diisopropylamidoborane-bis-η⁵-(2-methyl-4-phenylinden-1-yl)hafnium η⁴-1,4-diphenyl-1,3-butadiene;
diisopropylamidoborane-bis-η⁵-(2-methyl-4-phenylinden-1-yl)hafnium η⁴-2,4-hexadiene;
diisopropylamidoborane-bis-η⁵-(2-methyl-4-phenylinden-1-yl)hafnium η⁴-1,4-dinaphthyl-1,3-butadiene;
diisopropylamidoborane-bis-η⁵-(2-methyl-4-phenylinden-1-yl)hafnium η⁴-1-phenyl-1,3-pentadiene;
diisopropylamidoborane-bis-η⁵-(2-methyl-4-phenylinden-1-yl)hafnium η⁴-1,3-pentadiene;
diisopropylamidoborane-bis-η⁵-(2-methyl-4-naphthylinden-1-yl)hafnium dichloride;
diisopropylamidoborane-bis-η⁵-(2-methyl-4-naphthylinden-1-yl)hafnium dimethyl;
diisopropylamidoborane-bis-η⁵-(2-methyl-4-naphthylinden-1-yl)hafnium bis-dimethylamide;
diisopropylamidoborane-bis-η⁵-(2-methyl-4-naphthylinden-1-yl)hafnium 2-methyl-1,3-butadiene;
diisopropylamidoborane-bis-η⁵-(2-methyl-4-naphthylinden-1-yl)hafnium 2,3-dimethyl-1,3-butadiene;
diisopropylamidoborane-bis-η⁵-(2-methyl-4-naphthylinden-1-yl)hafnium 2-N,N-dimethylaminobenzyl;
diisopropylamidoborane-bis-η⁵-(2-methyl-4-naphthylinden-1-yl)hafnium allyl;
diisopropylamidoborane-bis-η⁵-(2-methyl-4-naphthylinden-1-yl)hafnium η⁴-1,4-diphenyl-1,3-butadiene;
diisopropylamidoborane-bis-η⁵-(2-methyl-4-naphthylinden-1-yl)hafnium η⁴-2,4-hexadiene;
diisopropylamidoborane-bis-η⁵-(2-methyl-4-naphthylinden-1-yl)hafnium η⁴-1,4-dinaphthyl-1,3-butadiene;
diisopropylamidoborane-bis-η⁵-(2-methyl-4-naphthylinden-1-yl)hafnium η⁴-1-phenyl-1,3-pentadiene;
diisopropylamidoborane-bis-η⁵-(2-methyl-4-naphthylinden-1-yl)hafnium η⁴-1,3-pentadiene;
diisopropylamidoborane-bis-η⁵-(3-isopropylinden-1-yl)hafnium dichloride;
diisopropylamidoborane-bis-η⁵-(3-isopropylinden-1-yl)hafnium dimethyl;
diisopropylamidoborane-bis-η⁵-(3-isopropylinden-1-yl)hafnium bis-dimethylamide;
diisopropylamidoborane-bis-η⁵-(3-isopropylinden-1-yl)hafnium 2-methyl-1,3-butadiene;
diisopropylamidoborane-bis-η⁵-(3-isopropylinden-1-yl)hafnium 2,3-dimethyl-1,3-butadiene;
diisopropylamidoborane-bis-η⁵-(3-isopropylinden-1-yl)hafnium 2-N,N-dimethylaminobenzyl;
diisopropylamidoborane-bis-η⁵-(3-isopropylinden-1-yl)hafnium allyl;
diisopropylamidoborane-bis-η⁵-(3-isopropylinden-1-yl)hafnium η⁴-1,4-diphenyl-1,3-butadiene;
diisopropylamidoborane-bis-η⁵-(3-isopropylinden-1-yl)hafnium η⁴-2,4-hexadiene;
diisopropylamidoborane-bis-η⁵-(3-isopropylinden-1-yl)hafnium η⁴-1,4-dinaphthyl-1,3-butadiene;
diisopropylamidoborane-bis-η⁵-(3-isopropylinden-1-yl)hafnium η⁴-1-phenyl-1,3-pentadiene;

diisopropylamidoborane-bis-$\eta^5$-(3-isopropylinden-1-yl)hafnium $\eta^4$-1,3-pentadiene;
diisopropylamidoborane-bis-$\eta^5$-(3-t-butylinden-1-yl)hafnium dichloride;
diisopropylamidoborane-bis-$\eta^5$-(3-t-butylinden-1-yl)hafnium dimethyl;
diisopropylamidoborane-bis-$\eta^5$-(3-t-butylinden-1-yl)hafnium bis-dimethylamide;
diisopropylamidoborane-bis-$\eta^5$-(3-t-butylinden-1-yl)hafnium 2-methyl-1,3-butadiene;
diisopropylamidoborane-bis-$\eta^5$-(3-t-butylinden-1-yl)hafnium 2,3-dimethyl-1,3-butadiene;
diisopropylamidoborane-bis-$\eta^5$-(3-t-butylinden-1-yl)hafnium 2-N,N-dimethylaminobenzyl;
diisopropylamidoborane-bis-$\eta^5$-(3-t-butylinden-1-yl)hafnium allyl;
diisopropylamidoborane-bis-$\eta^5$-(3-t-butylinden-1-yl)hafnium $\eta^4$-1,4-diphenyl-1,3-butadiene;
diisopropylamidoborane-bis-$\eta^5$-(3-t-butylinden-1-yl)hafnium $\eta^4$-2,4-hexadiene;
diisopropylamidoborane-bis-$\eta^5$-(3-t-butylinden-1-yl)hafnium $\eta^4$-1,4-dinaphthyl-1,3-butadiene;
diisopropylamidoborane-bis-$\eta^5$-(3-t-butylinden-1-yl)hafnium $\eta^4$-1-phenyl-1,3-pentadiene;
diisopropylamidoborane-bis-$\eta^5$-(3-t-butylinden-1-yl)hafnium $\eta^4$-1,3-pentadiene;
bis(trimethylsilyl)amidoborane-bis-$\eta^5$-cyclopentadienylhafnium dichloride;
bis(trimethylsilyl)amidoborane-bis-$\eta^5$-cyclopentadienylhafnium dimethyl;
bis(trimethylsilyl)amidoborane-bis-$\eta^5$-cyclopentadienylhafnium bis-dimethylamide;
bis(trimethylsilyl)amidoborane-bis-$\eta^5$-cyclopentadienylhafnium 2-methyl-1,3-butadiene;
bis(trimethylsilyl)amidoborane-bis-$\eta^5$-cyclopentadienylhafnium 2,3-dimethyl-1,3-butadiene;
bis(trimethylsilyl)amidoborane-bis-$\eta^5$-cyclopentadienylhafnium 2-N,N-dimethylaminobenzyl;
bis(trimethylsilyl)amidoborane-bis-$\eta^5$-cyclopentadienylhafnium allyl;
bis(trimethylsilyl)amidoborane-bis-$\eta^5$-cyclopentadienylhafnium $\eta^4$-1,4-diphenyl-1,3-butadiene;
bis(trimethylsilyl)amidoborane-bis-$\eta^5$-cyclopentadienylhafnium $\eta^4$-2,4-hexadiene;
bis(trimethylsilyl)amidoborane-bis-$\eta^5$-cyclopentadienylhafnium $\eta^4$-1,4-dinaphthyl-1,3-butadiene;
bis(trimethylsilyl)amidoborane-bis-$\eta^5$-cyclopentadienylhafnium $\eta^4$-1-phenyl-1,3-pentadiene;
bis(trimethylsilyl)amidoborane-bis-$\eta^5$-cyclopentadienylhafnium $\eta^4$-1,3-pentadiene;
bis(trimethylsilyl)amidoborane-bis-$\eta^5$-inden-1-ylhafnium dichloride;
bis(trimethylsilyl)amidoborane-bis-$\eta^5$-inden-1-ylhafnium dimethyl;
bis(trimethylsilyl)amidoborane-bis-$\eta^5$-inden-1-ylhafnium bis-dimethylamide;
bis(trimethylsilyl)amidoborane-bis-$\eta^5$-inden-1-ylhafnium 2-methyl-1,3-butadiene;
bis(trimethylsilyl)amidoborane-bis-$\eta^5$-inden-1-ylhafnium 2,3-dimethyl-1,3-butadiene;
bis(trimethylsilyl)amidoborane-bis-$\eta^5$-inden-1-ylhafnium 2-N,N-dimethylaminobenzyl;
bis(trimethylsilyl)amidoborane-bis-$\eta^5$-inden-1-ylhafnium allyl;
bis(trimethylsilyl)amidoborane-bis-$\eta^5$-inden-1-ylhafnium $\eta^4$-1,4-diphenyl-1,3-butadiene;
bis(trimethylsilyl)amidoborane-bis-$\eta^5$-inden-1-ylhafnium $\eta^4$-2,4-hexadiene;
bis(trimethylsilyl)amidoborane-bis-$\eta^5$-inden-1-ylhafnium $\eta^4$-1,4-dinaphthyl-1,3-butadiene;
bis(trimethylsilyl)amidoborane-bis-$\eta^5$-inden-1-ylhafnium $\eta^4$-1-phenyl-1,3-pentadiene;
bis(trimethylsilyl)amidoborane-bis-$\eta^5$-inden-1-ylhafnium $\eta^4$-1,3-pentadiene;
bis(trimethylsilyl)amidoborane-bis-$\eta^5$-(2-methylinden-1-yl)hafnium dichloride;
bis(trimethylsilyl)amidoborane-bis-$\eta^5$-(2-methylinden-1-yl)hafnium dimethyl;
bis(trimethylsilyl)amidoborane-bis-$\eta^5$-(2-methylinden-1-yl)hafnium bis-dimethylamide;
bis(trimethylsilyl)amidoborane-bis-$\eta^5$-(2-methylinden-1-yl)hafnium 2-methyl-1,3-butadiene;
bis(trimethylsilyl)amidoborane-bis-$\eta^5$-(2-methylinden-1-yl)hafnium 2,3-dimethyl-1,3-butadiene;
bis(trimethylsilyl)amidoborane-bis-$\eta^5$-(2-methylinden-1-yl)hafnium 2-N,N-dimethylaminobenzyl;
bis(trimethylsilyl)amidoborane-bis-$\eta^5$-(2-methylinden-1-yl)hafnium allyl;
bis(trimethylsilyl)amidoborane-bis-$\eta^5$-(2-methylinden-1-yl)hafnium $\eta^4$-1,4-diphenyl-1,3-butadiene;
bis(trimethylsilyl)amidoborane-bis-$\eta^5$-(2-methylinden-1-yl)hafnium $\eta^4$-2,4-hexadiene;
bis(trimethylsilyl)amidoborane-bis-$\eta^5$-(2-methylinden-1-yl)hafnium $\eta^4$-1,4-dinaphthyl-1,3-butadiene;
bis(trimethylsilyl)amidoborane-bis-$\eta^5$-(2-methylinden-1-yl)hafnium $\eta^4$-1-phenyl-1,3-pentadiene;
bis(trimethylsilyl)amidoborane-bis-$\eta^5$-(2-methylinden-1-yl)hafnium $\eta^4$-1,3-pentadiene;
bis(trimethylsilyl)amidoborane-bis-$\eta^5$-(2-methyl-4-phenylinden-1-yl)hafnium dichloride;
bis(trimethylsilyl)amidoborane-bis-$\eta^5$-(2-methyl-4-phenylinden-1-yl)hafnium dimethyl;
bis(trimethylsilyl)amidoborane-bis-$\eta^5$-(2-methyl-4-phenylinden-1-yl)hafnium bis-dimethylamide;
bis(trimethylsilyl)amidoborane-bis-$\eta^5$-(2-methyl-4-phenylinden-1-yl)hafnium 2-methyl-1,3-butadiene;
bis(trimethylsilyl)amidoborane-bis-$\eta^5$-(2-methyl-4-phenylinden-1-yl)hafnium 2,3-dimethyl-1,3-butadiene;
bis(trimethylsilyl)amidoborane-bis-$\eta^5$-(2-methyl-4-phenylinden-1-yl)hafnium 2-N,N-dimethylaminobenzyl;
bis(trimethylsilyl)amidoborane-bis-$\eta^5$-(2-methyl-4-phenylinden-1-yl)hafnium allyl;
bis(trimethylsilyl)amidoborane-bis-$\eta^5$-(2-methyl-4-phenylinden-1-yl)hafnium $\eta^4$-1,4-diphenyl-1,3-butadiene;
bis(trimethylsilyl)amidoborane-bis-$\eta^5$-(2-methyl-4-phenylinden-1-yl)hafnium $\eta^4$-2,4-hexadiene;
bis(trimethylsilyl)amidoborane-bis-$\eta^5$-(2-methyl-4-phenylinden-1-yl)hafnium $\eta^4$-1,4-dinaphthyl-1,3-butadiene;
bis(trimethylsilyl)amidoborane-bis-$\eta^5$-(2-methyl-4-phenylinden-1-yl)hafnium $\eta^4$-1-phenyl-1,3-pentadiene;
bis(trimethylsilyl)amidoborane-bis-$\eta^5$-(2-methyl-4-phenylinden-1-yl)hafnium $\eta^4$-1,3-pentadiene;
bis(trimethylsilyl)amidoborane-bis-$\eta^5$-(2-methyl-4-naphthylinden-1-yl)hafnium dimethyl dichloride;
bis(trimethylsilyl)amidoborane-bis-$\eta^5$-(2-methyl-4-naphthylinden-1-yl)hafnium dimethyl;
bis(trimethylsilyl)amidoborane-bis-$\eta^5$-(2-methyl-4-naphthylinden-1-yl)hafnium dimethyl;
bis(trimethylsilyl)amidoborane-bis-$\eta^5$-(2-methyl-4-naphthylinden-1-yl)hafnium bis-methylamide;
bis(trimethylsilyl)amidoborane-bis-$\eta^5$-(2-methyl-4-napthylinden-1-yl)hafnium 2-methyl-1,3-butadiene;

bis(trimethylsilyl)amidoborane-bis-η5-(2-methyl-4-naphthylinden-1-yl)hafnium 2,3-dimethyl-1,3-butadiene;
bis(trimethylsilyl)amidoborane-bis-η5-(2-methyl-4-naphthylinden-1-yl)hafnium 2-N,N-dimethylaminobenzyl;
bis(trimethylsilyl)amidoborane-bis-η5-(2-methyl-4-naphthylinden-1-yl)hafnium allyl;
bis(trimethylsilyl)amidoborane-bis-η5-(2-methyl-4-naphthylinden-1-yl)hafnium η5-1,4-diphenyl-1,3-butadiene;
bis(trimethylsilyl)amidoborane-bis-η5-(2-methyl-4-naphthylinden-1-yl)hafnium η4-2,4-hexadiene;
bis(trimethylsilyl)amidoborane-bis-η5-(2-methyl-4-naphthylinden-1-yl)hafnium η4-1,4-dinaphthyl-1,3-butadiene;
bis(trimethylsilyl)amidoborane-bis-η5-(2-methyl-4-naphthylinden-1-yl)hafnium η4-1-phenyl-1,3-pentadiene;
bis(trimethylsilyl)amidoborane-bis-η5-(2-methyl-4-naphthylinden-1-yl)hafnium η4-1,3-pentadiene;
bis(trimethylsilyl)amidoborane-bis-η5-(3-isopropylinden-1-yl)hafnium dichloride;
bis(trimethylsilyl)amidoborane-bis-η5-(3-isopropylinden-1-yl)hafnium dimethyl;
bis(trimethylsilyl)amidoborane-bis-η5-(3-isopropylinden-1-yl)hafnium bis-dimethylamide;
bis(trimethylsilyl)amidoborane-bis-η5-(3-isopropylinden-1-yl)hafnium 2-methyl-1,3-butadiene;
bis(trimethylsilyl)amidoborane-bis-η5-(3-isopropylinden-1-yl)hafnium 2,3-dimethyl-1,3-butadiene;
bis(trimethylsilyl)amidoborane-bis-η5-(3-isopropylinden-1-yl)hafnium 2-N,N-dimethylaminobenzyl;
bis(trimethylsilyl)amidoborane-bis-η5-(3-isopropylinden-1-yl)hafnium allyl;
bis(trimethylsilyl)amidoborane-bis-η5-(3-isopropylinden-1-yl)hafnium η5-1,4-diphenyl-1,3-butadiene;
bis(trimethylsilyl)amidoborane-bis-η5-(3-isopropylinden-1-yl)hafnium η4-2,4-hexadiene;
bis(trimethylsilyl)amidoborane-bis-η5-(3-isopropylinden-1-yl)hafnium η4-1,4-dinaphthyl-1,3-butadiene;
bis(trimethylsilyl)amidoborane-bis-η5-(3-isopropylinden-1-yl)hafnium η4-1-phenyl-1,3-pentadiene;
bis(trimethylsilyl)amidoborane-bis-η5-(3-isopropylinden-1-yl)hafnium η4-1,3-pentadiene;
bis(trimethylsilyl)amidoborane-bis-η5-(3-t-butylinden-1-yl)hafnium dichloride;
bis(trimethylsilyl)amidoborane-bis-η5-(3-t-butylinden-1-yl)hafnium dimethyl;
bis(trimethylsilyl)amidoborane-bis-η5-(3-t-butylinden-1-yl)hafnium bis-dimethylamide;
bis(trimethylsilyl)amidoborane-bis-η5-(3-t-butylinden-1-yl)hafnium 2-methyl-1,3-butadiene;
bis(trimethylsilyl)amidoborane-bis-η5-(3-t-butylinden-1-yl)hafnium 2,3-dimethyl-1,3-butadiene;
bis(trimethylsilyl)amidoborane-bis-η5-(3-t-butylinden-1-yl)hafnium 2-N,N-dimethylaminobenzyl;
bis(trimethylsilyl)amidoborane-bis-η5-(3-t-butylinden-1-yl)hafnium allyl;
bis(trimethylsilyl)amidoborane-bis-η5-(3-t-butylinden-1-yl)hafnium η4-1,4-diphenyl-1,3-butadiene;
bis(trimethylsilyl)amidoborane-bis-η5-(3-t-butylinden-1-yl)hafnium η4-2,4-hexadiene;
bis(trimethylsilyl)amidoborane-bis-η5-(3-t-butylinden-1-yl)hafnium η4-1,4-dinaphthyl-1,3-butadiene;
bis(trimethylsilyl)amidoborane-bis-η5-(3-t-butylinden-1-yl)hafnium η4-1-phenyl-1,3-pentadiene;
bis(trimethylsilyl)amidoborane-bis-η5-(3-t-butylinden-1-yl)hafnium η4-1,3-pentadiene;
bis(diisopropylamido)diborane-1,2-bis-η5-(2-methyl-4-phenylinden-1-yl)hafnium dichloride;
bis(diisopropylamido)diborane-1,2-bis-η5-(2-methyl-4-phenylinden-1-yl)hafnium dimethyl;
bis(diisopropylamido)diborane-1,2-bis-η5-(2-methyl-4-phenylinden-1-yl)hafnium bis-dimethylamide;
bis(diisopropylamido)diborane-1,2-bis-η5-(2-methyl-4-phenylinden-1-yl)hafnium 2-methyl-1,3-butadiene;
bis(diisopropylamido)diborane-1,2-bis-η5-(2-methyl-4-phenylinden-1-yl)hafnium 2,3-dimethyl-1,3-butadiene;
bis(diisopropylamido)diborane-1,2-bis-η5-(2-methyl-4-phenylinden-1-yl)hafnium 2-N,N-dimethylaminobenzyl;
bis(diisopropylamido)diborane-1,2-bis-η5-(2-methyl-4-phenylinden-1-yl)hafnium allyl;
bis(diisopropylamido)diborane-1,2-bis-η5-(2-methyl-4-phenylinden-1-yl)hafnium η4-1,4-diphenyl-1,3-butadiene;
bis(diisopropylamido)diborane-7,2-bis-η5-(2-methyl-4-phenylinden-1-yl)hafnium η4-2,4-hexadiene;
bis(diisopropylamido)diborane-1,2-bis-η5-(2-methyl-4-phenylinden-1-yl)hafnium η4-1,4-dinaphthyl-1,3-butadiene;
bis(diisopropylamido)diborane-1,2-bis-η5-(2-methyl-4-phenylinden-1-yl)hafnium η4-1-phenyl-1,3-pentadiene;
bis(diisopropylamido)diborane-1,2-bis-η5-(2-methyl-4-phenylinden-1-yl)zirconium η4-1,3-pentadiene;
(η5-tetramethylcyclopentadienyl)(tert-butylamido) diisopropylamidoborane titanium dichloride;
(η5-tetramethylcyclopentadienyl)(tert-butylamido) diisopropylamidoborane titanium dimethyl;
(η5-tetramethylcyclopentadienyl)(tert-butylamido) diisopropylamidoborane titanium bis-dimethylamide;
(η5-tetramethylcyclopentadienyl)(tert-butylamido) diisopropylamidoborane titanium 2-methyl-1,3-butadiene;
(η5-tetramethylcyclopentadienyl)(tert-butylamido) diisopropylamidoborane titanium 2,3-dimethyl-1,3-butadiene;
(η5-tetramethylcyclopentadienyl)(tert-butylamido) diisopropylamidoborane titanium 2-N,N-dimethylaminobenzyl;
(η5-tetramethylcyclopentadienyl)(tert-butylamido) diisopropylamidoborane titanium allyl;
(η5-tetramethylcyctopentadienyl)(tert-butylamido) diisopropylamidoborane titanium η4-1,4-diphenyl-1,3-butadiene;
(η5-tetramethylcyclopentadienyl)(tert-butylamido) diisopropylamidoborane titanium η4-2,4-hexadiene;
(η5-tetramethylcyclopentadienyl)(tert-butylamido) diisopropylamidoborane titanium η4-1,4-dinaphthyl-1,3-butadiene;
(η5-tetramethylcyclopentadienyl)(tert-butylamido) diisopropylamidoborane titanium η4-1-phenyl-1,3-pentadiene;
(η5-tetramethylcyclopentadienyl)(tert-butylamido) diisopropylamidoborane titanium η4-1,3-pentadiene;
(η5-tetramethylcyclopentadienyl)(cyclohexylamido) diisopropylamidoborane titanium dichloride;
(η5-tetramethylcyclopentadienyl)(cyclohexylamido) diisopropylamidoborane titanium dimethyl;
(η5-tetramethylcyclopentadienyl)(cyclohexylamido) diisopropylamidoborane titanium bis-dimethylamide;
(η5-tetramethylcyclopentadienyl)(cyclohexylamido) diisopropylamidoborane titanium 2-methyl-1,3-butadiene;
(η5-tetramethylcyclopentadienyl)(cyclohexylamido) diisopropylamidoborane titanium 2,3-dimethyl-1,3-butadiene;
(η5-tetramethylcyclopentadienyl)(cyclohexylamido) diisopropylamidoborane titanium 2-N,N-dimethylaminobenzyl;

($\eta^5$-tetramethylcyclopentadienyl)(cyclohexylamido) diisopropylamidoborane titanium allyl;

($\eta^5$-tetramethylcyclopentadienyl)(cyclohexylamido) diisopropylamidoborane titanium $\eta^4$-1,4-diphenyl-1,3-butadiene;

($\eta^5$-tetramethylcyclopentadienyl)(cyclohexylamido) diisopropylamidoborane titanium η4-2,4-hexadiene;

($\eta^5$-tetramethylcyclopentadienyl)(cyclohexylamido) diisopropylamidoborane titanium $\eta^4$-1,4-dinaphthyl-1,3-butadiene;

($\eta^5$-tetramethylcyclopentadienyl)(cyclohexylamido) diisopropylamidoborane titanium $\eta^4$-1-phenyl-1,3-pentadiene;

($\eta^5$-tetramethylcyclopentadienyl)(cyclohexylamido) diisopropylamidoborane titanium η4-1,3-pentadiene;

($\eta^5$-tetramethylcyclopentadienyl)(tert-butylamido)bis(diisopropylamido) diborane titanium dichloride;

($\eta^5$-tetramethylcyclopentadienyl)(tert-butylamido) bis(diisopropylamide) diborane titanium dimethyl;

($\eta^5$-tetramethylcyclopentadienyl)(tert-butylamido) bis(diisopropylamide) diborane titanium bis-dimethylamide;

($\eta^5$-tetramethylcyclopentadienyl)(tert-butylamido) bis(diisopropylamide) diborane titanium 2-methyl-1,3-butadiene;

($\eta^5$-tetramethylcyclopentadienyl)(tert-butylamido) bis(diisopropylamide) diborane titanium 2,3-dimethyl-1,3-butadiene;

($\eta^5$-tetramethylcyclopentadienyl)(tert-butylamido) bis(diisopropylamide) diborane titanium 2-N,N-dimethylaminobenzyl;

($\eta^5$-tetramethylcyclopentadienyl)(tert-butylamido) bis(diisopropylamide) diborane titanium allyl;

($\eta^5$-tetramethylcyclopentadienyl)(tert-butylamido) bis(diisopropylamide) diborane titanium $\eta^4$-1,4-diphenyl-1,3-butadiene;

($\eta^5$-tetramethylcyclopentadienyl)(tert-butylamido) bis(diisopropylamide) diborane titanium $\eta^4$-2,4-hexadiene;

($\eta^5$-tetramethylcyclopentadienyl)(tert-butylamido) bis(diisopropylamide) diborane titanium $\eta^4$-1,4-dinaphthyl-1,3-butadiene;

($\eta^5$-tetramethylcyclopentadienyl)(tert-butylamido) bis(diisopropylamide) diborane titanium $\eta^4$-1-phenyl-1,3-pentadiene;

($\eta^5$-tetramethylcyclopentadienyl)(tert-butylamido) bis(diisopropylamide) diborane titanium $\eta^4$-1,3-pentadiene;

($\eta^5$-tetramethylcyclopentadienyl)(phenylamido) diisopropylamidoborane titanium dichloride;

($\eta^5$-tetramethylcyclopentadienyl)(phenylamido) diisopropylamidoborane titanium dimethyl;

($\eta^5$-tetramethylcyclopentadienyl)(phenylamido) diisopropylamidoborane titanium bis-dimethylamide;

($\eta^5$-tetramethylcyclopentadienyl)(phenylamido) diisopropylamidoborane titanium 2-methyl-1,3-butadiene;

($\eta^5$-tetramethylcyclopentadienyl)(phenylamido) diisopropylamidoborane titanium 2,3-dimethyl-1,3-butadiene;

($\eta^5$-tetramethylcyclopentadienyl)(phenylamido) diisopropylamidoborane titanium 2-N,N-dimethylaminobenzyl;

($\eta^5$-tetramethylcyclopentadienyl)(phenylamido) diisopropylamidoborane titanium allyl;

($\eta^5$-tetramethylcyclopentadienyl)(phenylamido) diisopropylamidoborane titanium $\eta^4$-1,4-diphenyl-1,3-butadiene;

($\eta^5$-tetramethylcyclopentadienyl)(phenylamido) diisopropylamidoborane titanium $\eta^4$-2,4-hexadiene;

($\eta^5$-tetramethylcyclopentadienyl)(phenylamido) diisopropylamidoborane titanium $\eta^4$-1,4-dinaphthyl-1,3-butadiene;

($\eta^5$-tetramethylcyclopentadienyl)(phenylamido) diisopropylamidoborane titanium $\eta^4$-1-phenyl-1,3-pentadiene;

($\eta^5$-tetramethylcyclopentadienyl)(phenylamido) diisopropylamidoborane titanium η4-1,3-pentadiene;

($\eta^5$-tetramethylcyclopentadienyl)(tert-butylamido) dimethylamidoborane titanium dichloride;

($\eta^5$-tetramethylcyclopentadienyl)(tert-butylamido) dimethylamidoborane titanium dimethyl;

($\eta^5$-tetramethylcyclopentadienyl)(tert-butylamido) dimethylamidoborane titanium bis-dimethylamide;

($\eta^5$-tetramethylcyclopentadienyl)(tert-butylamido) dimethylamidoborane titanium 2-methyl-1,3-butadiene;

($\eta^5$-tetramethylcyclopentadienyl)(tert-butylamido) dimethylamidoborane titanium 2,3-dimethyl-1,3-butadiene;

($\eta^5$-tetramethylcyclopentadienyl)(tert-butylamido) dimethylamidoborane titanium 2-N,N-dimethylaminobenzyl;

($\eta^5$-tetramethylcyclopentadienyl)(tert-butylamido) dimethylamidoborane titanium allyl;

($\eta^5$-tetramethylcyclopentadienyl)(tert-butylamido) dimethylamidoborane titanium $\eta^4$-1,4-diphenyl-1,3-butadiene;

($\eta^5$-tetramethylcyclopentadienyl)(tert-butylamido) dimethylamidoborane titanium $\eta^4$-2,4-hexadiene;

($\eta^5$-tetramethylcyclopentadienyl)(tert-butylamido) dimethylamidoborane titanium $\eta^4$-1,4-dinaphthyl-1,3-butadiene;

($\eta^5$-tetramethylcyclopentadienyl)(tert-butylamido) dimethylamidoborane titanium $\eta^4$-1-phenyl-1,3-pentadiene;

($\eta^5$-tetramethylcyclopentadienyl)(tert-butylamido) dimethylamidoborane titanium $\eta^4$-1,3-pentadiene;

($\eta^5$-inden-1-yl)(tert-butylamido)diisopropylamidoborane titanium dichloride;

($\eta^5$-inden-1-yl)(tert-butylamido)diisopropylamidoborane titanium dimethyl;

($\eta^5$-inden-1-yl)(tert-butylamido)diisopropylamidoborane titanium bis-dimethylamide;

($\eta^5$-inden-1-yl)(tert-butylamido)diisopropylamidoborane titanium 2-methyl-1,3-butadiene;

($\eta^5$-inden-1-yl)(tert-butylamido)diisopropylamidoborane titanium 2,3-dimethyl-1,3-butadiene;

($\eta^5$-inden-1-yl)(tert-butylamido)diisopropylamidoborane titanium 2-N,N-dimethylaminobenzyl;

($\eta^5$-inden-1-yl)(tert-butylamido)diisopropylamidoborane titanium ally;

($\eta^5$-inden-1-yl)(tert-butylamido)diisopropylamidoborane titanium $\eta^4$-1,4-diphenyl-1,3-butadiene;

($\eta^5$-inden-1-yl)(tert-butylamido)diisopropylamidoborane titanium $\eta^4$-2,4-hexadiene;

($\eta^5$-inden-1-yl)(tert-butylamido)diisopropylamidoborane titanium $\eta^4$-1,4-dinaphthyl-1,3-butadiene;

($\eta^5$-inden-1-yl)(tert-butylamido)diisopropylamidoborane titanium $\eta^4$-1-phenyl-1,3-pentadiene;

($\eta^5$-inden-1-yl)(tert-butylamido)diisopropylamidoborane titanium $\eta^4$-1,3-pentadiene;

($\eta^5$-2,3-dimethylinden-1-yl)(tert-butylamido) diisopropylamidoborane titanium dichloride;

($\eta^5$-2,3-dimethylinden-1-yl)(tert-butylamido) diisopropylamidoborane titanium dimethyl;

($\eta^5$-2,3-dimethylinden-1-yl)(tert-butylamido) diisopropylamidoborane titanium bis-dimethylamide;

($\eta^5$-2,3-dimethylinden-1-yl)(tert-butylamido) diisopropylamidoborane titanium 2-methyl-1,3-butadiene;

($\eta^5$-2,3-dimethylinden-1-yl)(tert-butylamido) diisopropylamidoborane titanium 2,3-dimethyl-1,3-butadiene;

($\eta^5$-2,3-dimethylinden-1-yl)(tert-butylamido) diisopropylamidoborane titanium 2-N,N-dimethylaminobenzyl;
($\eta^5$-2,3-dimethylinden-1-yl)(tert-butylamido) diisopropylamidoborane titanium allyl;
($\eta^5$-2,3-dimethylinden-1-yl)(tert-butylamido) diisopropylamidoborane titanium $\eta^4$-1,4-diphenyl-1,3-butadiene;
($\eta^5$-2,3-dimethylinden-1-yl)(tert-butylamido) diisopropylamidoborane titanium $\eta^4$-2,4-hexadiene;
($\eta^5$-2,3-dimethylinden-1-yl)(tert-butylamido) diisopropylamidoborane titanium $\eta^4$-1,4-dinaphthyl-1,3-butadiene;
($\eta^5$-2,3-dimethylinden-1-yl)(tert-butylamido) diisopropylamidoborane titanium $\eta^4$-1-phenyl-1,3-pentadiene;
($\eta^5$-2,3-dimethylinden-1-yl)(tert-butylamido) diisopropylamidoborane titanium $\eta^4$-1,3-pentadiene;
($\eta^5$-2-pyrrolidenylinden-1-yl)(tert-butylamido) diisopropylamidoborane titanium dichloride;
($\eta^5$-2-pyrrolidenylinden-1-yl)(tert-butylamido) diisopropylamidoborane titanium dimethyl;
($\eta^5$-2-pyrrolidenylinden-1-yl)(tert-butylamido) diisopropylamidoborane titanium bis-dimethylamide;
($\eta^5$-2-pyrrolidenylinden-1-yl)(tert-butylamido) diisopropylamidoborane titanium 2-methyl-1,3-butadiene;
($\eta^5$-2-pyrrolidenylinden-1-yl)(tert-butylamido) diisopropylamidoborane titanium 2,3-dimethyl-1,3-butadiene;
($\eta^5$-2-pyrrolidenylinden-1-yl)(tert-butylamido) diisopropylamidoborane titanium 2-N,N-dimethylaminobenzyl;
($\eta^5$-2-pyrrolidenylinden-1-yl)(tert-butylamido) diisopropylamidoborane titanium allyl;
($\eta^5$-2-pyrrolidenylinden-1-yl)(tert-butylamido) diisopropylamidoborane titanium $\eta^4$-1,4-diphenyl-1,3-butadiene;
($\eta^5$-2-pyrrolidenylinden-1-yl)(tert-butylamido) diisopropylamidoborane titanium $\eta^4$-2,4-hexadiene;
($\eta^5$-2-pyrrolidenylinden-1-yl)(tert-butylamido) diisopropylamidoborane titanium $\eta^4$-1,4-dinaphthyl-1,3-butadiene;
($\eta^5$-2-pyrrolidenylinden-1-yl)(tert-butylamido) diisopropylamidoborane titanium $\eta^4$-1-phenyl-1,3-pentadiene;
($\eta^5$-2-pyrrolidenylinden-1-yl)(tert-butylamido) diisopropylamidoborane titanium $\eta^4$-1,3-pentadiene;
bis-phenylamido-bis(diisopropylamido)diborane titanium dichloride;
bis-phenylamido-bis(diisopropylamido)diborane titanium dimethyl;
bis-phenylamido-bis(diisopropylamido)diborane titanium bis-dimethylamide;
bis-phenylamido-bis(diisopropylamido)diborane titanium 2-methyl-1,3-butadiene;
bis-phenylamido-bis(diisopropylamido)diborane titanium 2,3-dimethyl-1,3-butadiene;
bis-phenylamido-bis(diisopropylamido)diborane titanium 2-N,N-dimethylaminobenzyl;
bis-phenylamido-bis(diisopropylamido)diborane titanium allyl;
bis-phenylamido-bis(diisopropylamido)diborane titanium $\eta^4$-1,4-diphenyl-1,3-butadiene;
bis-phenylamido-bis(diisopropylamido)diborane titanium $\eta^4$-2,4-hexadiene;
bis-phenylamido-bis(diisopropylamido)diborane titanium $\eta^4$-1,4-dinaphthyl-1,3-butadiene;
bis-phenylamido-bis(diisopropylamido)diborane titanium $\eta^4$-1-phenyl-1,3-pentadiene;
bis-phenylamido-bis(diisopropylamido)diborane titanium $\eta^4$-1,3-pentadiene;
bis-2,6-diisopropylphenylamido-bis(diisopropylamido) diborane titanium dichloride;
bis-2,6-diisopropylphenylamido-bis(diisopropylamido) diborane titanium dimethyl;
bis-2,6-diisopropylphenylamido-bis(diisopropylamido) diborane titanium bis-dimethylamide;
bis-2,6-diisopropylphenylamido-bis(diisopropylamido) diborane titanium 2-methyl-1,3-butadiene;
bis-2,6-diisopropylphenylamido-bis(diisopropylamido) diborane titanium 2,3-dimethyl-1,3-butadiene;
bis-2,6-diisopropylphenylamido-bis(diisopropylamido) diborane titanium 2-N,N-dimethylaminobenzyl;
bis-2,6-diisopropylphenylamido-bis(diisopropylamido) diborane titanium allyl;
bis-2,6-diisopropylphenylamido-bis(diisopropylamido) diborane titanium $\eta^4$-1,4-diphenyl-1,3-butadiene;
bis-2,6-diisopropylphenylamido-bis(diisopropylamido) diborane titanium $\eta^4$-2,4-hexadiene;
bis-2,6-diisopropylphenylamido-bis(diisopropylamido) diborane titanium $\eta^4$-1,4-dinaphthyl-1,3-butadiene;
bis-2,6-diisopropylphenylamido-bis(diisopropylamido) diborane titanium $\eta^4$-1-phenyl-1,3-pentadiene;
bis-2,6-diisopropylphenylamido-bis(diisopropylamido) diborane titanium $\eta^4$-1,3-pentadiene;
bis-3,5-dimethylbenzylamido-bis(dimethylamido)diborane titanium dichloride;
bis-3,5-dimethylbenzylamido-bis(dimethylamido)diborane titanium dimethyl;
bis-3,5-dimethylbenzylamido-bis(dimethylamido)diborane titanium bis-dimethylamide;
bis-3,5-dimethylbenzylamido-bis(dimethylamido)diborane titanium 2-methyl-1,3-butadiene;
bis-3,5-dimethylbenzylamido-bis(dimethylamido)diborane titanium 2,3-dimethyl-1,3-butadiene;
bis-3,5-dimethylbenzylamido-bis(dimethylamido)diborane titanium 2-N,N-dimethylaminobenzyl;
bis-3,5-dimethylbenzylamido-bis(dimethylamido)diborane titanium allyl;
bis-3,5-dimethylbenzylamido-bis(dimethylamido)diborane titanium $\eta^4$-1,4-diphenyl-1,3-butadiene;
bis-3,5-dimethylbenzylamido-bis(dimethylamido)diborane titanium $\eta^4$-2,4-hexadiene;
bis-3,5-dimethylbenzylamido-bis(dimethylamido)diborane titanium $\eta^4$-1,4-dinaphthyl-1,3-butadiene;
bis-3,5-dimethylbenzylamido-bis(dimethylamido)diborane titanium $\eta$4-1-phenyl-1,3-pentadiene;
bis-3,5-dimethylbenzylamido-bis(dimethylamido) diborane titanium $\eta$4-1,3-pentadiene;
bis-2,6-dimethylbenzylamido-bis(dimethylamido)diborane titanium dichloride;
bis-2,6-dimethylbenzylamido-bis(dimethylamido)diborane titanium dimethyl;
bis-2,6-dimethylbenzylamido-bis(dimethylamido)diborane titanium bis-dimethylamide;
bis-2,6-dimethylbenzylamido-bis(dimethylamido)diborane titanium-2-methyl-1,3-butadiene;
bis-2,6-dimethylbenzylamido-bis(dimethylamido)diborane titanium 2,3-dimethyl-1,3-butadiene;
bis-2,6-dimethylbenzylamido-bis(dimethylamido)diborane titanium 2-N,N-dimethylaminobenzyl;
bis-2,6-dimethylbenzylamido-bis(dimethylamido)diborane titanium allyl;
bis-2,6-dimethylbenzylamido-bis(dimethylamido)diborane titanium $\eta^4$-1,4-diphenyl-1,3-butadiene;

bis-2,6-dimethylbenzylamido-bis(dimethylamido)diborane titanium η$^4$-2,4-hexadiene;
bis-2,6-dimethylbenzylamido-bis(dimethylamido)diborane titanium η$^4$-1,4-dinaphthyl-1,3-butadiene;
bis-2,6-dimethylbenzylamido-bis(dimethylamido)diborane titanium η$^4$-1-phenyl-1,3-pentadiene;
bis-2,6-dimethylbenzylamido-bis(dimethylamido)diborane titanium η$^4$-1,3-pentadiene;
bis-2,6-diisopropylphenylamido-bis(dimethylamido) diborane titanium dichloride;
bis-2,6-diisopropylphenylamido-bis(dimethylamido) diborane titanium dimethyl;
bis-2,6-diisopropylphenylamido-bis(dimethylamido) diborane titanium bis-dimethylamide;
bis-2,6-diisopropylphenylamido-bis(dimethylamido) diborane titanium 2-methyl-1,3-butadiene;
bis-2,6-diisopropylphenylamido-bis(dimethylamido) diborane titanium 2,3-dimethyl-1,3-butadiene;
bis-2,6-diisopropylphenylamido-bis(dimethylamido) diborane titanium 2-N,N-dimethylaminobenzyl;
bis-2,6-diisopropylphenylamido-bis(dimethylamido) diborane titanium allyl;
bis-2,6-diisopropylphenylamido-bis(dimethylamido) diborane titanium η$^4$-1,4-diphenyl-1,3-butadiene;
bis-2,6-diisopropylphenylamido-bis(dimethylamido) diborane titanium η$^4$-2,4-hexadiene;
bis-2,6-diisopropylphenylamido-bis(dimethylamido) diborane titanium η$^4$-1,4-dinaphthyl-1,3-butadiene;
bis-2,6-diisopropylphenylamido-bis(dimethylamido) diborane titanium η$^4$-1-phenyl-1,3-pentadiene;
bis-2,6-diisopropylphenylamido-bis(dimethylamido) diborane titanium η$^4$-1,3-pentadiene;
bis-2,6-diisopropylphenylamido-bis(bis(trimethylsilyl)amido)diborane titanium dichloride;
bis-2,6-diisopropylphenylamido-bis(bis(trimethylsilyl)amido)diborane titanium dimethyl;
bis-2,6-diisopropylphenylamido-bis(bis(trimethylsilyl)amido)diborane titanium bis-dimethylamide;
bis-2,6-diisopropylphenylamido-bis(bis(trimethylsilyl)amido)diborane titanium 2-methyl-1,3-butadiene;
bis-2,6-diisopropylphenylamido-bis(bis(trimethylsilyl)amido)diborane titanium 2,3-dimethyl-1,3-butadiene;
bis-2,6-diisopropylphenylamido-bis(bis(trimethylsilyl)amido)diborane titanium 2-N,N-dimethylaminobenzyl;
bis-2,6-diisopropylphenylamido-bis(bis(trimethylsilyl)amido)diborane titanium allyl;
bis-2,6-diisopropylphenylamido-bis(bis(trimethylsilyl)amido)diborane titanium η$^4$-1,4-diphenyl-1,3-butadiene;
bis-2,6-diisopropylphenylamido-bis(bis(trimethylsilyl)amido)diborane titanium η4-2,4-hexadiene;
bis-2,6-diisopropylphenylamido-bis(bis(trimethylsilyl)amido)diborane titanium η$^4$-1,4-dinaphthyl-1,3-butadiene;
bis-2,6-diisopropylphenylamido-bis(bis(trimethylsilyl)amido)diborane titanium η$^4$-1-phenyl-1,3-pentadiene;
bis-2,6-diisopropylphenylamido-bis(bis(trimethylsilyl)amido)diborane titanium η$^4$-1,3-pentadiene;
bis-2,6-diisopropylphenylamido-bis(diisopropylamido)diborane zirconium dichloride;
bis-2,6-diisopropylphenylamido-bis(diisopropylamido)diborane zirconium dimethyl;
bis-2,6-diisopropylphenylamido-bis(diisopropylamido)diborane zirconium bis-dimethylamide;
bis-2,6-diisopropylphenylamido-bis(diisopropylamido)diborane zirconium 2-methyl-1,3-butadiene;
bis-2,6-diisopropylphenylamido-bis(diisopropylamido)diborane zirconium 2,3-dimethyl-1,3-butadiene;

bis-2,6-diisopropylphenylamido-bis(diisopropylamido)diborane zirconium 2-N,N-dimethylaminobenzyl;
bis-2,6-diisopropylphenylamido-bis(diisopropylamido)diborane zirconium allyl;
bis-2,6-diisopropylphenylamido-bis(diisopropylamido)diborane zirconium η$^4$-1,4-diphenyl-1,3-butadiene;
bis-2,6-diisopropylphenylamido-bis(diisopropylamido)diborane zirconium η$^4$-2,4-hexadiene;
bis-2,6-diisopropylphenylamido-bis(diisopropylamido)diborane zirconium η$^4$-1,4-dinaphthyl-1,3-butadiene;
bis-2,6-diisopropylphenylamido-bis(diisopropylamido)diborane zirconium η$^4$-1-phenyl-1,3-pentadiene;
bis-2,6-diisopropylphenylamido-bis(diisopropylamido)diborane zirconium η$^4$-1,3-pentadiene;
bis-2-tert-butylphenylamido-bis(diisopropylamido)diborane titanium dichloride;
bis-2-tert-butylphenylamido-bis(diisopropylamido)diborane titanium dimethyl;
bis-2-tert-butylphenylamido-bis(diisopropylamido)diborane titanium bis-dimethylamide;
bis-2-tert-butylphenylamido-bis(diisopropylamido)diborane titanium 2-methyl-1,3-butadiene;
bis-2-tert-butylphenylamido-bis(diisopropylamido)diborane titanium 2,3-dimethyl-1,3-butadiene;
bis-2-tert-butylphenylamido-bis(diisopropylamido)diborane titanium 2-N,N-dimethylaminobenzyl,
bis-2-tert-butylphenylamido-bis(diisopropylamido)diborane titanium allyl;
bis-2-tert-butylphenylamido-bis(diisopropylamido)diborane titanium η$^4$-1,4-diphenyl-1,3-butadiene;
bis-2-tert-butylphenylamido-bis(diisopropylamido)diborane titanium η$^4$-2,4-hexadiene;
bis-2-tert-butylphenylamido-bis(diisopropylamido)diborane titanium η$^4$-1,4-dinaphthyl-1,3-butadiene;
bis-2-tert-butylphenylamido-bis(diisopropylamido) diborane titanium η$^4$-1-phenyl-1,3-pentadiene; and
bis-2-tert-butylphenylamido-bis(diisopropylamido)diborane titanium η$^4$-1,3-pentadiene.

A further preferred class of Group 4 transition metal complexes of the present invention are represented in previously defined formulas 4–9 wherein T is:

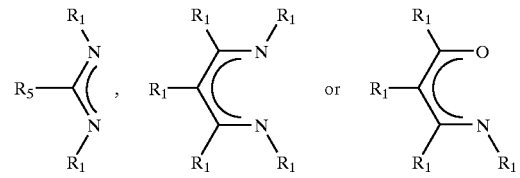

including such structures where two R$^1$ groups and R$^5$ are linked such as in 1,3,4,6,7,8, hexahydro-pyrimido[1,2-a]pyrimidinate, shown below:

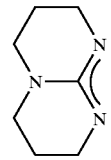

In the foregoing species, it is believed, without wishing to be bound by such belief, that the ligand group, T, is connected to Z via the heteroatoms thereof.

Specific, but not limiting, examples of the foregoing metal complexes included within the invention area:
N,N'-diisopropyl-phenyl-amidinate borane-bis-η$^5$-cyclopentadienylzirconium dichloride;

N,N'-diisopropyl-phenyl-amidinate borane-bis-$\eta^5$-cyclopentadienylzirconium dimethyl;
N,N'-diisopropyl-phenyl-amidinate borane-bis-$\eta^5$-cyclopentadienylzirconium bis-dimethylamide;
N,N'-diisopropyl-phenyl-amidinate borane-bis-$\eta^5$-cyclopentadienylzirconium 2-methyl-1,3-butadiene;
N,N'-diisopropyl-phenyl-amidinate borane-bis-$\eta^5$-cyclopentadienylzirconium 2,3-dimethyl-1,3-butadiene;
N,N'-diisopropyl-phenyl-amidinate borane-bis-$\eta^5$-cyclopentadienylzirconium 2-N,N-dimethylaminobenzyl;
N,N'-diisopropyl-phenyl-amidinate borane-bis-$\eta^5$-cyclopentadienylzirconium allyl;
N,N'-diisopropyl-phenyl-amidinate borane-bis-$\eta^5$-cyclopentadienylzirconium $\eta^4$-1,4-diphenyl-1,3-butadiene;
N,N'-diisopropyl-phenyl-amidinate borane-bis-$\eta^5$-cyclopentadienylzirconium $\eta^4$-2,4-hexadiene;
N,N'-diisopropyl-phenyl-amidinate borane-bis-$\eta^5$-cyclopentadienylzirconium $\eta^4$-1,4-dinaphthyl-1,3-butadiene;
N,N'-diisopropyl-phenyl-amidinate borane-bis-$\eta^5$-cyclopentadienylzirconium $\eta^4$-1-phenyl-1,3-pentadiene;
N,N'-diisopropyl-phenyl-amidinate borane-bis-$\eta^5$-cyclopentadienylzirconium $\eta^4$-1,3-pentadiene;
N,N'-diisopropyl-3-phenyl-1,3-diketimine borane-bis-$\eta^5$-cyclopentadienylzirconium dichloride;
N,N'-diisopropyl-3-phenyl-1,3-diketimine borane-bis-$\eta^5$-cyclopentadienylzirconium dimethyl;
N,N'-diisopropyl-3-phenyl-1,3-diketimine borane-bis-$\eta^5$-cyclopentadienylzirconium bis-dimethylamide;
N,N'-diisopropyl-3-phenyl-1,3-diketimine borane-bis-$\eta^5$-cyclopentadienylzirconium 2-methyl-1,3-butadiene;
N,N'-diisopropyl-3-phenyl-1,3-diketimine borane-bis-$\eta^5$-cyclopentadienylzirconium 2,3-dimethyl-1,3-butadiene;
N,N'-diisopropyl-3-phenyl-1,3-diketimine borane-bis-$\eta^5$-cyclopentadienylzirconium 2-N,N-dimethylaminobenzyl;
N,N'-diisopropyl-3-phenyl-1,3-diketimine borane-bis-$\eta^5$-cyclopentadienylzirconium alkyl;
N,N'-diisopropyl-3-phenyl-1,3-diketimine borane-bis-$\eta^5$-cyclopentadienylzirconium $\eta^4$-1,4-diphenyl-1,3-butadiene;
N,N'-diisopropyl-3-phenyl-1,3-diketimine borane-bis-$\eta^5$-cyclopentadienylzirconium $\eta^4$-2,4-hexadiene;
N,N'-diisopropyl-3-phenyl-1,3-diketimine borane-bis-$\eta^5$-cyclopentadienylzirconium $\eta^4$-1,4-dinaphthyl-1,3-butadiene;
N,N'-diisopropyl-3-phenyl-1,3-diketimine borane-bis-$\eta^5$-cyclopentadienylzirconium $\eta^4$-1-phenyl-1,3-pentadiene;
N,N'-diisopropyl-3-phenyl-1,3-diketimine borane-bis-$\eta^5$-cyclopentadienylzirconium $\eta^4$-1,3-pentadiene;
N,N'-diisopropyl-dimethylguanidine borane-bis-$\eta^5$-cyclopentadienylzirconium dichloride;
N,N'-diisopropyl-dimethylguanidinate borane-bis-$\eta^5$-cyclopentadienylzirconium dimethyl;
N,N'-diisopropyl-dimethylguanidinate borane-bis-$\eta^5$-cyclopentadienylzirconium bis-dimethylamide;
N,N'-diisopropyl-dimethylguanidinate borane-bis-$\eta^5$-cyclopentadienylzirconium 2-methyl-1,3-butadiene;
N,N'-diisopropyl-dimethylguanidinate borane-bis-$\eta^5$-cyclopentadienylzirconium 2,3-dimethyl-1,3-butadiene;
N,N'-diisopropyl-dimethylguanidinate borane-bis-$\eta^5$-cyclopentadienylzirconium 2-N,N-dimethylaminobenzyl;
N,N'-diisopropyl-dimethylguanidinate borane-bis-$\eta^5$-cyclopentadienylzirconium allyl;
N,N'-diisopropyl-dimethylguanidinate borane-bis-$\eta^5$-cyclopentadienylzirconium $\eta^4$-1,4-diphenyl-1,3-butadiene;
N,N'-diisopropyl-dimethylguanidinate borane-bis-$\eta^5$-cyclopentadienylzirconium $\eta^4$-2,4-hexadiene;
N,N'-diisopropyl-dimethylguanidinate borane-bis-$\eta^5$-cyclopentadienylzirconium $\eta^4$-1,4-dinaphthyl-1,3-butadiene;
N,N'-diisopropyl-dimethylguanidinate borane-bis-$\eta^5$-cyclopentadienylzirconium $\eta^4$-1-phenyl-1,3-pentadiene;
N,N'-diisopropyl-dimethylguanidinate borane-bis-$\eta^5$-cyclopentadienylzirconium $\eta^4$-1,3-pentadiene;
1,3,4,6,7,8-hexahydro-pyrimido[1,2-a]pyrimidinate borane-bis-$\eta^5$-inden-1-ylzirconium dichloride;
1,3,4,6,7,8-hexahydro-pyrimido[1,2-a]pyrimidinate borane-bis-$\eta^5$-inden-1-ylzirconium dimethyl;
1,3,4,6,7,8-hexahydro-pyrimido[1,2-a]pyrimidinate borane-bis-$\eta^5$-inden-1-ylzirconium bis-dimethylamide;
1,3,4,6,7,8-hexahydro-pyrimido[1,2-a]pyrimidinate borane-bis-$\eta^5$-inden-1-ylzirconium 2-methyl-1,3-butadiene;
1,3,4,6,7,8-hexahydro-pyrimido[1,2-a]pyrimidinate borane-bis-$\eta^5$-inden-1-ylzirconium 2,3-dimethyl-1,3-butadiene;
1,3,4,6,7,8-hexahydro-pyrimido[1,2-a]pyrimidinate borane-bis-$\eta^5$-inden-1-ylzirconium 2-N,N-dimethylaminobenzyl;
1,3,4,6,7,8-hexahydro-pyrimido[1,2-a]pyrimidinate borane-bis-$\eta^5$-inden-1-ylzirconium allyl;
1,3,4,6,7,8-hexahydro-pyrimido[1,2-a]pyrimidinate borane-bis-$\eta^5$-inden-1-ylzirconium $\eta^4$-1,4-diphenyl-1,3-butadiene;
1,3,4,6,7,8-hexahydro-pyrimido[1,2-a]pyrimidinate borane-bis-$\eta^5$-inden-1-ylzirconium $\eta^4$-2,4-hexadiene;
1,3,4,6,7,8-hexahydro-pyrimido[1,2-a]pyrimidinate borane-bis-$\eta^5$-inden-1-ylzirconium $\eta^4$-1,4-dinaphthyl-1,3-butadiene;
1,3,4,6,7,8-hexahydro-pyrimido[1,2-a]pyrimidinate borane-bis-$\eta^5$-inden-1-ylzirconium $\eta^4$-1-phenyl-1,3-pentadiene;
1,3,4,6,7,8-hexahydro-pyrimido[1,2-a]pyrimidinate borane-bis-$\eta^5$-inden-1-ylzirconium $\eta^4$-1,3-pentadiene;
N,N'-diisopropyl-phenyl-amidinate borane-bis-$\eta^5$-(2-methylinden-1-yl)zirconium dichloride;
N,N'-diisopropyl-phenyl-amidinate borane-bis-$\eta^5$-(2-methylinden-1-yl)zirconium dimethyl;
N,N'-diisopropyl-phenyl-amidinate borane-bis-$\eta^5$-(2-methylinden-1-yl)zirconium bis-dimethylamide;
N,N'-diisopropyl-phenyl-amidinate borane-bis-$\eta^5$-(2-methylinden-1-yl)zirconium 2-methyl-1,3-butadiene;
N,N'-diisopropyl-phenyl-amidinate borane-bis-$\eta^5$-(2-methylinden-1-yl)zirconium 2,3-dimethyl-1,3-butadiene;
N,N'-diisopropyl-phenyl-amidinate borane-bis-$\eta^5$-(2-methylinden-1-yl)zirconium 2-N,N-dimethylaminobenzyl;
N,N'-diisopropyl-phenyl-amidinate borane-bis-$\eta^5$-(2-methylinden-1-yl)zirconium allyl;
N,N'-diisopropyl-phenyl-amidinate borane-bis-$\eta^5$-(2-methylinden-1-yl)zirconium $\eta^4$-1,4-diphenyl-1,3-butadiene;
N,N'-diisopropyl-phenyl-amidinate borane-bis-$\eta^5$-(2-methylinden-1-yl)zirconium $\eta^4$-2,4-hexadiene;
N,N'-diisopropyl-phenyl-amidinate borane-bis-$\eta^5$-(2-methylinden-1-yl)zirconium $\eta^4$-1,4-dinaphthyl-1,3-butadiene;
N,N'-diisopropyl-phenyl-amidinate borane-bis-$\eta^5$-(2-methylinden-1-yl)zirconium $\eta^4$-1-phenyl-1,3-pentadiene;
N,N'-diisopropyl-phenyl-amidinate borane-bis-$\eta^5$-(2-methylinden-1-yl)zirconium $\eta^4$-1,3-pentadiene;
N,N'-bis-2,6-diisopropylphenyl-phenyl-amidinate borane-bis-$\eta^5$-(2-methyl-4-phenylinden-1-yl)zirconium dichloride;
N,N'-bis-2,6-diisopropylphenyl-phenyl-amidinate borane-bis-$\eta^5$-(2-methyl-4-phenylinden-1-yl)zirconium dimethyl;

N,N'-bis-2,6-diisopropylphenyl-phenyl-amidinate borane-bis-η⁵-(2-methyl-4-phenylinden-1-yl)zirconium bis-dimethylamide;
N,N'-bis-2,6-diisopropylphenyl-phenyl-amidinate borane-bis-η⁵-(2-methyl-4-phenylinden-1-yl)zirconium 2-methyl-1,3-butadiene;
N,N'-bis-2,6-diisopropylphenyl-phenyl-amidinate borane-bis-η⁵-(2-methyl-4-phenylinden-1-yl)zirconium 2,3-dimethyl-1,3-butadiene;
N,N'-bis-2,6-diisopropylphenyl-phenyl-amidinate borane-bis-η⁵-(2-methyl-4-phenylinden-1-yl)zirconium 2-N,N-dimethylaminobenzyl;
N,N'-bis-2,6-diisopropylphenyl-phenyl-amidinate borane-bis-η⁵-(2-methyl-4-phenylinden-1-yl)zirconium allyl;
N,N'-bis-2,6-diisopropylphenyl-phenyl-amidinate borane-bis-η⁵-(2-methyl-4-phenylinden-1-yl)zirconium η⁴-1,4-diphenyl-1,3-butadiene;
N,N'-bis-2,6-diisopropylphenyl-phenyl-amidinate borane-bis-η⁵-(2-methyl-4-phenylinden-1-yl)zirconium η⁴-2,4-hexadiene;
N,N'-bis-2,6-diisopropylphenyl-phenyl-amidinate borane-bis-η⁵-(2-methyl-4-phenylinden-1-yl)zirconium η⁴-1,4-dinaphthyl-1,3-butadiene;
N,N'-bis-2,6-diisopropylphenyl-phenyl-amidinate borane-bis-η⁵-(2-methyl-4-phenylinden-1-yl)zirconium η⁴-1-phenyl-1,3-pentadiene;
N,N'-bis-2,6-diisopropylphenyl-phenyl-amidinate borane-bis-η⁵-(2-methyl-4-phenylinden-1-yl)zirconium η⁴-1,3-pentadiene;
N,N'-bis-2,6-diisopropylphenyl-3-methyl-1,3-diketimine borane-bis-η⁵-(2-methyl-4-phenylinden-1-yl)zirconium dichloride;
N,N'-bis-2,6-diisopropylphenyl-3-methyl-1,3-diketimine borane-bis-η⁵-(2-methyl-4-phenylinden-1-yl)zirconium dimethyl;
N,N'-bis-2,6-diisopropylphenyl-3-methyl-1,3-diketimine borane-bis-η⁵-(2-methyl-4-phenylinden-1-yl)zirconium bis-dimethylamide;
N,N'-bis-2,6-diisopropylphenyl-3-methyl-1,3-diketimine borane-bis-η⁵-(2-methyl-4-phenylinden-1-yl)zirconium 2-methyl-1,3-butadiene;
N,N'-bis-2,6-diisopropylphenyl-3-methyl-1,3-diketimine borane-bis-η⁵-(2-methyl-4-phenylinden-1-yl)zirconium 2,3-dimethyl-1,3-butadiene;
N,N'-bis-2,6-diisopropylphenyl-3-methyl-1,3-diketimine borane-bis-η⁵-(2-methyl-4-phenylinden-1-yl)zirconium 2-N,N-dimethylaminobenzyl;
N,N'-bis-2,6-diisopropylphenyl-3-methyl-1,3-diketimine borane-bis-η⁵-(2-methyl-4-phenylinden-1-yl)zirconium allyl;
N,N'-bis-2,6-diisopropylphenyl-3-methyl-1,3-diketimine borane-bis-η⁵-(2-methyl-4phenylinden-1-yl)zirconium η⁴-1,4-diphenyl-1,3-butadiene;
N,N'-bis-2,6-diisopropylphenyl-3-methyl-1,3-diketimine borane-bis-η⁵-(2-methyl-4-phenylinden-1-yl)zirconium η⁴-2,4-hexadiene;
N,N'-bis-2,6-diisopropylphenyl-3-methyl-1,3-diketimine borane-bis-η⁵-(2-methyl-4-phenylinden-1-yl)zirconium η⁴-1,4-dinaphthyl-1,3-butadiene;
N,N'-bis-2,6-diisopropylphenyl-3-methyl-1,3-diketimine borane-bis-η⁵-(2-methyl-4-phenylinden-1-yl)zirconium η⁴-1-phenyl-1,3-pentadiene;
N,N'-bis-2,6-diisopropylphenyl-3-methyl-1,3-diketimine borane-bis-η⁵-(2-methyl-4-phenylinden-1-yl)zirconium η⁴-1,3-pentadiene;
bis(N,N'-diisopropyl-phenyl-amidinate)diborane-1,2-bis-η⁵-(2-methyl-4-phenylinden-1-yl)zirconium dichloride;
bis(N,N'-diisopropyl-phenyl-amidinate)diborane-1,2-bis-η⁵-(2-methyl-4-phenylinden-1-yl)zirconium dimethyl;
bis(N,N'-diisopropyl-phenyl-amidinate)diborane-1,2-bis-η⁵-(2-methyl-4-phenylinden-1-yl)zirconium bis-dimethylamide;
bis(n,N'-diisopropyl-phenyl-amidinate)diborane-1,2-bis-η⁵-(2-methyl-4-phenylinden-1-yl)zirconium 2-methyl-1,3-butadiene;
bis(N,N'-diisopropyl-phenyl-amidinate)diborane-1,2-bis-η⁵-(2-methyl-4-phenylinden-1-yl)zirconium 2,3-dimethyl-1,3-butadiene;
bis(N,N'-diisopropyl-phenyl-amidinate)diborane-1,2-bis-η⁵-(2-methyl-4-phenylinden-1-yl)zirconium 2-N,N-dimethylaminobenzyl;
bis(N,N'-diisopropyl-phenyl-amidinate)diborane-1,2-bis-η⁵-(2-methyl-4-phenylinden-1-yl)zirconium allyl;
bis(N,N'-diisopropyl-phenyl-amidinate)diborane-1,2-bis-η⁵-(2-methyl-4-phenylinden-1-yl)zirconium η⁴-1,4-diphenyl-1,3-butadiene;
bis(N,N'-diisopropyl-phenyl-amidinate)diborane-1,2-bis-η⁵-(2-methyl-4-phenylinden-1-yl)zirconium η⁴-2,4-hexadiene;
bis(N,N'-diisopropyl-phenyl-amidinate)diborane-1,2-bis-η⁵-(2-methyl-4-phenylinden-1-yl)zirconium η⁴-1,4-dinaphthyl-1,3-butadiene;
bis(N,N'-diisopropyl-phenyl-amidinate)diborane-1,2-bis-η⁵-(2-methyl-4-phenylinden-1-yl)zirconium η⁴-1-phenyl-1,3-pentadiene;
bis(N,N'-diisopropyl-phenyl-amidinate)diborane-1,2-bis-η⁵-(2-methyl-4-phenylinden-1-yl)zirconium η⁴-1,3-pentadiene;
bis(N,N'-diisopropyl-3-phenyl-1,3-diketimine)diborane-1,2-bis-η⁵-(2-methyl-4-phenylinden-1-yl)zirconium dichloride;
bis(N,N'-diisopropyl-3-phenyl-1,3-diketimine)diborane-1,2-bis-η⁵-(2-methyl-4-phenylinden-1-yl)zirconium dimethyl;
bis(N,N'-diisopropyl-3-phenyl-1,3-diketimine)diborane-1,2-bis-η⁵-(2-methyl-4-phenylinden-1-yl)zirconium bis-dimethylamide;
bis(N,N'-diisopropyl-3-phenyl-1,3-diketimine)diborane-1,2-bis-η⁵-(2-methyl-4-phenylinden-1-yl)zirconium 2-methyl-1,3-butadiene;
bis(N,N'-diisopropyl-3-phenyl-1,3-diketimine)diborane-1,2-bis-η⁵-(2-methyl-4-phenylinden-1-yl)zirconium 2,3-dimethyl-1,3-butadiene;
bis(N,N'-diisopropyl-3-phenyl-1,3-diketimine)diborane-1,2-bis-η⁵(2-methyl-4-phenylinden-1-yl)zirconium 2-N,N-dimethylaminobenzyl;
bis(N,N'-diisopropyl-3-phenyl-1,3-diketimine)diborane-1,2-bis-η⁵-(2-methyl-4-phenylinden-1-yl)zirconium allyl;
bis(N,N'-diisopropyl-3-phenyl-1,3-diketimine)diborane-1,2-bis-η⁵-(2-methyl-4-phenylinden-1-yl)zirconium η⁴-1,4-diphenyl-1,3-butadiene;
bis(N,N'-diisopropyl-3-phenyl-1,3-diketimine)diborane-1,2-bis-η⁵-(2-methyl-4-phenylinden-1-yl)zirconium η⁴-2,4-hexadiene;
bis(N,N'-diisopropyl-3-phenyl-1,3-diketimine)diborane-1,2-bis-η⁵-(2-methyl-4-phenylinden-1-yl)zirconium η⁴-1,4-dinaphthyl-1,3-butadiene;
bis(N,N'-diisopropyl-3-phenyl-1,3-diketimine)diborane-1,2-bis-η⁵-(2-methyl-4-phenylinden-1-yl)zirconium η⁴-1-phenyl-1,3-pentadiene;
bis(N,N'-diisopropyl-3-phenyl-1,3-diketimine)diborane-1,2-bis-η⁵-(2-methyl-4-phenylinden-1-yl)zirconium η⁴-1,3-pentadiene;
N,N'-diisopropyl-phenyl-amidinate borane-bis-η⁵-(2-methyl-4-naphthylinden-1-yl)zirconium dichloride;

N,N'-diisopropyl-phenyl-amidinate borane-bis-$\eta^5$-(2-methyl-4-naphthylinden-1-yl)zirconium dimethyl;
N,N'-diisopropyl-phenyl-amidinate borane-bis-$\eta^5$-(2-methyl-4-naphthylinden-1-yl)zirconium bis-dimethylamide;
N,N'-diisopropyl-phenyl-amidinate borane-bis-$\eta^5$-(2-methyl-4-naphthylinden-1-yl)zirconium 2-methyl-1,3-butadiene;
N,N'-diisopropyl-phenyl-amidinate borane-bis-$\eta^5$-(2-methyl-4-naphthylinden-1-yl)zirconium 2,3-dimethyl-1,3-butadiene;
N,N'-diisopropyl-phenyl-amidinate borane-bis-$\eta^5$-(2-methyl-4-naphthylinden-1-yl)zirconium 2-N,N-dimethylaminobenzyl;
N,N'-diisopropyl-phenyl-amidinate borane-bis-$\eta^5$-(2-methyl-4-naphthylinden-1-yl)zirconium allyl;
N,N'-diisopropyl-phenyl-amidinate borane-bis-$\eta^5$-(2-methyl-4-naphthylinden-1-yl)zirconium $\eta^4$-1,4-diphenyl-1,3-butadiene;
N,N'-diisopropyl-phenyl-amidinate borane-bis-$\eta^5$-(2-methyl-4-naphthylinden-1-yl)zirconium $\eta^4$-2,4-hexadiene;
N,N'-diisopropyl-phenyl-amidinate borane-bis-$\eta^5$-(2-methyl-4-naphthylinden-1-yl)zirconium $\eta^4$-1,4-dinaphthyl-1,3-butadiene;
N,N'-diisopropyl-phenyl-amidinate borane-bis-$\eta^5$-(2-methyl-4-naphthylinden-1-yl)zirconium $\eta^4$-1-phenyl-1,3-pentadiene;
N,N'-diisopropyl-phenyl-amidinate borane-bis-$\eta^5$-(2-methyl-4-naphthylinden-1-yl)zirconium $\eta^4$-1,3-pentadiene;
N,N'-diisopropyl-3-phenyl-1,3-diketimine borane-bis-$\eta^5$-(2-methyl-4-naphthylinden-1-yl)zirconium dichloride;
N,N'-diisopropyl-3-phenyl-1,3-diketimine borane-bis-$\eta^5$-(2-methyl-4-naphthylinden-1-yl)zirconium dimethyl;
N,N'-diisopropyl-3-phenyl-1,3-diketimine borane-bis-$\eta^5$-(2-methyl-4-naphthylinden-1-yl)zirconium bis-dimethylamide;
N,N'-diisopropyl-3-phenyl-1,3-diketimine borane-bis-$\eta^5$-(2-methyl-4-naphthylinden-1-yl)zirconium 2-methyl-1,3-butadiene;
N,N'-diisopropyl-3-phenyl-1,3-diketimine borane-bis-$\eta^5$-(2-methyl-4-naphthylinden-1-yl)zirconium 2,3-dimethyl-1,3-butadiene;
N,N'-diisopropyl-3-phenyl-1,3-diketimine borane-bis-$\eta^5$-(2-methyl-4-naphthylinden-1-yl)zirconium 2-N,N-dimethylaminobenzyl;
N,N'-diisopropyl-3-phenyl-1,3-diketimine borane-bis-$\eta^5$-(2-methyl-4-naphthylinden-1-yl)zirconium allyl;
N,N'-diisopropyl-3-phenyl-1,3-diketimine borane-bis-$\eta^5$-(2-methyl-4-naphthylinden-1-yl)zirconium $\eta^4$-1,4-diphenyl-1,3-butadiene;
N,N'-diisopropyl-3-phenyl-1,3-diketimine borane-bis-$\eta^5$-(2-methyl-4-naphthylinden-1-yl)zirconium $\eta^4$-2,4-hexadiene;
N,N'-diisopropyl-3-phenyl-1,3-diketimine borane-bis-$\eta^5$-(2-methyl-4-naphthylinden-1-yl)zirconium $\eta^4$-1,4-dinaphthyl-1,3-butadiene;
N,N'-diisopropyl-3-phenyl-1,3-diketimine borane-bis-$\eta^5$-(2-methyl-4-naphthylinden-1-yl)zirconium $\eta^4$-1-phenyl-1,3-pentadiene;
N,N'-diisopropyl-3-phenyl-1,3-diketimine borane-bis-$\eta^5$-(2-methyl-4-naphthylinden-1-yl)zirconium $\eta^4$-1,3-pentadiene;
bis-2,6-diisopropylphenylamido-bis(N,N'-diisopropylphenylamidinate)diborane titanium dichloride;
bis-2,6-diisopropylphenylamido-bis(N,N'-diisopropylphenylamidinate)diborane titanium dimethyl;
bis-2,6-diisopropylphenylamido-bis(N,N'-diisopropylphenylamidinate)diborane titanium bis-dimethylamide;
bis-2,6-diisopropylphenylamido-bis(N,N'-diisopropylphenylamidinate)diborane titanium 2-methyl-1,3-butadiene;
bis-2,6-diisopropylphenylamido-bis(N,N'-diisopropylphenylamidinate)diborane titanium 2,3-dimethyl-1,3-butadiene;
bis-2,6-diisopropylphenylamido-bis(N,N'-diisopropylphenylamidinate)diborane titanium 2-N,N-dimethylaminobenzyl;
bis-2,6-diisopropylphenylamido-bis(N,N'-diisopropylphenylamidinate)diborane titanium allyl;
bis-2,6-diisopropylphenylamido-bis(N,N'-diisopropylphenylamidinate)diborane titanium $\eta^4$-1,4-diphenyl-1,3-butadiene;
bis-2,6-diisopropylphenylamido-bis(N,N'-diisopropylphenylamidinate)diborane titanium $\eta^4$-2,4-hexadiene;
bis-2,6-diisopropylphenylamido-bis(N,N'-diisopropylphenylamidinate)diborane titanium $\eta^4$-1,4-dinaphthyl-1,3-butadiene;
bis-2,6-diisopropylphenylamido-bis(N,N'-diisopropylphenylamidinate)diborane titanium $\eta^4$-1-phenyl-1,3-pentadiene;
bis-2,6-diisopropylphenylamido-bis(N,N'-diisopropylphenylamidinate)diborane titanium $\eta^4$-1,3-pentadiene;
bis-2,6-diisopropylphenylamido-bis(N,N'-diisopropyl-3-phenyl-1,3-diketimine)diborane titanium dichloride;
bis-2,6-diisopropylphenylamido-bis(N,N'-diisopropyl-3-phenyl-1,3-diketimine)diborane titanium dimethyl;
bis-2,6-diisopropylphenylamido-bis(N,N'-diisopropyl-3-phenyl-1,3-diketimine)diborane titanium bis-dimethylamide;
bis-2,6-diisopropylphenylamido-bis(N,N'-diisopropyl-3-phenyl-1,3-diketimine)diborane titanium 2-methyl-1,3-butadiene;
bis-2,6-diisopropylphenylamido-bis(N,N'-diisopropyl-3-phenyl-1,3-diketimine)diborane titanium 2,3-dimethyl-1,3-butadiene;
bis-2,6-diisopropylphenylamido-bis(N,N'-diisopropyl-3-phenyl-1,3-diketimine)diborane titanium 2-N,N-dimethylaminobenzyl;
bis-2,6-diisopropylphenylamido-bis(N,N'-diisopropyl-3-phenyl-1,3-diketimine)diborane titanium allyl;
bis-2,6-diisopropylphenylamido-bis(N,N'-diisopropyl-3-phenyl-1,3-diketimine)diborane titanium $\eta^4$-1,4-diphenyl-1,3-butadiene;
bis-2,6-diisopropylphenylamido-bis(N,N'-diisopropyl-3-phenyl-1,3-diketimine)diborane titanium $\eta^4$-2,4-hexadiene;
bis-2,6-diisopropylphenylamido-bis(N,N'-diisopropyl-3-phenyl-1,3-diketimine)diborane titanium $\eta^4$-1,4-dinaphthyl-1,3-butadiene;
bis-2,6-diisopropylphenylamido-bis(N,N'-diisopropyl-3-phenyl-1,3-diketimine)diborane titanium $\eta^4$-1-phenyl-1,3-pentadiene; and
bis-2,6-diisopropylphenylamido-bis(N,N'-diisopropyl-3-phenyl-1,3-diketimine)diborane titanium $\eta^4$-1,3-pentadiene.

The skilled artisan will recognize that additional members of the foregoing list, such as those wherein boron is replaced by aluminum are also included within the invention. Moreover, it should also be recognized that the terms $\eta^5$ or $\eta^4$ may not accurately reflect the actual electronic distribution of the molecule under use conditions, and that molecules including lesser numbers of contributing atoms to the electronic delocation are intended to be included within such descriptions as well.

The most highly preferred metal complexes for use herein are:

dimethylamidoborane-bis($\eta^5$-cyclopentadienyl) zirconium dichloride, dimethylamidoboranebis($\eta^5$-inden-1-yl)zirconium dichloride, dimethylamidoborane-bis($\eta^5$-2-methyl-4-phenylinden-1-yl)zirconium dichloride, dimethylamidoborane-bis($\eta^5$-2-ethyl-4-phenylinden-1-yl)zirconium dichloride, dimethylamidoborane-bis($\eta^5$-2-isopropyl-4-phenylinden-1-yl)zirconium dichloride, dimethylamidoborane-bis($\eta^5$-2-methyl-4-bis(3,5-trifluoromethyl)phenylinden-1-yl)zirconium dichloride, dimethylamidoborane-bis($\eta^5$-3-t-butylinden-1-yl)zirconium dichloride, diisopropylamidoborane-bis($\eta^5$-cyclopentadienyl) zirconium dichloride, diisopropylamidoboranebis($\eta^5$-inden-1-yl)zirconium dichloride, diisopropylamidoborane-bis($\eta^5$-2-methyl-4-phenylinden-1-yl)zirconium dichloride, diisopropylamidoborane-bis($\eta^5$-2-ethyl-4-phenylinden-1-yl)zirconium dichloride, diisopropylamidoborane-bis($\eta^5$-2-isopropyl-4-phenylinden-1-yl)zirconium dichloride, diisopropylamidoborane-bis($\eta^5$-2-methyl-4-bis(3,5-trifluoromethyl)phenylinden-1-yl)zirconium dichloride, diisopropylamidoborane-bis($\eta^5$-3-t-butylinden-1-yl)zirconium dichloride, diphenylamidoborane-bis($\eta^5$-cyclopentadienyl) zirconium dichloride, diphenylamidoboranebis($\eta^5$-inden-1-yl)zirconium dichloride, diphenylamidoborane-bis($\eta^5$-2-methyl-4-phenylinden-1-yl)zirconium dichloride, diphenylamidoborane-bis($\eta^5$-2-ethyl-4-phenylinden-1-yl)zirconium dichloride, diphenylamidoborane-bis($\eta^5$-2-isopropyl-4-phenylinden-1-yl)zirconium dichloride, diphenylamidoborane-bis($\eta^5$-2-methyl-4-bis(3,5-trifluoromethyl)phenylinden-1-yl)zirconium dichloride, diphenylamidoborane-bis($\eta^5$-3-t-butylinden-1-yl)zirconium dichloride, dimethylamidoborane-bis($\eta^5$-cyclopentadienyl) zirconium 1,4-diphenyl-1,3-butadiene, dimethylamidoboranebis($\eta^5$-inden-1-yl)zirconium 1,4-diphenyl-1,3-butadiene, dimethylamidoborane-bis($\eta^5$-2-methyl-4-phenylinden-1-yl)zirconium 1,4-diphenyl-1,3-butadiene, dimethylamidoborane-bis($\eta^5$-2-ethyl-4-phenylinden-1-yl)zirconium 1,4-diphenyl-1,3-butadiene, dimethylamidoborane-bis($\eta^5$-2-isopropyl-4-phenylinden-1-yl)zirconium 1,4-diphenyl-1,3-butadiene, dimethylamidoborane-bis($\eta^5$-2-methyl-4-bis(3,5-trifluoromethyl)phenylinden-1-yl)zirconium 1,4-diphenyl-1,3-butadiene, dimethylamidoborane-bis($\eta^5$-3-t-butylinden-1-yl)zirconium 1,4-diphenyl-1,3-butadiene, diisopropylamidoborane-bis($\eta^5$-cyclopentadienyl) zirconium 1,4-diphenyl-1,3-butadiene, diisopropylamidoboranebis($\eta^5$-inden-1-yl)zirconium 1,4-diphenyl-1,3-butadiene, diisopropylamidoborane-bis($\eta^5$-2-methyl-4-phenylinden-1-yl)zirconium 1,4-diphenyl-1,3-butadiene, diisopropylamidoborane-bis($\eta^5$-2-ethyl-4-phenylinden-1-yl)zirconium 1,4-diphenyl-1,3-butadiene, diisopropylamidoborane-bis($\eta^5$-2-isopropyl-4-phenylinden-1-yl)zirconium 1,4-diphenyl-1,3-butadiene, diisopropylamidoborane-bis($\eta^5$-2-methyl-4-bis(3,5-trifluoromethyl)phenylinden-1-yl)zirconium 1,4-diphenyl-1,3-butadiene, diisopropylamidoborane-bis($\eta^5$-3-t-butylinden-1-yl)zirconium 1,4-diphenyl-1,3-butadiene, diphenylamidoborane-bis($\eta^5$-cyclopentadienyl) zirconium 1,4-diphenyl-1,3-butadiene, diphenylamidoboranebis($\eta^5$-inden-1-yl)zirconium 1,4-diphenyl-1,3-butadiene, diphenylamidoborane-bis($\eta^5$-2-methyl-4-phenylinden-1-yl)zirconium 1,4-diphenyl-1,3-butadiene, diphenylamidoborane-bis($\eta^5$-2-ethyl-4-phenylinden-1-yl)zirconium 1,4-diphenyl-1,3-butadiene, diphenylamidoborane-bis($\eta^5$-2-isopropyl-4-phenylinden-1-yl)zirconium 1,4-diphenyl-1,3-butadiene, diphenylamidoborane-bis($\eta^5$-2-methyl-4-bis(3,5-trifluoromethyl)phenylinden-1-yl)zirconium 1,4-diphenyl-1,3-butadiene, or diphenylamidoborane-bis($\eta^5$-3-t-butylinden-1-yl)zirconium 1,4-diphenyl-1,3-butadiene.

In general the complexes of the current invention can be prepared by first converting the ligands represented in formulas 1a and 2a to a dianionic salt (where $R^4$ is H) via reaction with an alkyl lithium, Grignard reagent, or alkali metal hydride such as NaH or KH. The dianionic ligand derivative is then reacted with a metal complex precursor such as $MY^3{}_4$, $MY^3{}_3$, or $MY^3{}_2$ (and the corresponding Lewis base adducts), where $Y^3$ is defined as above. Alternatively, reactions employing the neutral ligand, where $R^4$ is hydrogen, in combination with the metal precursors $M(NR^3{}_2)_4$ or $MR^3{}_4$ can be employed. These reactions are conducted in an inert solvent such as a hydrocarbon solvent or a etheral solvent in the temperature range of –100° C. to 150° C.

An especially useful metal complex precursor reagent corresponds to the formula 3:

Formula 3

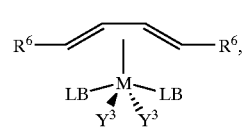

wherein M is zirconium, $R^1$ and LB are as previously defined and $Y^3$ each occurrence is chloride. Employment of this precursor in the reaction with ligands of this invention renders the resulting metal complex in high racemic purity, which is especially useful in the stereospecific polymerization of a-olefins.

Alternatively, where $R^4$ in structures of formula 1a and 2a is a trimethylsilyl group the ligand can be reacted directly with any of the above metal complex precursors of formula 3, employing similar reaction conditions.

The recovery of the desired Group 4 transition metal complex is accomplished by separation of the product from any alkali metal or alkaline earth metal salts and devolatilization of the reaction medium. Extraction into a secondary solvent may be employed if desired. Alternatively, if the desired product is an insoluble precipitate, filtration or other separation techniques may be employed. Final purification, if required, may be accomplished by recrystallization from an inert solvent, employing low temperatures if needed.

The complexes are rendered catalytically active by combination with activating cocatalysts or use of activating techniques that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C^{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, WO 99/15534, and U.S. Ser. No. 09/251,664, filed Feb. 17, 1999.

Combinations of neutral Lewis acids, especially the combination of a trialkylaluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluorophenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*-H)_d^+(A)^{d-}$$

wherein:

L* is a neutral Lewis base;

$(L^*-H)^+$ is a conjugate Bronsted acid of L*;

$A^{d-}$ is a noncoordinating, compatible anion having a charge of d−, and d is an integer from 1 to 3.

More preferably $A^{d-}$ corresponds to the formula: $[M'Q_4]^-$; wherein:

M' is boron or aluminum in the +3 formal oxidation state; and

Q independently each occurrence is selected from hydride, dialkylamido, halide, hydrocarbyl, hydrocarbyloxide, halo-substituted hydrocarbyl, halo-substituted hydrocarbyloxy, and halo-substituted silyl-hydrocarbyl radicals (including perhalogenated hydrocarbyl-perhalogenated hydrocarbyloxy- and per-halogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred embodiment, d is one, that is, the counter ion has a single negative charge and is $A^-$. Activating cocatalysts comprising boron which are particularly useful in the preparation of catalysts of this invention may be represented by the following general formula:

$$(L^*-H)^{30}(BQ_4)^-;$$

wherein:

L* is as previously defined;

B is boron in a formal oxidation state of 3; and

Q is hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Preferred Lewis base salts are ammonium salts, more preferably trialkylammonium salts containing one or more $C_{12-40}$ alkyl groups. Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:

trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(sec-butyl)ammonium tetrakis(pentafluorophenyl) borate, N,N-dimethylanilinium tetrakis(pentafluorophenyl) borate, N,N-dimethylanilinium n-butyltris(pentafluorophenyl) borate, N,N-dimethylanilinium benzyltris(pentafluorophenyl) borate, N,N-dimethylanilinium tetrakis(4-(t-butyldimethylsilyl)-2,3,5,6-tetrafluorophenyl) borate, N,N-dimethylanilinium tetrakis(4-(triisopropylsilyl)-2,3,5,6-tetrafluorophenyl) borate, N,N-dimethylanilinium pentafluorophenoxytris(pentafluorophenyl) borate, N,N-diethylanilinium tetrakis(pentafluorophenyl) borate, N,N-dimethyl-2,4,6-trimethylanilinium tetrakis (pentafluorophenyl) borate,
dimethyltetradecylammonium tetrakis (pentafluorophenyl) borate,
dimethylhexadecylammonium tetrakis (pentafluorophenyl) borate,
dimethyloctadecylammonium tetrakis (pentafluorophenyl) borate,
methylditetradecylammonium tetrakis (pentafluorophenyl) borate,
methylditetradecylammonium (hydroxyphenyl)tris (pentafluorophenyl) borate,
methylditetradecylammonium (diethylaluminoxyphenyl) tris(pentafluorophenyl) borate,
methyldihexadecylammonium tetrakis (pentafluorophenyl) borate,
methyldihexadecylammonium (hydroxyphenyl)tris (pentafluorophenyl) borate,
methyldihexadecylammonium (diethylaluminoxyphenyl) tris(pentafluorophenyl) borate,
methyldioctadecylammonium tetrakis (pentafluorophenyl) borate,
methyldioctadecylammonium (hydroxyphenyl)tris (pentafluorophenyl) borate,
methyldioctadecylammonium (diethylaluminoxyphenyl) tris(pentafluorophenyl) borate,
mixtures of the foregoing, dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis (pentafluorophenyl) borate, and
dioctadecylammonium tetrakis(pentafluorophenyl) borate;

tri-substituted phosphonium salts such as:
triphenylphosphonium tetrakis(pentafluorophenyl) borate,
methyldioctadecylphosphonium tetrakis (pentafluorophenyl) borate, and
tris(2,6-dimethylphenyl)phosphonium tetrakis (pentafluorophenyl) borate;

di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;

di-substituted sulfonium salts such as:
di(o-tolyl)sulfonium tetrakis(pentafluorophenyl) borate, and
methylcotadecylsulfonium tetrakis(pentafluorophenyl) borate.

Preferred (L*–H)$^+$ cations are methyldioctadecylammonium and dimethyloctadecylammonium.

Another suitable ion forming, activating cocatalyst comprises a salt of a cationic oxidizing agent and a noncoordinating, compatible anion represented by the formula:

$$(OX^{e+})_d(A^{d-})_e,$$

wherein:
Ox$^{e+}$ is a cationic oxidizing agent having a charge of e+;
e is an integer from 1 to 3; and
A$^{d-}$ and d are as previously defined.

Examples of cationic oxidizing agents include: ferrocenium, hydrocarbyl-substituted ferrocenium, Ag$^+$ or Pb$^{+2}$. Preferred embodiments of A$^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

$$ⓒ^+A^-$$

wherein:
ⓒ$^+$ is a C$_{1-20}$ carbenium ion; and
A$^-$ is as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula:

$$R_3Si(X')_q{}^+A^-$$

wherein:
R is C$_{1-10}$ hydrocarbyl, and X', q and A$^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in J. Chem Soc. Chem. Comm., 1993, 383–384, as well as Lambert, J. B., et al., Organometallics, 1994, 13, 2430–2443. The use of the above silylium salts as activating cocatalysts for addition polymerization catalysts is disclosed in U.S. Ser. No. 304,314, filed Sep. 12, 1994, published in equivalent form as WO96/08519 on Mar. 21, 1996, the teachings of which are herein incorporated by reference.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference.

Another class of suitable catalyst activators are expanded anionic compounds corresponding to the formula: $(A^{1+a^1})_{b^1}(Z^1J^1{}_j^1)^{-c^1}{}_{d^1}$, wherein:
A$^1$ is a cation of charge +a$^1$,
Z$^1$ is an anion group of from 1 to 50, preferably 1 to 30 atoms, not counting hydrogen atoms, further containing two or more Lewis base sites;
J$^1$ independently each occurrence is a Lewis acid coordinated to at least one Lewis base site of Z$^1$, and optionally two or more such J$^1$ groups may be joined together in a moiety having multiple Lewis acidic functionality,
j$^1$ is a number from 2 to 12 and
a$^1$, b$^1$, c$^1$, and d$^1$ are integers from 1 to 3, with the proviso that a$^1$×b$^1$ is equal to c$^1$×d$^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

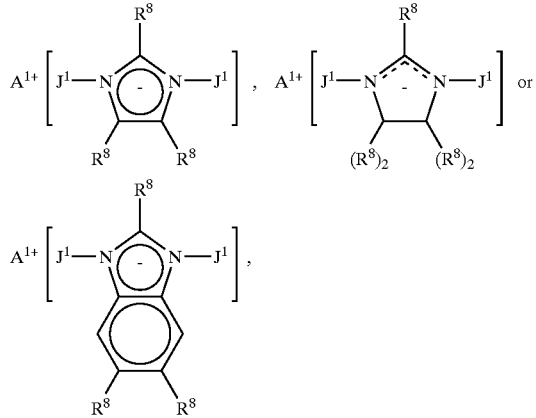

wherein:
$A^{1+}$ is a monovalent cation as previously defined, and preferably is a trihydrocarbyl ammonium cation, containing one or two $C_{10-40}$ alkyl groups, especially the methylbis(tetradecyl)ammonium- or methylbis(octadecyl)ammonium- cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris(pentafluorophenyl)aluminane.

Examples of these catalyst activators include the trihydrocarbylammonium-, especially, methylbis(tetradecyl) ammonium- or methylbis(octadecyl) ammonium- salts of:
bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide,
bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide,
bis(tris(pentafluorophenyl)alumane)-4,5-bis(undecyl)imidazolide,
bis(tris(pentafluorophenyl)alumane)-4,5-bis(heptadecyl)imidazolide,
bis(tris(pentafluorophenyl)alumane)imidazolinide,
bis(tris(pentafluorophenyl)alumane)-2-undecylimidazolinide,
bis(tris(pentafluorophenyl)alumane)-2-heptadecylimidazolinide,
bis(tris(pentafluorophenyl)alumane)-4,5-bis(undecyl)imidazolinide,
bis(tris(pentafluorophenyl)alumane)-4,5-bis(heptadecyl)imidazolinide,
bis(tris(pentafluorophenyl)alumane)-5,6-dimethylbenzimidazolide, and
bis(tris(pentafluorophenyl)alumane)-5,6-bis(undecyl)benzimidazolide.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in a molar ratio to the metal complex from 0.9:1 to 3:1, and preferably in approximately an equimolar quantity with the metal complex, that is from 1.1 to 1.5:1.

The catalyst composition may be prepared and employed as a heterogeneous catalyst by adsorbing, depositing or chemically attaching the requisite components on an inert inorganic or organic particulated solid. Examples of such solids include, silica, silica gel, alumina, clays, expanded clays (aerogels), aluminosilicates, triakylaluminum compounds, and organic or inorganic polymeric materials, especially polyolefins. In an preferred embodiment, a heterogeneous catalyst is prepared by reacting an inorganic compound, preferably a tri($C_{1-4}$ alkyl aluminum compound, with an activating cocatalyst, especially an ammonium salt of a hydroxyaryl(trispentafluorophenyl)borate, such as an ammonium salt of (4-hydroxy-3,5-ditertiarybutylphenyl) tris-(pentafluorophenyl)borate or (4-hydroxyphenyl)-tris(pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

The catalysts, preferably supported in any of the foregoing methods, may be used to polymerize ethylenically and/or acetylenically unsaturated monomers having from 2 to 8 carbon atoms either alone or in combination in the gas phase. Preferred monomers include the $C_{2-6}$ α-olefins especially ethylene, propylene, isobutylene, 1-butene, 1-pentene, 1-hexene, 3-methyl-1-pentene, 4-methyl-1-pentene, and mixtures thereof. Other preferred monomers include 1,3-butadiene, ethylidenenorbornene, and mixtures thereof. Preferred monomers include ethylene, or a mixture of $C_{2-6}$ α-olefins.

Long chain macromolecular α-olefins are vinyl terminated polymeric remnants formed in situ, especially during continuous or semi-continuous polymerization reactions. Under suitable processing conditions such long chain macromolecular units are readily polymerized into the polymer product along with ethylene and other short chain olefin monomers to give small quantities of long chain branching in the resulting polymer. Such polymers possess improved rehological properties, especially improved extrusion characteristics compared to polymers containing relatively less long chain branching. One analytical measurement that may indicate the presence of long chain branching in an olefin polymer is the presence of an elevated I10/I2 or an elevated I21/I2 value, while possessing narrow molecular weight distribution as determined by Mw/Mn, compared to polymers not having long chain branching. Preferred are such polymers having Mw/Mn less than 3.5, especially less than 3.0, especially less than 2.8 and I10/I2 of greater than 10, preferably greater than 20, most preferably greater than 30.

In general, the polymerization may be accomplished at conditions well known in the prior art for gas phase polymerization reactions, that is, temperatures from 0–250° C., preferably 60 to 150° C., more preferably from 70 to 110° C. and pressures from atmospheric to 10,000 atmospheres. A support, especially silica, alumina, or a polymer (especially poly(tetrafluoroethylene) or a polyolefin) may be employed, and desirably is employed to obtain a desired, particulated, polymer morphology. The support is preferably employed in an amount to provide a weight ratio of catalyst (based on metal):support from 1:100,000 to 1:10, more preferably from 1:50,000 to 1:20, and most preferably from 1:10,000 to 1:30. In most polymerization reactions the molar ratio of catalyst:polymerizable compounds employed is from $10^{-12}$:1 to $10^{-1}$:1, more preferably from $10^{-9}$:1 to $10^{-5}$:1.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

Gas phase processes for the polymerization of olefins, especially the homopolymerization and copolymerization of ethylene and propylene, and the copolymerization of ethylene with higher α-olefins are well known in the art. The polymerization may be carried out as a batchwise or a continuous polymerization process A continuous process is preferred, in which event catalyst, ethylene, comonomer, and optionally solvent are continuously supplied to the reaction zone and polymer product continuously removed, or intermittently removed therefrom. The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

Cooling of the reactor may be provided by the use of recycle gas, which is fed as a volatile liquid to the bed to provide an evaporative cooling effect. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid (or can be condensed to provide such a liquid) this can be fed to the bed to provide an evaporative cooling effect. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will condense from the gas. This liquid is desirably recycled continuously to the fluidized bed. It is possible to recycle the condensed liquid to the bed as liquid droplets carried in the recycle gas stream. This type of process is described, for example in EP-A-089691; U.S. Pat. No. 4,543,399; WO 94/25495 and U.S. Pat. No. 5,352,749. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032.

The polymer is produced directly in the fluidized bed by catalyzed copolymerization of the monomer and one or more comonomers on the fluidized particles of catalyst, supported catalyst or prepolymer within the bed. Start-up of the polymerization reaction is desirably achieved using a bed of preformed polymer particles, which are preferably similar to the target polyolefin, and conditioning the bed according to techniques that are well known in the art. Such processes are used commercially on a large scale for the manufacture of high density polyethylene (HDPE), medium density polyethylene (MDPE), linear low density polyethylene (LLDPE) and polypropylene.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a larger cross-sectional area than the fluidized bed and wherein fine particles entrained in the gas stream have an opportunity to gravitate back into the bed. It can also be advantageous to use a cyclone to remove fine particles from the hot gas stream. The gas is then normally recycled to the bed by means of a blower or compressor and one or more heat exchangers to strip the gas of the heat of polymerization. The produced polymer is discharged continuously or discontinuously from the fluidized bed as desired.

Typically the molar ratio of comonomer to monomer used in the polymerization depends upon the desired density for the composition being produced and is desirably about 0.5 or less. Desirably, when producing materials with a density range of from 0.91 to 0.93 the comonomer to monomer ratio is less than 0.2, preferably less than 0.05, even more preferably less than 0.02, and may even be less than 0.01. Hydrogen may be added to the reaction in order to control the molecular weight and melt index of the polymer. Typically, the ratio of hydrogen to monomer is less than about 0.5, preferably less than 0.2, more preferably less than 0.05, even more preferably less than 0.01.

A number of patents and patent applications describe gas phase processes which are adaptable for use in the process of this invention, particularly, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,541,270, EP-A-659,773; EP-A-692,500; WO 94/29032, WO 94/25497, WO 94/25495, WO 94/28032; WO 95/13305; WO 94/26793; and WO 95/07942.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. The term "overnight", if used, refers to a time of approximately 16–18 hours, the term "room temperature", refers to a temperature of about 20–25° C., and the term "mixed alkanes" refers to a commercially obtained mixture of $C^{6-8}$ aliphatic hydrocarbons available under the trade designation Isopar E®, from Exxon Chemicals Inc.

$^1$H (300 MHz) and $^{13}$C NMR (75 MHz) spectra were recorded on a Varian XL-300 spectrometer. $^1$H and $^{13}$C NMR spectra are referenced to the residual solvent peaks and are reported in ppm relative to tetramethylsilane. All J values are given in Hz. Tetrahydrofuran (THF), diethylether, toluene, and hexane were used following passage through double columns charged with activated alumina and a purifying catalyst (Q-5® available from Englehardt Chemicals Inc.) The compounds $BCl_3$-$SMe_2$, $BBr_3$-$SMe_2$, $(NMe_2)_3$, n-BuLi were all used as purchased from Aldrich. The compound $TiCl_3(THF)_3$ was prepared as described in the literature. All syntheses were performed under dry nitrogen or argon atmospheres using a combination of glove box and high vacuum techniques.

Example 1

Dichloro-[1,2-Bis(2,6-diisopropylanilide)-1,2-bis(dimethylamido)diborane]titanium

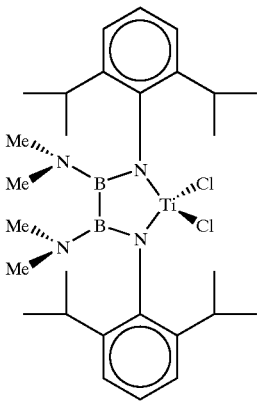

1A) Preparation of Chlorobis(dimethylamido)borane, (modification of Chavant, P. Y.; Vaultier, M. *J. Organomet. Chem.* 1993, 455, 37–46)

$BCl_3$-$SMe_2$ (62.000 g, 345.78 mmol) and $B(NMe_2)_3$ (98.921 g, 691.56 mmole) were stirred together at room temperature overnight under a nitrogen bubbler. The mixture was then heated to reflux for one hour to drive off any residual $SMe_2$. Allowing the pale yellow liquid to stir to room temperature resulted in the isolation of the desired product cleanly (44.979 g, 99.9 percent yield).

$^1$H NMR ($C_6D_6$): δ 2.49 (s, 12 H). $^{13}$C NMR ($C_6D_6$): δ 39.86.

1B) Preparation of Tetrakis(dimethylamido)diborane (modification of Noth, H; Meister, W. *Z Naturforsch., Teil B* 1962, 17, 714)

Chlorobis(dimethylamido)borane (30.000 g, 223.19 mmol) was refluxed in hexane (200 ml) as Na/K alloy [Na (1.539 g, 66.96 mmol)/8.726 g K (8.726 g, 223.19 mmol)] was added dropwise to the solution. After the first several drops the reaction initiated as evidenced by a sudden increase in the reflux. The heat was then turned off and the alloy added slowly so as to maintain a reflux. After the addition was complete, the reaction mixture was heated to reflux for an additional hour and then stirred at room temperature for three hours. The mixture was then filtered through a pad of diatomaceous earth and the volatiles removed resulting in the isolation of a yellow liquid. Fractional vacuum distillation resulted in the isolation of the desired compound as a pale yellow liquid (7.756 g, 35.1 percent yield).

$^1$H NMR ($C_6D_6$): δ 2.74 (s, 24 H). $^{13}$C NMR ($C_6D_6$): δ 41.34.

1C) Preparation of Bis(dimethylamido)diborondichloride (modification of Noth, H; Meister, W. *Z. Naturforsch., Teil B* 1962, 17, 714)

Tetrakis(dimethylamido)diborane (7.76 g, 39.29 mmol) was stirred in diethylether (100 ml) at −78° C. as HCl (157 mmol, 157 ml of 1.0 M solution in diethylether) was added dropwise. This mixture was then allowed to stir for six hours at room temperature. After the reaction period the volatiles were removed and the residue extracted and filtered using hexane. Removal of the hexane resulted in the isolation of a yellow oil. Fractional vacuum distillation resulted in the isolation of the desired compound as a pale yellow liquid (4.72 g, 66.7 percent yield).

$^1$H NMR ($C_6D_6$): δ 2.40 (s, 6 H), 2.50 (s, 6 H). $^{13}$C NMR ($C_6D_6$): δ 37.62, 41.78.

1D) Preparation of 2,6-Diisopropylaniline, lithium salt n-BuLi (56.4 mmol, 35.3 ml of 1.60 M solution in hexane) was added dropwise to a solution of 2,6-diisopropylaniline (10.0 g, 56.4 mmol) in hexane (100 ml). This mixture was allowed to stir for 3 hours during which time a white precipitate formed. After the reaction period the mixture was filtered and the white salt washed with hexane and dried under vacuum and used without further purification or analysis (9.99 g, 96.7 percent).

1E) Preparation of 1,2-Bis(2,6-diisopropylanilide)-1,2-bis(dimethylamido) diborane Bis(dimethylamido)diborondichloride (2.35 g, 13.0 mmol) in diethylether (10 ml) was added dropwise to a solution of 2,6-diisopropylaniline, lithium salt (4.77 g, 26.0 mmol) in diethylether (50 ml) at 0° C. This mixture was then allowed to stir overnight at room temperature. After the reaction period the volatiles were removed and the residue extracted and filtered using hexane. Removal of the hexane resulted in the isolation of a the desired product as a white solid (5.32 g, 88.9 percent yield).

$^1$H NMR ($C_6D_6$, RT): δ 0.9–1.4 (br m, 24 H), 2.3 (s, 6 H), 2.8 (s, 6 H), 3.7 (s, 2 H), 7.0 (br s, 6 H).

1F) Preparation of 1,2-Bis(2,6-diisopropylanilide)-1,2-bis(dimethylamido) diborane, dilithium salt 1,2-Bis(2,6-diisopropylanilide)-1,2-bis(dimethylamido) diborane (1.82 g, 3.95 mmol) was stirred in hexane (75 ml) as n-BuLi (7.91 mmol, 4.94 ml of 1.60 M solution in hexane) was added dropwise. This mixture was then allowed to stir overnight. After the reaction period the mixture was filtered and the salt washed well with hexane and dried under vacuum resulting in the isolation of the desired product as a white powder (1.69 g, 90.4 percent yield).

1G) Preparation of Dichloro-[1,2-Bis(2,6-diisopropylanilide)-1,2-bis(dimethylamido)diborane]titanium 1,2-Bis(2,6-diisopropylanilide)-1,2-bis(dimethylamido) diborane, dilithium salt (0.60 g, 1.27 mmol) in THF (20 ml) was added dropwise to a slurry of $TiCl_3(THF)_3$ (0.47 g, 1.27 mmol) in THF (50 ml) at 0° C. This mixture was then allowed to stir at room temperature for 45 minutes. $PbCl_2$ (0.177 g, 0.640 mmol) was then added as a solid and the mixture allowed to stir for an additional 30 minutes. After the reaction period the volatiles were removed and the residue extracted and filtered using hexane. Concentration of the hexane and cooling to −10° C. overnight resulted in the formation of orange X-ray quality crystals (0.156 g, 21.3 percent yield).

$^1$H NMR (C$_6$D$_6$): δ 1.23 (d, $^3$J$_{HH}$=6.6 Hz, 6 H), 1.45 (d, $^3$J$_{HH}$=6.6 Hz, 6 H), 2.17 (s, 6 H), 2.76 (s, 6 H), 3.53 (septet, $^3$J$_{HH}$=6.6 Hz, 4 H), 7.11 (s, 6 H).

Example 2

Dichloro [1,2-Bis(2,6-diisopropylanilide)-1,2-bis (dimethylamido) diborane]titanium (Alternated Preparation)

2A) Preparation of Chlorobis(dimethylamido)borane.

BCl$_3$-SMe$_2$ (62.000 g, 345.78 mmol) and B(NMe$_2$)$_3$ (98.921 g, 691.56 mmol) were stirred together at room temperature overnight under a nitrogen bubbler. The mixture was then heated to reflux for one hour to drive off any residual SMe$_2$. Allowing the pale yellow liquid to stir to room temperature resulted in the isolation of the desired product (139.436 g, 93.3 percent yield). $^1$H NMR (C$_6$D$_6$): δ 2.49 (s, 12 H). $^{13}$C NMR (C$_6$D$_6$): δ 39.86.

2B) Preparation of Tetrakis(dimethylamido)diborane via ClB(NMe)$_2$.

Chlorobis(dimethylamido)borane (30.000 g, 223.19 mmol) was refluxed in hexane (200 ml) as Na/K alloy [Na (1.539 g, 66.96 mmol)/8.726 g K (8.726 g, 223.19 mmol)] was added dropwise to the solution. After the first several drops the reaction initiated as evidenced by a sudden increase in the reflux. The heat was then turned off and the alloy added slowly so as to maintain a reflux. After the addition was complete, the reaction mixture was heated to reflux for an additional hour and then stirred at room temperature for three hours. The mixture was then filtered through a diatomaceous earth pad and the volatile components were removed resulting in the isolation of a yellow liquid. Fractional vacuum distillation resulted in the isolation of the desired compound as a pale yellow liquid (7.756 g, 35.1 percent yield). $^1$H NMR (C$_6$D$_6$): δ 2.73 (s, 24 H). $^{13}$C NMR (C$_6$D$_6$): δ 41.37.

2C) Preparation of Tetrakis(dimethylamido)diborane via Bis (catecholato)diboron.

Lithium dimethylamide (10.70 g, 210.0 mmol) was added slowly as a solid to a solution of bis(catecholato)diboron (10.00 g, 42.00 mmol) in diethylether (200 ml) at –20° C. This mixture was then allowed to stir for an additional 40 hours at room temperature. After the reaction period the ether was removed under vacuum and the residue extracted and filtered using hexane. Removal of the hexane resulted in the isolation of a yellow oil. Fractional vacuum distillation resulted in the isolation of the desired compound as a pale yellow liquid (5.493 g, 66.0 percent yield).

2D) Preparation of Bis(dimethylamido)diborondichloride.

Tetrakis(dimethylamido)diborane (7.756 g, 39.19 mmol) was stirred in diethylether (100 ml) at –78° C. as HCl (156.75 mmol, 156.75 ml of 1.0 M solution in diethylether) was added dropwise. This mixture was then allowed to stir for six hours at room temperature. After the reaction period the volatile components were removed and the residue extracted and filtered using hexane. Removal of the hexane resulted in the isolation of a yellow oil. Fractional vacuum distillation resulted in the isolation of the desired compound as a pale yellow liquid (4.722 g, 66.7 percent yield). $^1$H NMR (C$_6$D$_6$): δ 2.40 (s, 6 H), 2.50 (s, 6 H). $^{13}$C NMR (C$_6$D$_6$): δ 37.62, 41.78.

2E) Preparation of 2,6-Diisopropylaniline, lithium salt.

n-BuLi (56.40 mmol, 35.25 ml of 1.6 M solution in hexane) was added dropwise to a solution of 2,6-diisopropylaniline (10.00 g, 56.40 mmol) in hexane (100 ml). This mixture was allowed to stir for 3 hours during which time a white precipitate formed. After the reaction period the mixture was filtered and the white salt washed with hexane and dried under vacuum and used without further purification or analysis (9.988 g, 96.7 percent yield).

2F) Preparation of 1,2-Bis(2,6-diisopropylanilide)-1,2-bis (dimethylamido)diborane.

Bis(dimethylamido)diborondichloride (2.350 g, 13.00 mmol) in diethylether (10 ml) was added dropwise to a solution of 2,6-diisopropylaniline, lithium salt (4.765 g, 26.01 mmol) in diethylether (50 ml) at 0° C. This mixture was then allowed to stir overnight at room temperature. After the reaction period the volatiles were removed and the residue was extracted and filtered using hexane. Removal of the hexane resulted in the isolation of a the desired product as a white solid (5.322 g, 88.9 percent yield). $^1$H NMR (toluene-d$_8$): δ 0.9–1.4 (br m, 24 H), 2.3 (s, 6 H), 2.8 (s, 6 H), 3.7 (s, 2 H), 7.0 (br s, 6 H). $^{13}$C NMR (toluene-d$_8$): δ 22.51, 24.03 (br), 28.17, 36.82, 42.67, 123.19, 124.78, 140.71, 145.02 (br). MS(EI): m/z 460.4025 (M-H)$^+$, calcd. (M-H)$^+$ 460.4026.

2G) Preparation of 1,2-Bis(2,6-diisopropylanilide)-1,2-bis (dimethylamido)diborane, dilithium salt.

1,2-Bis(2,6-diisopropylanilide)-1,2-bis(dimethylamido) diborane (1.820 g, 3.950 mmol) was stirred in hexane (75 ml) as n-BuLi (7.91 mmol, 4.94 ml of 1.6 M solution in hexane) was added dropwise. This mixture was then allowed to stir overnight. After the reaction period the mixture was filtered and the salt washed well with hexane and dried under vacuum resulting in the isolation of the desired product as a white powder (1.6878 g, 90.4 percent yield). $^1$H NMR (THF-d$_8$): δ 1.04 (d, $^3$J$_{HH}$=6.9 Hz, 6 H), 1.18 (d, $^3$J$_{HH}$=6.9 Hz, 6 H), 2.45 (s, 12 H), 3.66 (septet, $^3$J$_{HH}$=6.9 Hz, 4 H), 6.29 (t, $^3$J$_{HH}$=7.5 Hz, 2 H), 6.73 (d, $^3$J$_{HH}$=7.5 Hz, 4 H). $^{13}$C NMR (THF-d$_8$): δ 24.88, 25.34, 28.00, 40.91, 114.40, 121.95, 137.21, 158.76.

2H) Preparation of Dichloro-[1,2-Bis(2,6-diisopropylanilide)-1,2-bis(dimethylamido)diborane] titanium.

1,2-Bis(2,6-diisopropylanilide)-1,2-bis(dimethylamido) diborane, dilithium salt (0.600 g, 1.27 mmol) in THF (20 ml) was added dropwise to a slurry of TiCl$_3$(THF)$_3$ (0.471 g, 1.27 mmol) in THF (50 ml) at 0° C. This mixture was then allowed to stir at room temperature for 45 minutes. PbCl$_2$ (0.177 g, 0.640 mmol) was then added as a solid and the mixture allowed to stir for an additional 30 minutes. After the reaction period the volatile components were removed and the residue was extracted and filtered using hexane. Concentration of the hexane fractions and cooling to –10° C. overnight resulted in the formation of orange X-ray quality crystals (0.156 g, 21.3 percent yield). $^1$H NMR (toluene-d$_8$): δ 1.23 (d, $^3$J$_{HH}$=6.6 Hz, 6 H), 1.45 (d, $^3$J$_{HH}$=6.6 Hz, 6 H), 2.17 (s, 6 H), 2.76 (s, 6 H), 3.53 (septet, $^3$J$_{HH}$=6.6 Hz, 4 H), 7.11 (s, 6 H). $^{13}$C NMR (toluene-d$_8$): δ 24.94, 24.67, 29.48, 39.33, 42.93, 124.08 (br), 17.23, 150.64. MS(EI): m/z 578.2789 (M)$^+$, calcd. (M)$^+$ 578.2781. Anal. Calcd. For C$_{28}$H$_{46}$B$_2$N$_2$TiCl$_2$: C, 58.07; H, 8.01; N, 9.67. Found: C, 8.28; H, 8.20; N, 9.42.

Example 3

Dimethyl[1,2-Bis(2,6-diisopropylanilide)-1,2-bis (dimethylamido)diborane]titanium Dichloro-[1,2-Bis(2,6-diisopropylanilide)-1,2-bis (dimethylamido)diborane]titanium (Example 2) (0.272 g, 0.470 mmol) was stirred in diethylether (40 ml) as MeMgBr (0.940 mmol, 0.313 ml of 3.0 M solution in diethylether) was added dropwise. This mixture was allowed to stir for one hour. After the reaction period the volatiles were removed and the residue extracted and filtered using hexane.

Removal of the hexane resulted in the isolation of the desired product as a dark yellow oil (0.209 g, 82.5 percent yield). $^1$H NMR (C$_6$D$_6$): δ 1.05 (s, 6 H), 1.21 (d, $^3J_{HH}$=6.9 Hz, 16 H), 1.32 (d, $^3J_{HH}$=6.3 Hz, 16 H), 2.19 (s, 6 H), 2.69 (s, 6 H), 3.58 (br, 2 H), 7.0–7.2 (m, 6 H). $^{13}$C NMR (C$_6$D$_6$): δ 24.06, 24.83, 29.31, 39.58, 42.93, 57.38, 123.97, 125.18, 139.5 (br), 149.45.

Example 4

Dibenzyl[1,2-Bis(2,6-diisopropylanilide)-1,2-bis(dimethylamido) diborane]zirconium Zirconium tetrachloride (0.100 g, 0.440 mmol) and zirconium tetrabenzyl (0.192 g, 0.440 mmol) were stirred together in diethylether (30 ml) for 1 hour. 1,2-Bis(2,6-diisopropylanilide)-1,2-bis(dimethylamido)diborane, dilithium salt (Example 2G) (0.400 g, 0.842 mmol) in diethylether (30 ml) was then added dropwise and the mixture allowed to stir for 3 hours. After the reaction period the volatiles were removed under vacuum and the residue extracted and filtered using hexane. The filtrate was then concentrated and cooled to –10° C. overnight during which time a white powder precipitated. The mixture was again filtered and the volatile components removed resulting in the isolation of the desired product as a yellow oil (0.123 g, 19.8 percent yield). $^1$H NMR (toluene-d$_8$): δ 1.14 (d, $^3J_{HH}$=6.6 Hz, 6 H), 1.22 (br, 6 H), 1.70 (d, $^3J_{HH}$=9.0 Hz, 2 H), 1.83 (d, $^3J_{HH}$=9.6 Hz, 2 H), 2.10 (s, 6 H) 2.71 (s, 6 H), 3.0–3.2 (br, 2 H), 3.3–3.5 (br, 2 H), 6.59 (d, $^3J_{HH}$=7.2 Hz, 4 H), 6.77 (t, $^3J_{HH}$=7.2 Hz, 2 H), 6.9–7.1 (m, 10 H). $^{13}$C NMR (toluene-d$_8$): δ 23.96 (br), 24.22 (br), 24.36 (br), 25.23 (br), 29.47, 39.72, 43.05, 62.23, 122.70, 123.73 (br), 124.08 (br), 124.33, 127.23, 130.82, 139.26 (br), 140.16 (br), 144.90, 144.92, 149.03.

Example 5

Rac-diisopropylamidoborane-bis-η$^5$-(2-methyl-4-phenylinden-1-yl)zirconium η$^4$-1,4-diphenyl-1,3-butadiene

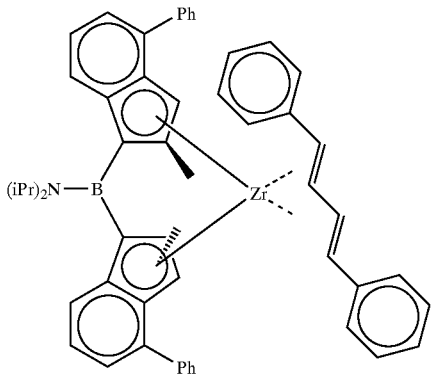

5A) Preparation of Diisopropylaminoboron dichloride.

To a methylene chloride solution of trichloroborane (1.0 M, 100 ml, 0.10 mole) was added dropwise at –78° C. diisopropylamine (13.108 ml, 0.100 mole) over a 30 minute period. The solution was allowed to stir for 1 hour, during which a white precipitate formed. The mixture was allowed to warm to room temperature, and solvent was removed under reduced pressure. The residue was dissolved in 100 ml of dry toluene, triethylamine (13.94 ml, 0.10 mole) was added and the solution was stirred overnight at room temperature. The mixture was filtered, the residue was washed with 20 ml of toluene. Solvent was removed under reduced pressure from the combined filtrates, and the resulting oil was purified by vacuum distillation (25–28° C., 13 Pa, 0.1 mm) to give 9.2 g (51 percent) of product as a colorless liquid.

$^1$H NMR (C$_6$D$_6$): δ 0.95 (d, 12 H), 3.63 (broad multiplet, 2 H).

5B) Preparation of N,N-diisopropylamino bis(2-methyl-4-phenylindenyl) borane

To 25 ml THF solution of N,N-diisopropylaminoboron dichloride (0.858 g, 4.72 mmole) at room temperature was added drop wise lithium (2-methyl-4-phenyl)indenide (2.00 g, 9.44 mmole in 20 ml THF). The mixture was stirred for 24 hours. Solvent was removed under reduced pressure. The residue was extracted with toluene (2×50 ml), filtered through a medium frit, and solvent was removed under reduced pressure to give a light yellow solid (2.4 g, 97 percent).

5C) Preparation of rac-diisopropylaminoborane-bis-η$^5$-(2-methyl-4-phenylindenyl)zirconium η$^4$-1,4-diphenyl-1,3-butadiene N,N-diisopropylamino bis(2-methyl-4-phenylindenyl) borane (1.20 g, 2.3 mmole) was dissolved in 40 ml of toluene, 2.1 equivalents of potassium bis(trimethylsilyl) amide (0.964 g, 4.8 mmole) was added and the resulting mixture was stirred at room temperature for 24 hours. Volatile components were removed under reduced pressure, and the resulting orange solid washed with 10 ml of hexane, filtered and pumped dry. The dipotassium salt residue (1.3 g, 95 percent, 2.18 mmole) was redissolved in 25 ml of toluene. (1,4-diphenyl-1,3-butadiene)-bis(triethylphosphine)zirconium dichloride (1.318 g, 2.18 mmole) was added and the solution stirred for 12 h at room temperature. The product mixture was filtered through diatomaceous earth filter aid and the solvent of the filtrate was removed under reduced pressure. Further purification was carried out by recrystallization from hexane to yield 0.85 g (48 percent) of the desired product as a dark red solid.

$^1$H NMR (C$_6$D$_6$): δ 7.6 (d, 2H); 7.42–7.00, (m, 18 H); 6.9 (d, 2H); 6.82 (d, 4H); 5.57 (s, 2H); 4.03, m, 2H); 3.45–3.57 (dd, 2H); 1.8 (s, 6H); 1.28–1.33 (m, 12H).

Example 6

Preparation of diisopropylamidoboranebis(cyclopentadienyl)zirconium dichloride

6A) Diisopropylamidoboron dichloride

To a solution of BCl$_3$ (17 g, 145 mmol) in CH$_2$Cl$_2$ (25 ml) at –78° C. was slowly added diisopropylamine (18.49 ml, 132 mmol). A white precipitate formed during addition. The mixture was warmed to room temperature to give a colorless solution. Solvent was removed under high vacuum at room temperature, the residue was then dissolved in benzene (45 ml). Triethylamine (18.8 ml, 134.6 mmol) was added to the solution at room temperature, the mixture was then stirred overnight at room temperature, then filtered to give a red solution. Vacuum distillation (27–28° C., 4 Pa) gave the product (15 g, 57 percent) as a colorless liquid:

$^1$H NMR (500 MHz, CDCl$_3$) d 1.26 (d, 12H, J=5.8 Hz), 3.95 (br, 2H), NCH) $^{13}$C NMR (100 MHz, CDCl$_3$) d 22.1, 49.2 (br). $^{11}$B NMR (115 MHz, CDCl$_3$) 29.4. MS (EI, m/e (intensity)): 181 (M+, 5), 166 (43), 124 (61), 43 (I 00).

6B) Diisopropylamidobis(cyclopentadienyl) borane

To a solution of the above product (0.39 g, 2.1 mmol) in THF (5 ml) at –78° C. was added dropwise a solution of lithium cyclopentadienide (0.31 g, 2.1 mmol) in THF (10 ml) at –78° C. The mixture was slowly warmed to room temperature and stirred overnight at room temperature to give a red solution. After solvent removal, the residue was extracted with pentane (3×), filtered, pentane was then removed to give the product (0.55 g, 100 percent) as an yellow syrup.

$^{13}$B NMR (115 MHz, C6D,) d 39.8 (major), 30.4 (minor). MS (EI, m/e (intensity)): 241 (M+, 47), 226 (40), 176 (16), 93 (100).

GC-MS was also recorded on the reaction mixture shortly after mixing the two reagents at −78° C., from which only cyclopentadienyldiisopropylboron chloride was detected: MS (EI, m/e (intensity)): 211 (M+, 24), 196 (100), 154 (22).

6C) Dilithium diisopropylamidoboryldicyclopentadienide

To a solution of the above product (0.61 g, 2.53 mmol) in THF (7 ml) at −78° C. was added lithium diisopropylamide (5.57 mmol, prepared in situ from diisopropylamine (0.780 ml, 5.57 mmol) and BuLi (2.50 M, 2.23 ml, 5.57 mmol). The mixture was warmed to room temperature and stirred for 2 hr. Solvent was then removed, residue was washed with pentane to give the product (0.58 g, 91 percent) as a white solid:

$^1$H NMR (360 MHz, THF-d$_8$) d 1.24 (d, 12H, J=6.8 Hz, NCHCH$_3$), 4.54 (m, 2H, NCH), 5.74 (t, 4H, J=2.4 Hz), 5.83 (t, 4H, J=2.4 Hz).

$^{13}$C NMR (100 MHz, THF-d$_8$) d 23.9 (NCHCH$_3$), 25.9 (NCHCH$_3$), 49.3 (NCH), 104.4, 111.9.

$^{11}$B NMR (115 MHz, THF-d$^8$) d 44.6.

6D) Diisopropylamidoboranebis(cyclopentadienyl) zirconium dichloride

To a solution of diisopropylamidobis(cyclopentadienyl) borane (0.71 g, 2.95 mmol) in Et$_2$O (15 ml) at −78° C. was added lithium diisopropylamide (6.93 mmol). The mixture was stirred for 2 hr at room temperature to give a slightly turbid solution. The solution was then added to a suspension of ZrCl$_4$ (0.69 g, 2.95 mmol) in Et$_2$O (15 ml) at −78° C. The resulting mixture was stirred overnight at room temperature to give an yellowish suspension. Solvent was partially removed and the residue concentrated and cooled to −78° C. to give the product (0.50 g, 38 percent) as colorless crystals.

$^1$H NMR (400 MHz, CDCl$_3$) d 1.32 (d, 12H, J=7.0 Hz), 2.92 (m, 2H), 5.65 (t, 4H, J=2.4 Hz), 6.80 (t, 4H, J=2.4 Hz). $^{13}$C NMR (100 MHz, CDCl$_3$) d 24.6, 49.6, 111.4, 125.7. $^{13}$B NMR (115 MHz, CDCl$_3$) 5 37.6. HRMS (EI), calculated for C$_{16}$H$_{22}$BNC$_{12}$Zr: 399.0269, found: 399.0272.

Example 7

Preparation of Meso-diisopropylamidoboranebis (inden-1-yl)zirconium dichloride

7A) Diisopropylamidobis(inden-1-yl)borane

To a solution of diisopropylamidoboron dichloride (Example 3, step A)) (1.10 g, 6.0 mmol) in THF (10 ml) at −78° C. was added dropwise a solution of lithium indenide (1.50 g, 12.3 mmol) in THF (40 ml) at −78° C. The mixture was slowly warmed to room temperature and stirred overnight at room temperature to give a red solution. After solvent removal, the residue was extracted with CH$_2$Cl$_2$ (3×), filtered and the solvent removed to give the desired product (2.12 g, 100 percent) as a white solid:

$^{11}$B NMR (115 MHz, C$_6$D,) d 41.4. MS (EI, m/e (intensity)): 341 (M+, 8), 226 (100) HRMS (EI), calculated for C$_{24}$H$_{28}$BN C$_{24}$H$_{28}$BN: 341.2315, found: 341.2310.

7B) Meso-Diisopropylamidoboranebis(inden-1-yl) zirconium dichloride

To a suspension of the above product (0.39 g, 1.41 mmol) in Et$_2$O (10 ml) at −78° C. was added lithium diisopropylamide (in situ prepared from iPr$_2$NH (2.62 mmol) and BuLi (2.50 M, 2.62 mmol). The mixture was stirred over night at room temperature to give an orange suspension. Solvent was removed and the residue extracted with toluene, and filtered. Toluene was then removed to give an orange solid composed of a mixture of the two stereoisomers (rac/meso, ca. 6:4). Repeated recrystallization (3×) from toluene at −78° C. gave the pure meso isomer (0.08 g, 14 percent) as an orange solid. M.p.=250–254° C. (dec.).

$^1$HNMR (500 MHz, CDCl$_3$) 1.54 (d, 6H, J=6.6 Hz), 1.57 (d, 6H, J=6.8 Hz), 4.27 (m, 2H, NCH), 5.91 (d, 2H, J3.0 Hz), 6.9 (m, 4H), 7.17 (t, 2H, J=7.6 Hz), 7.31 (dd, 2H, J=8.3, 3.6 Hz), 7.53 (d, 2H, J=8.6 Hz). $^{13}$C NMR (75 MHz, CDCl$_3$) d 24.7, 25.0 (NCHCH$_3$), 49.7, 100.2 (BC), 115.7, 117.2, 125.2, 125.3, 125.6, 125.9, 126.5, 131.4. $^{11}$B NMR (115 MHz, CDCl$_3$) 8 39.5. HRMS (EI), calculated for C$_{24}$H$_{26}$BNC$_{12}$Zr: 499.0582, found, 499.0606. MS (EI, m/e (intensity)): 501 (M+, 20), 458 (7), 341 (18), 226 (93), 143 (80), 115 (99).

Example 8

Preparation of Rac-diisopropylamidoboranebis (inden-1-yl)zirconium bis(dimethylamide To a mixture of diisopropylamidobis(inden-1-yl)borane (Example 4, step A)) (1.01 g, 2.96 mmol) and Zr(NMe$_2$)$^4$ (0.79 g, 0.96 mmol) was added toluene (15 ml). The resulting solution was heated to 65° C. and stirred for 2 hr to give a bright red solution. The product consisted of two isomers with a ratio of 6.7:1. The solution was filtered, concentrated, and cooled to −78° C. to give the pure rac isomer (0.50 g, 33 percent) as red crystals. The structure was confirmed by X-ray diffraction analysis on single crystals grown from toluene/hexane at −20° C. M.p.=220° C. (dec.).

$^1$H NMR (500 MHz, C$_6$D$_6$) d 1.20 (d, 6H, J=6.8 Hz), 1.27 (d, 6H, J=6.6 Hz), 2.61 (s, 12H), 3.86 (in, 2H), 6.04 (d, 2H, J=2.9 Hz), 6.74 (m, 4H), 7.00 (t, 2H, J=7.6 Hz), 7.37 (dd, 2H, J=8.5, 0.9 Hz), 7.52 (d, 2H, J=8.5 Hz). $^{13}$C NMR (90 MHz, C$_6$D$_6$) 5 24.6, 24.9, 47.9 (NCH$_3$), 49.6, 105.6, 112.4, 123.1, 123.2, 124.0, 124.2, 126.3, 129.1. $^{11}$B NMR (115 MHz, C$_6$D$_6$) d 40.8. HRMS (EI), calculated for C$_{28}$H$_{38}$BN$_3$Zr: 517.2206, found, 517.2217. MS (EI, m/e (intensity)): 517 (M+, 20), 471 (45), 429 (100), 330 (24), 226 (70).

Example 9

Rac-Diisopropylamidoboranebis(inden-1-yl) zirconium dichloride

To a solution of rac-diisopropylamidoboranebis(inden-1-yl)zirconium bis(dimethylamide) (0.50 g, 0.96 mmol) in toluene (35 ml) at room temperature was added trimethyhlsilyl chloride (2.0 ml, 15.76 mmol). The solution was stirred for 8 h at room temperature to give an orange suspension. Solvent was removed, residue was washed with pentane (2×) to give the desired product (0.40 g, 83 percent) as an orange powder. Single crystals suitable for X-ray structural analysis were grown from mixed solvents of CH$_2$Cl$_2$ and hexane at −20° C. M.p.=242° C. (dec.).

$^1$H NMR (500 MHz, CDCl$_3$) d 1.50 (d, 6H, J=6.8 Hz), 1.55 (d, 6H, J=6.6 Hz), 4.24 (heptet, 2H, J=7.7 Hz), 5.79 (d, 2H, J=3.0 Hz), 6.80 (dd, 2H, J=3.2, 0.7 Hz), 7.07 (t, 2H, J=7.6 Hz), 7.28 (dd, 2H, J=7.0, 0.7 Hz), 7.38 (t, 2H, J=8.0 Hz), 7.58 9d, 2H, J=8.8 Hz). $^{13}$C NMR (75 MHz, CDCl$_3$) d 24.7, 25.0, 49.6, 98.4 (BC), 113.1, 114.1, 122.0, 123.0, 125.8, 126.4, 127.2, 131.9. $^{11}$B NMR (115 MHz, CDCl$_3$) d 39.2. HRMS (EI), calculated for C$_{24}$H$_{26}$BNCl$_2$Zr: 499.0582, found, 499.0606. MS (EI, m/e (intensity)): 501 (M+, 20), 458 (7), 341 (18), 226 (93), 143 (80), 115 (99). Anal. Calculated for C$_{24}$H$_{26}$BNCl$_2$Zr: C, 57.48; H, 5.19; N, 2.79. Found: C, 57.46; H, 5.32; N, 2.68.

Example 10

Preparation of Rac-(diisopropylamidoborane)bis (tetrahydroinden-1-yl)zirconium dichloride A solution of diisopropylamidoboranebis(inden-1-yl) zirconium dichloride (Example 6) (0.16 g, 0.32 mmol) in CH$_2$Cl$_2$ (7 ml) was added to an autoclave reactor containing PtO$_2$ (0.0105 g). The mixture was flushed four times with H$_2$ (200 psi, 1.4 MPa), then charged with H$_2$ (1500 psi, 10.4 MPa) and stirred for 15 h at room temperature to give a greenish suspension. CH$_2$Cl$_2$ (25 ml) was added the mixture which was then filtered. Solvent was removed under reduced pressure and the residue was washed with pentane (2x) to give diisopropylamidoboranebis(tetrahydroinden-1-yl) zirconium dichloride (0.15 g, 92 percent) as a slightly greenish solid.

$^1$H NMR (400 MHz, C$_6$D$_6$) d 1.06 (d, 12H, J=6.6 Hz), 1.33 (m, 2H), 1.47 (m, 2H), 1.92 (m, 4H), 2.05 (t, 1H, J=4.8 Hz), 2.09 (d, 1H, J=5.0 Hz), 2.34 (m, 2H), 2.53 (t, 1H, J=5.3 Hz), 2.56 (t, 1H, J=5.0 Hz), 3.20 (m, 2H), 3.60 (hept, 2H, J=6.6 Hz), 5.01 (d, 2H, J=2.9 Hz), 6.53 (d, 2H, J=2.6 Hz). $^{13}$C NMR (100 MHz, C$_6$D$_6$) d 23.0, 23.6, 24.4, 24.7, 24.8, 27.0, 49.6, 109.7, 121.6, 124.2, 136.1. $^{11}$B NMR (115 MHz, C$_6$D$_6$) d 39.2 ppm. HRMS (EI) Calculated for C$_{24}$H$_{34}$$^{11}$BNCl$_2$Zr 507.1208, found 507.1198.

Example 11

Preparation of Rac-N,N-diisopropylamidoborane-bis-η$^5$-(2-methyl-4-naphthyl indenyl) zirconium η$^4$-1,4-diphenyl-1,3-butadiene

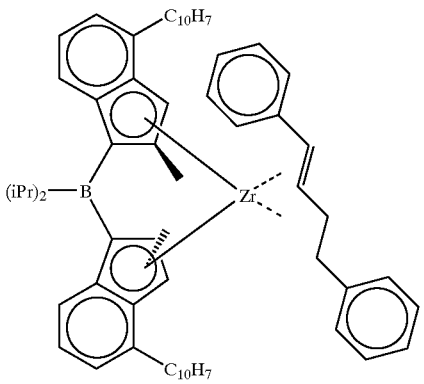

11A) Preparation of potassium (2-methyl-4-naphthyl) indenide

2-Methyl-4-naphthylindene (1.00 g, 3.27 mmole) was dissolved in 20 ml of toluene, potassium bis(trimethylsilyl) amide (1.05 equivalent, 3.43 mmole, 0.684 g) was added and the reaction mixture was stirred at room temperature for 24 hours, during which a yellow solid precipitated. Hexane was added (20 ml) and the mixture was stirred for 2 h. The solid product was isolated by vacuum filtration through a medium porosity frit. The solid was pumped dry giving 1.10 g, 98 percent of the desired product.

11B) Preparation of N,N-diisopropylamino bis(2-methyl-4-naphthylindenyl) borane

To a solution of N,N-diisopropylaminoboron dichloride (0.309 g, 1.70 mmole) in 25 ml of THF at room temperature was slowly added dropwise a 10 ml THF solution of potassium (2-methyl-4-naphthyl) indenide (1.00 g, 3.40 mmole). The mixture was stirred for 24 hours at room temperature, solvent was removed, and the residue was extracted with toluene (2x25 ml). The combined extracts were filtered through a medium frit, and solvent was removed under reduced pressure to give a light yellow solid (1.0 g, 95 percent).

11C) Preparation of rac-N,N-diisopropylaminoborane-bis-η$^5$-(2-methyl-4-naphthyl indenyl) zirconium η$^4$-1,4-diphenyl-1,3-butadiene.

N,N-diisopropylamino bis(2-methyl-4-naphthylindenyl) borane (0.860 g, 1.38 mmole) was dissolved in 20 ml of toluene, 2.05 equivalents of potassium bis(trimethylsilyl) amide (0.566 g, 2.84 mmole) was added and the reaction mixture was stirred at room temperature for 24 hours. Volatile components were removed under reduced pressure, and the residue was redissolved in 25 ml of toluene. While stirring at room temperature, (1,4-diphenyl-1,3-butadiene) bis(triethylphosphine)-zirconium dichloride (0.835 g, 1.38 mmol) was added and the solution was stirred for 12 h at room temperature. The product mixture was filtered through diatomaceous earth filter aid and the solvent of the filtrate was removed under reduced pressure. Further purification was carried out by recrystallization from hexane to yield 0.27 g (21 percent) of the desired product as a dark red solid.

$^1$H NMR (C$_6$D$_6$): δ7.75–7.00 (mm, 30 H); 4.82 (s, 2H); 3.85–3.95(m, 2H); 3.62–3.70 (dd, 2H); 1.82–1.9 (dd, 2H) 1.6 (s, 6H); 1,10–1.33 (m, 12H).

Example 12

Rac-1,2-bis(dimethylamidodiborane)bis(2-methyl-4-phenylind en-1-yl)zirconium η$^4$-1,4-diphenyl-1,3-butadiene

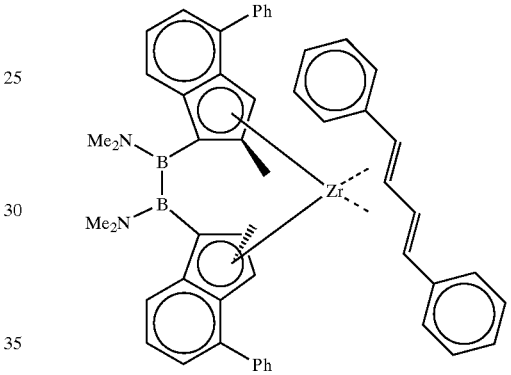

12A) Preparation of 1,2-Bis(2-methyl-4-phenylinden-1-yl)-1,2-bis(dimethylamido)-diborane Bis(dimethylamido)diborondichloride (0.500 g, 2.77 mmol) in diethylether (10 ml) was added dropwise to a solution of 2-methyl-4-phenylindene, lithium salt (1.407 g, 11.07 mmol) in diethylether (50 ml) at 0° C. This mixture was stirred overnight at room temperature and the volatiles were removed. The residue was extracted using CH$_2$Cl$_2$. Filtration and removal of the CH$_2$Cl$_2$ resulted in the isolation of a the desired product as a pale yellow solid (0.902 g, 62.6 percent yield).

12B) Preparation of 1,2-Bis(dimethylamido)-1,2-bis(2-methyl-4-phenylindene) diborane, dipotassium salt.

1,2-Bis(dimethylamido)-1,2-tris(2-methyl-4-phenylindene) diborane (0.791 g, 1.52 mmol) and KN(TMS)$_2$ (0.607 g, 3.04 mmol) were stirred together in toluene (50 ml) overnight. The reaction mixture was then refluxed for one hour, cooled to room temperature, and dried under vacuum. The residue was then slurried in hexane and filtered and the gold microcrystalline solid dried under vacuum (0.881 g, 97.1 percent yield).

12B) Preparation of rac-[1,2-Bis(dimethylamido)-1,2-bis(2-methyl-4-phenylindene)diborane] zirconium(trans,trans-1, 4-diphenyl-1,3-butadiene)

1,2-Bis(dimethylamido)-1,2-bis(2-methyl-4-phenylindene) diborane, dipotassiium salt (0.808 g, 1.35 mmol) was added slowly as a solid to a solution of (1,4-diphenylbutadiene)ZrCl$_2$(PEt$_3$)$^2$ (0.819 g, 1.35 mmol) in toluene (75 ml). This mixture was allowed to stir overnight. After the reaction period the mixture was filtered and the volatiles removed resulting in the isolation of a deep red residue. The residue was then slurried in cold hexane, filtered, and dried under vacuum resulting in the isolation of the desired product as a dark red microcrystalline solid (0.501 g, 45.3 percent yield).

$^1$H NMR (C$_6$D$_6$): δ 1.1–1.2 (m, 2 H), 2.02 (s, 6 H), 2.66 (s, 6 H), 2.90 (s, 6 H), 3.3–3.4 (m, 2 H), 5.28 (s, 2 H), 6.82 (d, 3J$^{HH}$=6.6 Hz, 2 H), 6.9–7.3 (m, 14 H), 7.53 (d, 3J$^{HH}$=8.4 Hz, 2 H). $^{13}$C NMR (C$_6$D$_6$): δ 15.10, 42.7, 44.36 86.78, 93.34, 106.54, 119.17, 123.12, 123.39, 123.71, 124.26, 127.88, 128.51, 128.90, 129.34, 135.76, 140.85, 145.80.

Example 13

Rac-diisopropylamidoborane-bis-η$^5$-(2-methyl-4-phenylinden-1-yl)hafnium η$^4$-1,4-diphenyl-1,3-butadiene

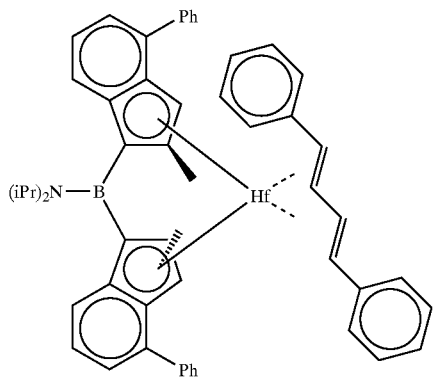

Hafnium tetrachloride (0.375 g, 1.17 mmol) was slurried into 40 ml of toluene. To this slurry were added triethylphosphine (0.346 ml, 2.34 mmol, via syringe), Li powder (Aldrich, low sodium, 0.081 g, 11.7 mmol), and 1,4-diphenyl-1,3-butadiene (0.242 g, 117 mmol). The reaction mixture was stirred overnight at room temperature then filtered using a medium porosity frit and diatomaceous earth pad to remove the unreacted Li metal. To the filtrate was added dipotassium diisopropylamidobis(1-(2-methyl-4-phenylindenide))borane, K$_2$[Pr$_2$NB(2-Me-4-Ph-indenide)$_2$], (0.700 g, 1.17 mmol) using 10 ml of toluene to aid in the transfer. The reaction mixture was stirred for 1 hour at room temperature. The toluene was removed under reduced pressure and the reaction product was extracted with hexane (twice) and filtered (medium porosity frit with diatomaceous earth pad). Additional product was obtained by extracting the salt byproduct using toluene and refiltering using a medium porosity frit and diatomaceous earth pad.

$^1$H NMR spectroscopic analysis indicated that the desired rac-$^i$Pr$_2$NB(2-Me-4-Ph-inden-1-yl)$_2$Hf(1,4-diphenyl-1,3-butadiene) isomer was largely insoluble in hexane and that the undesired meso-isomer could be separated by repeated extraction with hexane. Final isolation and purification of rac-$^i$Pr$_2$NB(2-Me-4-Ph-inden-1-yl)$_2$Hf(1,4-diphenyl-1,3-butadiene) was accomplished by soxhlet extraction using hexane. After the hexane extract becomes colorless the thimble was removed and dried, yielding 0.042 g of pure rac-$^i$Pr$_2$NB(2-Me-4-Ph-inden-1-yl)$_2$Hf(1,4-diphenyl-1,3-butadiene) as determined by $^1$H and $^{13}$C NMR spectroscopic analysis.

$^1$H NMR (C$_6$D$_6$): δ7.6(d, 2H); 7.42–7.00, (m, 18 H); 6.9 (d, 2H); 6.82 (d, 4H); 5.57 (s, 2H); 4.03, m, 2H); 3.45–3.57 (dd, 2H); 1.8(s,6H); 1.28–1.33 (m, 12H).

Example 14

Rac-diisopropylamidoborane-bis-η$^5$-(2-methyl-4-phenylinden-1-yl)zirconium η$^4$-1,4-diphenyl-1,3-butadiene

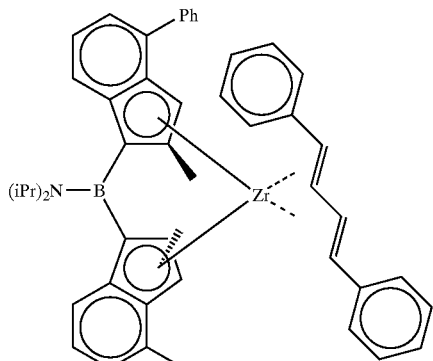

In a glove box, diisopropylamidobis(2-methyl-4-phenylinden-1-yl)borane (0.125 g, 0.240 mmole) was dissolved in 20 ml of dry THF, and 2 equivalents of potassium bis(trimethyisilyl)amide (0.500 molar solution, 0.960 ml, 0.480 mmole) was added dropwise over 10 minute period at room temperature, after which the solution was stirred for 4 hours. Volatile components were removed under reduced pressure and the remaining solid were redissolved in 25 ml of toluene. While stirring at room temperature, (1,4-diphenyl-1,3-butadiene)bis(triethylphosphine)zirconium dichloride (0.145 g, 0.240 mmole) was added and the resulting solution was stirred for 4 hours. The product was recovered by filtering the mixture through diatomaceous earth and removing the solvent of the filtrate under reduced pressure. Further purification was carried out by recrystallization from hexane to yield the product as a dark red solid.

Example 15

Preparation of Rac-{$^i$Pr$_2$NC(N$^i$Pr)$_2$}borane-bis-η$^5$-(2-methyl-4-phenylindenyl) zirconium η$^4$-1,4-diphenyl-1,3-butadiene.

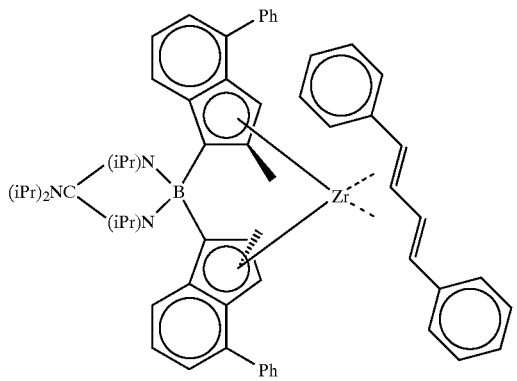

15A) Preparation of $^i$Pr$_2$NC(N$^i$Pr)2)boron dichloride.

Diisopropylcarbodiimide (1.178 g, 9.33 mmole) was dissolved in 20 m of toluene, cooled to 0° C., and solid lithium diisopropylamide (1.00 g, 9.33 mmole) was added slowly to the solution over a 5 minute period. The solution was allowed to warm to room temperature while stirring for 3 hours. This solution was subsequently added dropwise over a 30 minute period to a 1 molar heptane solution (0° C.) of born trichloride (9.33 ml, 9.33 mmole) and allowed to warm to room temperature overnight. The solution was filtered, and solvents were removed under reduced pressure to yield 2.3 g (97 percent) of light yellow oil.

$^1$H NMR (C$_6$D$_8$): δ 3.6–3.4 (m, 2H); 3.4–3.25 (septet, 2H); 1.43 (d, 12H); 0.8 (d, 12 H).

15B) Preparation of bis(2-methyl-4-phenylindenyl) {$^i$Pr$_2$NC(N$^i$Pr)$_2$}borane $^i$Pr$_2$NC(N$^i$Pr)$_2$}boron dichloride (0.30g, 0.97 mmole) was dissolved in 30 ml of THF, and potassium (2-methyl-4-phenyl)indenide (0.47g, 1.95 mmole) was added. The mixture was stirred for 24 hours at room temperature, followed by heating at reflux for 4 hours. The product mixture was allowed to cool to room temperature, and solvent was removed under reduced pressure. The residue was extracted with toluene (2×50 ml), filtered through a medium frit, and solvent was removed under reduced pressure to give a light yellow solid (0.533 g, 85 percent).

15C) Preparation of rac-{iPr$^2$NC(NiPr)$^2$}borane-bis-η$^5$-(2-methyl-4-naphthyl indenyl) zirconium η$^4$-1,4-diphenyl-1,3-butadiene.

Bis(2-methyl-4-phenylindenyl) {$^i$Pr$_2$NC(N$^i$Pr)$_2$}borane (0.533 g, 0.82 mmole) was dissolved in 20 ml of toluene, 2.00 equivalents of potassium bis(trimethylsilyl)amide (0.0.328 g, 1.65 mmole) was added and the reaction mixture was stirred at room temperature for 24 hours. Volatile components were removed under reduced pressure, and the residue was washed with 2×25 mL of hexane. Volatile components were removed under reduced pressure to yield 0.382 g (64 percent) of the orange solid dipotassium salt. A portion of this solid (0.100 g, 0.14 mmole) was dissolved in 15 mL of toluene. While stirring at room temperature, (1,4-diphenyl-1,3-butadiene)bis(triethylphosphine) zirconium dichloride (0.084 g, 0.14 mmole) was added and the solution was stirred for 12 h at room temperature. The product mixture was filtered through diatomaceous earth filter aid and the solvent of the filtrate was removed under reduced pressure to give 0.115 g (88 percent) of crude product which existed as a rac/meso mixture. Further purification was carried out by recrystallization from hexanes to yield 0.015 g (12 percent) of rac-product as a dark red solid. $^1$H NMR (C$_6$D$_6$): δ7.6–6.7, (mm, 26 H); 5.55 (s, 2H); 4.05–3.90(m, 2H); 3.5 (dd, 2H); 2.7–2.4 (m, 2H); 1.78 (s, 6H); 1.55 (dd, 2H); 1.25 (m, 12 H); 0.95 (m, 12H).

Example 16

Rac-dimethylamidoborane-bis-η$^5$-(2-methyl-4-phenylinden-1-yl)zirconium η$^4$-1,4-diphenyl-1,3-butadiene

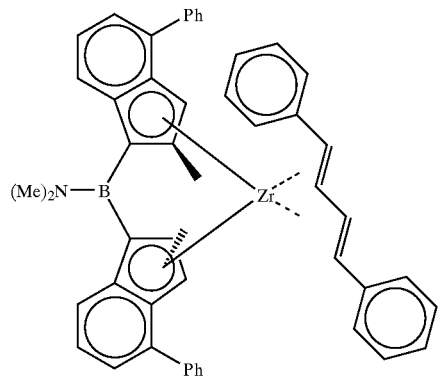

16A) Preparation of Dimethylamidodibromoborane

B(NMe$_2$)$_3$ was added to BBr$_3$ dropwise. The reaction was immediate and exothermic. This mixture was allowed to stir for 2 hours at which time NMR analysis showed the reaction to be essentially quantitative and complete (22.510 g, 99.9 percent yield).

$^1$H NMR (C$_6$D$_6$): δ2.31(6 H). $^{13}$C NMR (C$_6$D$_6$): δ 41.45.

16B) Preparation of Dimethylamido-bis(2-methyl-4-phenylindinyl)borane.

A solution of dimethyamidodibromoborane (0.511 g, 2.38 mmol) in toluene (10 ml) was cooled to 0° C. and diethylether (2 equivalents) added. This mixture was then added dropwise to a solution of 2-methyl-4-phenylindene, lithium salt (1.011 g, 4.76 mmol) in THF (50 ml) at 0° C. This mixture was then allowed to stir for overnight at room temperature. After the reaction period the volatile components were removed and the residue extracted and filtered using hexane. Removal of the hexane resulted in the isolation of a yellow oil (1.103 g, 99.9 percent yield).

16C) Preparation of Dimethylamido-bis(2-methyl-4-phenylindenyl)borane, dipotassium salt.

Dimethylamido-bis(2-methyl-4-phenylindenyl)borane (1.010 g, 2.17 mmol) and KN(TMS)$_2$ (0.866 g, 4.34 mmol) were stirred together in toluene (50 ml) overnight. The reaction mixture was then refluxed for one hour, cooled to room temperature, and dried under vacuum. The residue was then slurried in hexane and filtered and the orange microcrystalline solid dried under vacuum (1.246 g, <100% yield due to residual solvent still present as observed by NMR).

16D) Preparation of rac-[Dimethylamido-bis(2-methyl-4-phenylindene)borane]-zirconium (trans,trans-1,4-diphenyl-1,3-butadiene).

Dimethylamido-bis(2-methyl-4-pheny-lindenyl)borane, dipotassium salt (1.246 g, 2.30 mmol) was added slowly as a solid to a solution of (1,4-diphenylbutadiene)ZrCl$_2$(PEt$_3$)$_2$ (1.391, 2.30 mmol) in toluene (75 ml) and allowed to stir overnight. After the reaction period the mixture was filtered and the volatiles removed resulting in the isolation of a dark residue. This residue was slurried in hexane and filtered. Red crystals grew over a 2-hour period of time from the sitting hexane filtrate (0.222 g). The solid on the frit was washed through the frit using toluene and a second crop of crystals was grown from this mixture by allowing the solution to slowly concentrate over a period of one week by slow evaporation of the toluene (0.100 g). Combining the crystals obtained resulted in the isolation of a total of 0.322 g (18.4 percent yield) of highly pure product. $^1$H NMR (C$_6$D$_6$): δ 1.71 (s, 3 H), 1.7–1.8 (m, 2 H), 2.89 (s, 3 H), 3.4–3.5 (m, 2 H), 5.52 (s, 2 H), 6.76 (d, $^3$J$_{HH}$=7.2 Hz, 4 H), 6.8–7.4 (m, 12 H), 7.43 (d, $^3$J$_{HH}$=8.4 Hz, 2 H). $^{13}$C NMR (C$_6$D$_6$): δ 15.95, 39.52, 85.43, 90.93, 104.13, 117.32, 12.49, 121.65, 122.3 (br), 123.32, 124.19, 124.32, 127.81, 127.83, 128.68, 136.06, MS(El): m/z 759.2635 (M—H)$^+$, calcd. (M—H)$^+$ 759.2610.

Example 17

Bis(trimethylsilyl)amido(η-fluoren-9-yl)(η-cyclopentadienyl)boranezirconium Dichloride 17A) Preparation of bistrimethylsilylamido(9-fluorenyl) boron chloride n-Butyllithium (2.5 M hexane, 4.20 ml, 10.50 mmol) was added to a solution of fluorene (1.66 g, 10.00 mmol) in THF (15 ml) at −78° C. The resulting mixture was slowly warmed up and stirred at room temperature for 5 h to give a red solution. The solution was cooled to −78° C. and added dropwise to a solution of bis(trimethylsilyl)amidoboron dichloride (TMS)$_2$NBCl$_2$ (2.42 g, 10.00 mmol) in THF (25 ml) at −78° C. to give a light yellow solution. The solution was stirred overnight at room temperature. Volatile components were removed, and the residue was extracted with pentane and filtered. The pentane was removed to give the desired product (3.70 g, 100 percent yield) as a white solid.

$^1$H NMR (400 MHz, CDCl$_3$): δ0.45 (s, 18H), 4.41 (s, 1H), 7.34 (dt, 2H, J=7.4, 1.1 Hz), 7.42 (t, 2H, J=7.3 Hz), 7.49 (d, 2H, J=7.6 Hz), 7.87 (d, 2H, J=7.4 Hz). $^{13}$C NMR (100 MHz, CDCl$_3$) δ 4.6, 121.0, 125.4, 127.2, 127.3, 143.0, 145.9. $^{11}$B NMR (115.5 MHz, CDCl$_3$), δ 46.6.

17B) Preparation of bis(trimethylsilyl)amido(9-fluorenyl)(cyclopentadienyl) borane A solution of CpNa/THF (0.24 g, 2.40 mmol) in THF (15 ml) at −78° C. was added dropwise to a solution of bistrimethylsilylamido(9-fluorenyl)boron chloride (0.89 g, 2.40 mmol) THF (15 ml) at −78° C. The resulting yellow solution was slowly warmed to room temperature with stirring and stirred over night. Volatile components were removed under reduced pressure, and the residue was extracted with pentane and filtered. The pentane solution was concentrated and cooled to −78° C. to give the desired product (0.57 g, 59 percent) as a white solid.

$^1$H NMR (400MHz, C$_6$D$_6$): δ 0.20 (s, 18 H), 1.71 (t, 2H, J=1.4 Hz), 4.33 (s, 1 H), 5.93 (m, 1 H), 6.13 (m, 1 H), 6.69 (dd, 1 H, =14, 1.5 Hz), 7.09 (dt, 2H, J=7.2, 1.5 Hz), 7.19 (dt, 2 H, J=7.4, 1.7 Hz), 7.46 (dd, 2H, J=7.4. 1.1 Hz), 7.70 (dd, 2H, J=7.6, 0.8 Hz). $^{13}$C NMR (100 MHz, C$_6$D$_6$,) δ5.1, 43.4, 120.6, 125.8, 126.7, 127.2, 132.2, 139.5, 142.9, 143.1, 147.4. $^{11}$B NMR (115.5 MHz, C$_6$D$_6$) δ 51.6. HRMS (El) calculated for C$_{23}$H$_{29}$BNSi, (M—CH$_3$), 386.1932; found, 366.1945.

17C)) bis(trimethylsilyl)amidoborane(η-cyclopentadienyl)(η-fluoren-9-yl)zirconium dichloride A solution of lithium diisopropylamide (prepared in situ from iPr$_2$NH (0.54 ml, 3.84 mmol) and BuLi (2.5 M hexane, 1.61 mil, 4.03 mmol)) in THF (10 ml) was added to a solution of bis(trimethylsilyl)amido(9-fluorenyl)(cyclopentadienyl) borane (0.77 g, 1.92 mmol) in THF (10 ml) at −78° C. The resulting mixture was slowly warmed to room temperature and stirred overnight to give a dark red solution. Volatile components were removed to give an orange solid which was then dissolved in toluene (15 ml). The toluene solution was added to a suspension of ZrCl$_4$ (0.40 g, 1.9 mmol) in toluene (8 ml) at −78° C. The mixture was warmed to room temperature and stirred overnight to give a dark red suspension. Volatile components were removed under reduced pressure, and the residue was extracted with toluene and then filtered. The volatile components were removed under reduced pressure, and the residue was washed with pentane (3x) to give the product as red solid.

mp=252–254 (dec.). $^1$H NMR (400 MHz, CDCl$_3$): δ0.26 (s, 9H), 0.50 (s, 9H), 5.44 (t, 2H, J=2.4 Hz), 6.45 (t, 2H, J=2.4 Hz), 7.19 (d, 2H; J=8.4 Hz), 7.31 (t, 2H, J=7.5 Hz), 7.62 (t, 2H, J=7.8 Hz), 8.12 (d, 2H, J=8.4 Hz). 1$_3$C NMR (75 MHz, CDCl$_3$) δ 4.8, 5.9, 105.3, 121.4, 122.9, 124.4, 125.4, 125.7, 129.1, 143,0. $^{11}$B NMR (115.5 MHz, CDCl$_3$) δ 48.2. FIRMS (El) calculated for C$_{24}$H$_{30}$BNSi$_2$Cl$_2$Zr: 559.0434; found, 559.0443.

Example 18

Diisopropylamidoborane(η-cyclopentadienyl)(η-fluoren-9-yl)zirconium Dichloride

18A) Preparation of Diisopropylamido(9-fluorenyl)boron chloride

The reaction conditions of Example 17A) were substantially repeated excepting that diisopropylamidodichlorobo-ron was used in place of bis(trimethylsilyl)amidodichloroboron. At the end of the reaction, solvent was removed, residue was extracted with CH$_2$Cl$_2$ and filtered. Volatile components were removed to give the product (0.91 g, 98 percent) as a yellowish solid.

$^1$H NMR (400 MHz, CDCl$_3$): δ 1.36 (br, 6H), 1.79 (br, 6H), 4.41(br,1H), 7.35 (t, 2H, J=7.7 Hz), 7.42 (t, 2H, J=7.5 Hz), 7.50 (br, d, 2H, )=4.7 Hz), 7.88 (d, 2H, J=7.3 Hz). $^{13}$C NMR (100 MHz, CDCl$_3$) δ 24.5 (br), 43.2 (br), 48.5 (br), 120.2, 124.4, 126.4, 126.9, 141.1 (br), 146.9. $^{11}$B NMR (115.5 MHz, CDCl$_3$) δ 37.2. HRMS (El) Calculated for C$_{19}$H$_{23}$BNCl, 311.1612; found, 311.1613.

18I3) Diisopropylamido(cyclopentadienyl)(9-fluorenyl) borane

The reaction conditions of Example 17B were substantially repeated excepting that diisopropylamido(9-fluorenyl) boron was used in place of bis(trimethylsilyl)amido(9-fluorenyl)boron chloride. Reaction of CpNa/THF (0.96 g, 9.60 mmol) and diisopropylamido(9-fluorenyl)boron chloride (2.98 g, 10.00 mmol) gave a reaction mixture which was extracted with hexane and filtered. Volatiles were removed to give the product (2.11 g, 62 percent) as a yellow solid.

HRMS (El), Calculated for C$_{24}$H$_{28}$BN, 341.2315, found, 341.2329.

18C) Preparation of diisopropylamidoborane(n-cyclopentadienyl)(η-fluoren-9-yl)zirconium dichloride.

The reaction conditions of Example 17C) were substantially repeated excepting that diisopropylamido(9-fluorenyl) boron (1.39 g, 4.08 mmol) was used in place of bis (trimethylsilyl)amido(9-fluorenyl)boron. The crude reaction mixture from this reaction was extracted with toluene and filtered. The solution was concentrated, pentane was added and cooled to −78° C. to give the product (0.75 g, 36 percent yield) as a red solid.

mp=280–282° C. $^1$H NMR (500 MHz. C$_6$D$_6$): δ 1.01 (d, 6H, J=6.6 Hz), 1.22 (d, 6H,J=6.9 Hz), 3.67 (pent, 1 H, J=6.6 Hz), 3.80 (pent, 1 H, J=6.6 Hz), 5.30 (t, 2H, J=2.4 Hz), 6.38 (t, 2H, J=2.4 Hz), 7.05 (d, 2H, J=8.1 Hz), 7.12 (t, 2H, J=7.5 Hz), 7.46 (t, 2H, J=7.5 Hz), 7.92 (d, 2H, J=8.5 Hz). $^{13}$C NNIR (90 MHz, CDCl$_3$) 6 24.2, 25.4, 49.1, 49.8, 106.9, 122.2, 123.2, 125.4, 125.8, 129.0, 147.9, 157.1. $^{11}$B NMR (115.5 MHz, C$_6$D$_6$) δ 39.4. EA, calculated for C$_{24}$H$_{28}$BNZrCl$_2$: C, 57.25, H, 5.57, N, 2.78. Found: C, 55.44; H, 5.30; N, 2.62.

Example 19

Bis(trimethylsilyl)amidoborane bis(η-inden-1-yl) zirconium Bis(dimethylamide)

Bis(trimethylsilyl)amidoboronbis(inden-1-yl) was prepared by reacting lithium indenide (0.50 g, 4.10 mmol) and bis(trimethylsilyl)amidoboron dichloride, (0.48 g, 2.00 mmol) in THF to give the product (0.75 g, 94 percent) as a yellowish solid.

$^1$H NMR (400 MHz, C$_6$D$_6$, major isomer): δ 0.32 (s, 18H), 3.64 (s, 2H), 6.08 (dd, 2H, J=5.5, 1.8 Hz), 6.48 (dd, 2H, J=5.2 Hz), 6.82 (d., 2H, J=7.3 Hz), 0.93 (dt, 2H, J=7.1, 1.2 Hz), 7.20 (m, 4H). $^{11}$B NMR (115.5 MHz, C$_6$D$_6$) δ56.8. HRMS (El) calculated for C$_{24}$H$_{32}$BNSi$_2$, 401.2166; found, 401.2182. EA, Calculated for C$_{24}$H$_{32}$BNSi$_2$, C, 71.82; H, 7.98; N, 3.49. Found: C, 70.06; H, 8.06; N, 3.36.

The bis(trimethylsilyl)amidoboron bis(inden-1-yl) (0.27 g, 0.67 mmol) and Zr(NMe$_2$)$_4$ (0.18 g, 0.67 mmol) were then combined in toluene (10 ml) 2 hours at 65° C. to give a red solution. Volatile components were removed under reduced pressure to afford the product as a red foam.

$^1$H NMR (400 MHz, C$_6$D$_6$): δ 0.26 (s. 18H), 2.53 (s, 12H), 5.95 (d, 2H, J=2.9 Hz), 6.64 (d, 2H, J=2.9 Hz), 6.68

(t, 2H, J=7.5 Hz), 6.95 (t, 2H, J=7.6 Hz), 7.30 (d, 2H, J=8.5 Hz), 7.45 (d, 2H, J=8.8 Hz). $^{13}$C NMR (100 MHz, C$_6$D$_6$) δ5.6, 47.9, 105.1, 111.5, 122.2, 122.9, 124.2, 126.4, 128.5. $^{11}$B NMR (115.5 MHz, C$_6$D$_6$) δ50.3. HRMS (El) calculated for C$_{28}$H$_{42}$BN$_3$Si$_2$Zr, 577.2057; found, 577.2061.

Example 20

Bis(trimethyl)silyl)amidobis(η-inden-1-yl)boranezirconium Dichloride

Bis(trimethylsilyl)amidoboron bis(inden-1-yl) (0.45 g, 1.12 mmol) and Zr(NMe$_2$)$_4$ (0.30 g, 1.12 mmol) were combined in THF to give an intermediate which was not further purified. Volatile components were removed under reduced pressure and replaced with CH$_2$Cl$_2$ (10 ml). The mixture was stirred with trimethylsilane chloride (1.42 ml, 11.20 mmol) overnight at room temperature. Volatile components were again removed under reduced pressure and the residue was extracted with CH$_2$Cl$_2$ and filtered. The solution was concentrated, layered with pentane, and cooled to −78° C. to give the desired product (0.54 g, 86 percent) as an orange solid.

$^1$H NMR (500 MHz, C$_6$D$_6$), δ 0.20 (s, 18H), 5.54 (d, 2H, J=3.3 Hz), 6.68 (dd, 2H, J=2.1, 0.9 Hz), 6.85 (t. 2H, J=7.0 Hz), 7.04 (dd, 2H, J=8.1, 1.1 Hz), 7.17 (m, 2H, overlapped with solvent residue peak), 7.33 (d, 2H, J=8.4 Hz). $^{13}$C NMR (100 MHz, C$_6$D$_6$) δ 5.3, 112.8, 113.0, 123.6, 126.5, 127.1, 127.8, 132.1. $^{11}$B NMR (115.5 MHz, C$_6$D$_6$) δ 48.5. HRMS (El) calculated for C$_{24}$H$_{30}$BNSi$_2$Cl$_2$Zr, 559.0434; found, 559.0432.

Example 21

Preparation of Rac-diisopropylamidoborane-bis-η$^2$-isopropyl-4-phenyl indenyl)zirconium η$^4$-1,4-diphenyl-1,3-butadiene

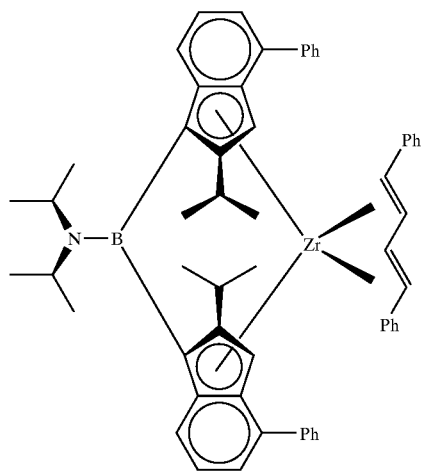

21A) 2-Isopropyl-4-phenyl indene

Sodium hydride (2.1 g, 60 percent dispersion in oil) was placed in 500 ml flask under nitrogen atmosphere. Hexane (about 20 ml) was added to remove the oil, the mixture was stirred briefly. After stirring stopped the NaH was allowed to settle and the liquids were removed by syringe. This procedure was repeated once more, then THF (200 ml) was added to the NaH and the suspension was cooled with an ice bath. Diethyl isopropylmalonate (10.10 g, 50.00 mmol) in THF (100ml) was added via an addition funnel over 30 min. After addition of the malonate was complete, the solution was stirred for an additional 40 min. A THF solution (30 ml) of 2-phenylbenzyl bromide (12.5 g, 50.5 mmol) was added via addition funnel and the mixture was stirred overnight. The next morning 100 ml of 1N ammonium chloride was added. The solution was diluted with ether (200 ml) and the organic layer was washed with brine, dried over Na$_2$SO$_4$, and stripped of solvent under reduced pressure. The orange red oil was used without further purification.

The crude alkylation product was dissolved in ethanol (300 ml) and water (75 ml). Potassium hydroxide (20 g) was added and the mixture was refluxed overnight. After cooling, ethanol was stripped under reduced pressure. Hexane was added and stirred for 1 hour to dissolve any undesired organic materials. The hexane was decanted and water was added (about 150 ml). The solution was made acidic (to pH 1) by adding concentrated HCl. The desired carboxylic product was extracted with ether, dried over Na$_2$SO$_4$, and stripped under reduced pressure. NMR spectra of the crude product (10.74 g, 80 percent) indicated that ester hydrolysis and decarboxylation were complete. The crude product, which solidified to a tan solid, was used without further purification.

Thionyl chloride (50 ml) was added to the carboxylic acid and the mixture was stirred overnight at room temperature to dissolve the acid. The excess thionyl chloride was removed under reduced pressure and the remaining acid chloride was dissolved in methylene chloride (75 ml). This solution was added dropwise via an addition funnel to a suspension of aluminum chloride (5.70 g, 42.5 mmol) in methylene chloride (25 ml) and cooled with an ice bath. The reaction was allowed to warm slowly to room temperature and stirred overnight. The solution was poured onto ice (about 100 ml) and stirred vigorously for 1 hour. The organic layer was separated, the aqueous layer was washed once with ether and the combined organic layers were washed with brine, dried over Na$_2$SO$_4$, and stripped under reduced pressure. The crude 2-isopropyl-4-phenylindanone (10.0 g) as an orange-brown oil was used without further purification.

2-Isopropyl-4-phenylindanone (12.1 g, 48 mmol) was stirred in a mixture of THF and methanol (100 ml; 2/1) while sodium borohydride (1.5 g, 40 mmol) was added in small portions over 30 min. After stirring overnight, ice (about 50 ml) was added and the mixture was stirred for 0.5 h. The THF and MeOH were removed under reduced pressure. Ether (about 250 ml) was added, the pH was adjusted to pH 1 by the addition of aqueous HCl and the ether layer was separated. The ether was washed with saturated sodium bicarbonate solution, then brine, dried over Na$_2$SO$_4$, and evaporated under reduced pressure. The mixture of alcohol isomers (11.0 g, 43.5 mmol, 90 percent) was obtained as a waxy tan solid. It was used without purification.

The crude mix of isomeric alcohols was dissolved in toluene (150 ml) to which p-toluene sulfonic acid (0.5 g) was added. The solution was refluxed in a flask equipped with a Dean-Stark trap for 1.5 h then cooled. Solid sodium bicarbonate was added and the mixture was stored overnight in a refrigerator. The next morning water (100 ml) was added and the organic layer was separated, dried over Na$_2$SO$_4$, and stripped under reduced pressure. The product, 2-isopropyl-4-phenylindene (10.4 g) was obtained as a brown oil. Analysis by GC indicated a purity of >96 area percent. This material was stored cold under an inert atmosphere until ready for further conversion.

$^1$H-NMR (CDCl$_3$); δ 1.18 (d, 6H), 2.74 (sept, 1H), 3.39 (s, 2H), 6.53 (s, 1 H), 7.09–7.55 (m, 8H).

21B) Lithium 2-isopropyl-4-phenylindenide

To a toluene solution (25 ml) of 2-isopropyl-4-phenylindene (3.34 g, 14.25 mmol), in a glovebox filled with argon, was added n-butyl lithium (5.500 ml, 13.75 mmol). The mixture was stirred at room temperature overnight. The toluene was removed under reduced pressure. Hexane (20 ml) was added and removed under reduced pressure then added again (50 ml). The mixture was stirred for 1 h then filtered, washed with about 15 ml hexane and the filtrate dried under vacuum. The lithium indenide product (3.09 g) was obtained as an orange-brown powder. This material was stored in the glovebox until needed.

$^1$H-NMR (d$_8$-THF): δ 1.27 (d, 6H), 3.02 (sept, 1H), 5.84 (s,1H), 6.06 (s, 1H), 6.42–6.51 (m, 2H), 7.15 (t, 1H), 7.18 (d, 1H), 7.26 (t, 2H), 7.82 (d, 2H). $^{13}$C-NMR (de-THF): ppm 147.00, 126.70, 113.92, 113.40, 91.01, 89.77, 30.62, 25.78.

21C) N,N-diisopropylamido bis(2-isopropyl-4-phenylindenyl) borane

To 25 ml toluene solution of N,N-diisopropylamidoboron dichloride (0.501 g, 2.75 mmole) at room temperature was added drop wise potassium (2-isopropyl-4-phenyl)indenide (1.50 g, 5.51 mmole in 20 ml toluene). The mixture was heated to reflux and stirred for 6 hours. The solution was cooled to room temperature, filtered through a medium frit, and solvent was removed under reduced pressure to give a light yellow solid (1.57 g, 99 percent). This material was further purified by column chromatography (silica gel/ hexane) to yield 0.68 (38 percent) of a light yellow solid (96 percent pure by GC). 21 D) rac-diisopropylamidoborane-bis-η$^5$-(2-isopropyl-4-phenyl indenyl)zirconium η$^4$-1,4-diphenyl-1,3-butadiene In a glove box, N,N-diisopropylamino bis(2-isopropy-4-phenylindenyl) borane (0.380 g, 0.660 mmole) was dissolved in 20 ml of toluene, 2.1 equivalents of potassium bis(trimethylsilyl) amide (0.276, 1.38 mmole) was added and the resulting mixture was stirred at room temperature for 24 hours, Removed volatiles under reduced pressure and washed. The resulting orange solid was combined with 10 ml of hexane, filtered and pumped dry. The dipotassium salt residue (0.415 g, 97 percent, 0.635 mmole) was redissolved in 20 ml of toluene, and (1,4-diphenyl-1,3-butadiene)bis(triethylphosphine)zirconium dichloride (0.384 g, 0.635 mmole) was added. The solution was stirred for 2 h at room temperature, followed by heating at 80° C. for 6 hours. The product mixture was cooled to room temperature, filtered through diatomaceous earth and the solvent of the filtrate was removed under reduced pressure. Further purification was carried out by recrystallization from hexane to yield 0.21 g (36 percent) of product as a dark red solid.

$^1$H NMR (C$_6$D$_6$): δ 7.62(d, 2H); 7.42–6.7, (mm, 24 H); 5.79 (s, 2H); 4.5, sept, 2H); 3.45–3.57 (dd, 2H); 2.8–2.9 (sept, 2H)1.65–1.72 (dd, 2H); 1.35(d, 12H) 1.2–1.3 (m, 12H).

Example 22

Supported Rac-diisopropylamidoborane-bis-η$^5$-methyl-4-phenyliden-1-yl)zirconium η$^4$-1,4-diphenyl-1,3-butadiene A toluene solution of methyldi(octyl)ammonium hydroxyphenyltris(pentafluorophenyl)borate (825 μl, 0.040M, 33.0 μmol, the ammonium cation being derived from a mixture of amines available commercially as methylbistallowamine) and a toluene solution of methyl aluminum (TEA) (363 μl, 0.10M, 36.3 μmol) were combined and mixed for 30 seconds. The resulting solution was then added to 1.0 g of TEA-treated silica (Grace-Davison 948 silica, calcined at 250° C. for 4 h, treated with 1.5 mmol TEA/g, washed with toluene and mixed hexanes and dried under reduced pressure). The mixture was shaken by hand to break-up clumps and then mechanically agitated for 5 minutes. The volatile components were then removed under reduced pressure. A toluene solution of rac-diisopropylamidoborane-bis-η$^5$-(2-methyl-4-phenylinden-1-yl)zirconium η$^4$-1,4-diphenyl-1,3-butadiene (1500 μl. 0.020M, 30.0 umol) was added. The mixture was shaken by hand to break-up clumps and then mechanically agitated for 5 minutes. The volatile components were once again removed under reduce pressure to give the supported catalyst as a blue/gray solid.

Example 23

Supported Rac-dimethylamidoborane-bis-η$^5$-(2-methyl-4-phenylinden-1-yl)zirconium η$^4$-1,4-diphenyl-1,3-butadiene A toluene solution of methyldi(octyl)ammonium hydroxyphenyltris(pentafluorophenyl)borate (578 μl, 0.040M, 23.1 umol) and a toluene solution of triethyl aluminum (254 μl, 0.100M, 25.4 μmol) were added and mixed for 30 seconds. This solution was then added to 0.70 g of TEA-treated silica (Grace-Davison 948 silica, calcined at 250° C. for 4 h, treated with 1.5 mmol TEA/g, washed with toluene and hexanes and dried under reduced pressure). The mixture was shaken by hand to break-up clumps and then mechanically agitated for 5 minutes. The volatile components were then removed under reduced pressure. A toluene solution of rac-dimethylamidoborane-bis-η$^5$-(2-methyl-4-phenylinden-1-yl)zirconium η$^4$-1,4-diphenyl-1,3-butadiene (1050 μl, 0.020M, 21.0 umol) was added. The mixture was shaken by hand to break-up clumps and then mechanically agitated for 5 minutes. The volatile components were then removed under reduced pressure to give a teal blue solid.

Example 24

Supported Rac-diisopropylamidoborane-bis-η$^5$-(2-methyl-4-phenylinden-1-yl)zirconium η$^4$-1,4-diphenyl-1,3-butadiene A toluene solution of methylbis(octadecyl)ammonium bis(tris(pentafluorophenyl)aluminane)imidazolide (689 μl, 0.0479M, 33.0 μmol, prepared according to USSN 091251, 664, filed Feb. 17, 1999) was added to 1.0 g of TEA-treated (Grace-Davison 948 silica, calcined at 250° C. for 4 h, treated with 1.5 mmol TEA/g, washed with toluene and hexanes and dried under reduced pressure). The mixture was shaken by hand to break-up clumps and then mechanically agitated for 5 minutes. The volatile components were then removed under reduced pressure. A toluene solution of rac-diisopropylamidoborane-bis-η$^5$-methyl-4-phenylinden-1-yl)zirconium η$^4$-1,4-diphenyl-1,3-butadiene (1500 μl, 0.020M, 30.0 μmol) was added. The mixture was shaken by hand to break-up clumps and then mechanically agitated for 5 minutes. The volatile components were then removed under reduced pressure to give a blue solid.

Example 25

Supported Rac-dimethylamidoborane-bis-η$^5$-(2-methyl-4-phenylinden-1-yl)zirconium η$^4$-1,4-diphenyl-1,3-butadiene Under an argon atmosphere, a toluene solution of methylbis(octadecyl)ammonium bis(tris(pentafluorophenyl)

aluminane)imidazolide (689 μl, 0.0479M, 33.0 μmol) was added to 1.0 g of TEA-treated (Grace-Davison 948 silica, calcined at 250° C. for 4 h, treated with 1.5 mmol TEA/g, washed with toluene and hexanes and dried under reduced pressure). The mixture was shaken by hand to break-up clumps and then mechanically agitated for 5 minutes. The volatile components were then removed under reduced pressure. A toluene solution of rac-dimethylamidoborane-bis-η$^5$-(2-methyl-4-phenylinden-1-yl)zirconium η$^4$-1,4-diphenyl-1,3-butadiene (1500 μl, 0.020M, 30.0 μmol) was added. The mixture was shaken by hand to break-up clumps and then mechanically agitated for 5 minutes. The volatile components were then removed under reduced pressure to give a light blue solid.

Gas phase polymerization

A 2.5-L stirred, fixed bed autoclave was charged with 200 g dry NaCl containing 0.1 g of KH as a scavenger. Stirring was begun at 300 rpm. The reactor was pressurized to 0.8 MPa ethylene and heated to 72° C. 1-hexene was introduced to the reactor followed by the addition of hydrogen. In a separate vessel, 0.05 g of catalyst was mixed with an additional 0.1 g KH scavenger. The combined catalyst and scavenger were subsequently injected into the reactor. Ethylene pressure was maintained on demand while hexene and hydrogen were fed to the reactor to maintain their respective concentrations. The temperature of the reactor was regulated by a circulating water bath. After 90 minutes the reactor was depressurized, and the salt and polymer were removed. The polymer was washed with copious quantities of distilled water to remove the salt, dried at 60° C., and then stabilized by addition of a hindered phenol antioxidant (Irgaflox™ 1010 from Ciba Geigy Corporation) and 133 mg of a phosphorus stabilizer. Activity values were calculated based on ethylene uptake. Results are contained in Table 1.

TABLE 1

| Run | Cat. | hexene (ppm) | H$_2$ (ppm) | Activity[1] | Density[2] | MMI[3] (dg/m) | Mw × 10$^{-3}$ | MWD | I$_{10}$/I$_2$ |
|---|---|---|---|---|---|---|---|---|---|
| 1 | EX. 22 | 5000 | 0 | 122.7 | 0.899 | <0.01 | 315 | 2.84 | — |
| 2 | Ex. 23 | 5000 | 0 | 115.0 | 0.900 | <0.01 | 201 | 2.92 | — |
| 3 | " | 4000 | 500 | 84.1 | 0.905 | <0.01 | 272 | 3.07 | — |
| 4 | " | 5000 | 0 | 134.1 | 0.899 | <0.01 | 323 | 2.26 | — |
| 5 | " | 5000 | 3000 | 120.0 | 0.898 | <0.01 | 222 | 3.24 | |
| 6 | " | 5000 | 6000 | 116.7 | 0.900 | <0.01 | 192 | 2.50 | |
| 7 | Ex. 24 | 5000 | 6000 | 140.7 | 0.899 | 0.026 | 180 | 3.16 | 34.2 |
| 8 | Ex. 25 | 5000 | 6000 | 54.0 | 0.898 | <0.01 | 194 | 2.56 | |
| 9[4] | Ex. 23 | 5000 | 8000 | 133.8 | 0.901 | 0.04 | 187 | 2.84 | 23.0 |

[1]g polymer/g cat. + cocat./hr/(MPa × 0.1)
[2]density is determined by displacement technique using methylethylketone
[3]melt index, I$_2$, ASTM D-1238, 190° C./2.16 Kg, I$_{10}$ ASTM D-1238, 190° C./10 Kg
[4]reaction run for 5 hours

What is claimed is:

1. An olefin polymerization process comprising contacting one or more olefin monomers under gas phase polymerization conditions with a catalyst composition comprising a metal complex corresponding to the following formula:

$$\begin{array}{c} TZ{-}Y^1 \\ | \quad\quad MQ_j \\ TZ{-}Y^2 \end{array}$$

wherein:
M is titanium, zirconium, or hafnium in the +4, +3, or +2 oxidation state;

Y$^1$ and Y$^2$ are independently an anionic, cyclic or non-cyclic, ρ-bonded group, NR$^1$, PR$^1$; NR$^1{}_2$ or PR$^1{}_2$;

Z is boron or aluminum;

Q is a neutral, anionic or dianionic ligand group depending on the oxidation state of M;

j is 1, 2 or 3 depending on the oxidation state of M and the electronic nature of Q;

T independently each occurrence is;

$$R^1{}_2N{-} \quad , \quad R^5{-}\!\!\stackrel{N-R^1}{\underset{N-R^1}{\Big\langle}} \quad , \quad R^1{-}\!\!\stackrel{R^1\;N-R^1}{\underset{R^1\;N-R^1}{\Big\langle}} \quad \text{or}$$

$$R^1{-}\!\!\stackrel{R^1\;O}{\underset{R^1\;N-R^1}{\Big\langle}} \quad ;$$

wherein R$^1$ is independently each occurrence hydrogen, a hydrocarbyl group, a tri(hydrocarbyl)silyl group, or a tri(hydrocarbyl)silyhydrocarbyl group, said R$^1$ groups containing up to 20 atoms not counting hydrogen;

R$^5$ is R$^1$ or N(R$^1$)$_2$; and two R$^1$ groups together or one or more R$^1$ groups together with R$^5$ may optionally be joined to form a ring structure.

2. The process of claim 1 wherein the metal complex corresponds to the following formulas:

[cyclopentadienyl-type structure with R$^2$ substituents, T—Z linkages, and MQ$_j$]

-continued

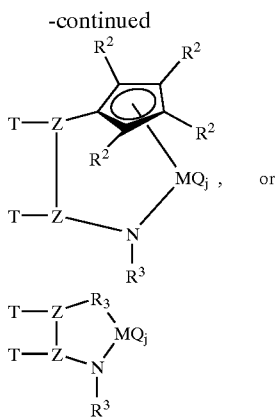

or

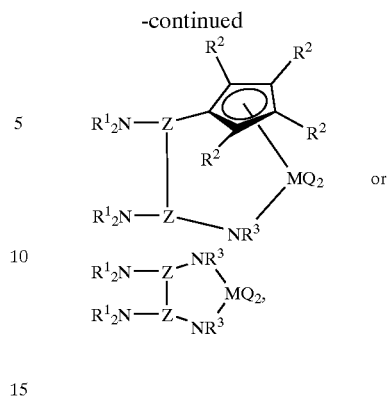

wherein $R^2$ is hydrogen, or a hydrocarbyl, halohydrocarbyl, dihydrocarbylaminohydrocarbyl, tri(hydrocarbylsilyl)hydrocarbyl, $Si(R^3)_3$, $N(R^3)_2$, or $OR^3$ group of up to 20 carbon or silicon atoms, and optionally two adjacent $R^2$ groups can be joined together, thereby forming a fused ring structure, especially an indenyl ligand or a substituted indenyl ligand; and $R^3$ is independently hydrogen, a hydrocarbyl group, a trihydrocarbylsilyl group or a trihydrocarbylsilylhydrocarbyl group, said $R^3$ having up to 20 atoms not counting hydrogen.

3. The process of claim 2 wherein M is in the +4 oxidation state, j=2 and Q independently each occurrence is halide, hydride, hydrocarbyl, silylhydrocarbyl, hydrocarbyloxide, or dihydrocarbylamide, said Q having up to 20 atoms not counting hydrogen, or two Q groups together form an alkanediyl group or a conjugated $C_{4-40}$ diene ligand that together with M form a metallocyclopentene.

4. The process of claim 2 wherein M is in the +3 oxidation state, j=1 and Q is either 1) a monovalent anionic stabilizing ligand selected from the group consisting of alkyl, cycloalkyl, aryl, silyl, amido, phosphido, alkoxy, aryloxy, sulfido groups, and mixtures thereof, said Q being further substituted with an amine, phosphide, ether, or thioether containing substituted able to form a coordinate-covalent bond or chelating bond with M said ligand having up to 50 atoms not counting hydrogen; or 2) a $C_{3-10}$ hydrocarbyl group comprising an ethylenic unsaturation able to form an $\eta^3$-bond with M.

5. The process of claim 2 wherein M is in the +2 oxidation state, j=1 and Q is a neutral conjugated diene, optionally substituted with one or more in(hydrocarbyl)silyl or tri(hydrocarbylsilyl)hydrocarbyl groups, said Q having up to 40 carbon atoms and forming a ρ-complex with M.

6. The process of claim 3 wherein the natal complex corresponds to the following formulas:

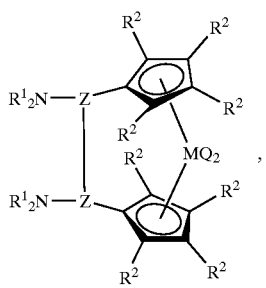

wherein Q independently each occurrence is a halide, hydrocarbyl, hydrocarbyloxy, or dihydrocarbylamide group of up to 10 atoms not counting hydrogen, or two Q groups together form a $C_{4-20}$ diene ligand that together with M forms a metallocyclopentene.

7. The process of claim 4 wherein the metal complex corresponds to the following formulas:

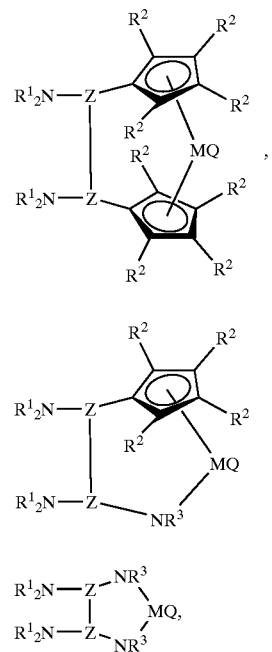

wherein Q each occurrence is a monovalent anionic stabilizing ligand selected from the group consisting of alkyl, cycloalkyl, aryl, and silyl groups, said group being further substituted with one or more amine, phosphine, or ether substituents able to form a coordinate-covalent bond or chelating bond with M, and said Q having up to 30 non-hydrogen atoms; or Q is a $C_{3-10}$ hydrocarbyl group comprising an ethylenic unsaturation able to form an $\eta^3$ bond with M.

8. The process of claim 5 wherein the metal complex corresponds to the following formulas:

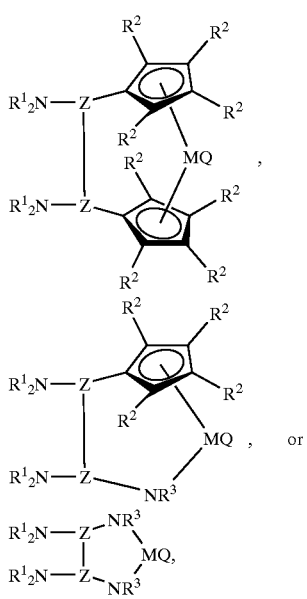

wherein Q each occurrence is a neutral conjugated diene, optionally substituted with one or more tri(hydrocarbyl)silyl groups or tri(hydrocarbyl)silyhydrocarbyl groups, said Q having up to 30 atoms not counting hydrogen and forming a ρ-complex with M.

9. The process of any one of claims 1–8 wherein M is zirconium or hafnium.

10. The process of claim 9 wherein Z is boron.

11. The process of claim 1 wherein the metal complex is dichloro-[1,2-Bis(2,6-diisopropylanilide)-1,2-bis(dimethylamido)diborane] titanium, dimethyl [1,2-Bis(2,6-diisopropylanilide)-1,2-bis(dimethylamido)diborane] titanium, dibenzyl [1,2-Bis(2,6-diisopropylantide)-1,2-bis(dimethylamido)diborane) zirconium, or rac-1,2-bis(dimethylamido)diborane)bis(2-methyl-4-phenylinden-1-yl)zirconium $\eta^4$-1.4-diphenyl-1,3-butadiene.

12. The process of claim 1 wherein the catalyst additionally comprises a support material.

13. The process of claim 1 which is a continuous gas phase polymerization.

14. The process of claim 13 wherein ethylene is homopolymerized, or a mixture of $C_{2-8}$ olefins is copolymerized.

15. The process of any one of claims 1, 13 or 14 wherein the resulting polymer contains long chain branching.

* * * * *

UNITED STATES PATENT AND TRADEMARK OFFICE
CERTIFICATE OF CORRECTION

PATENT NO.   : 6,891,005 B2
DATED        : May 10, 2005
INVENTOR(S)  : David D. Devore et al.

It is certified that error appears in the above-identified patent and that said Letters Patent is hereby corrected as shown below:

Column 78,
Line 2, "*p*-bonded" should read -- π-bonded --.

Column 79,
Line 43, "substituted" should read -- substituent --.
Line 50, "in(hydrocarbyl)silyl" should read -- tri(hydrocarbyl)silyl --;
Line 52, "*p*-complex" should read -- π-complex --.
Line 53, "natal" should read -- metal --.

Column 82,
Line 3, "*p*-complex" should read -- π-complex --.
Line 11, "2,6-diisopropylantide)" should read -- (2,6-diisopropylanilde) --;
Line 14, "1.4-diphenyl" should read -- 1,4-diphenyl --.

Signed and Sealed this

Twentieth Day of September, 2005

JON W. DUDAS
*Director of the United States Patent and Trademark Office*